United States Patent
Huang et al.

(10) Patent No.: US 12,076,319 B2
(45) Date of Patent: Sep. 3, 2024

(54) THERAPEUTIC REGIMENS FOR TREATMENT OF PAROXYSMAL NOCTURNAL HEMOGLOBINURIA

(71) Applicant: Achillion Pharmaceuticals, Inc., Blue Bell, PA (US)

(72) Inventors: Mingjun Huang, Rockville, MD (US); Dharaben Patel, Orange, CT (US); Steven D. Podos, New Haven, CT (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/700,910

(22) Filed: Dec. 2, 2019

(65) Prior Publication Data

US 2020/0101071 A1   Apr. 2, 2020

Related U.S. Application Data

(63) Continuation of application No. 16/053,716, filed on Aug. 2, 2018, now abandoned.

(60) Provisional application No. 62/593,669, filed on Dec. 1, 2017, provisional application No. 62/540,451, filed on Aug. 2, 2017.

(51) Int. Cl.
| | |
|---|---|
| *A61K 31/506* | (2006.01) |
| *A61K 39/00* | (2006.01) |
| *A61K 39/395* | (2006.01) |
| *A61P 7/00* | (2006.01) |
| *C07K 16/18* | (2006.01) |

(52) U.S. Cl.
CPC ........ *A61K 31/506* (2013.01); *A61K 39/3955* (2013.01); *A61P 7/00* (2018.01); *C07K 16/18* (2013.01); *A61K 2039/505* (2013.01); *C07K 2317/76* (2013.01)

(58) Field of Classification Search
CPC . A61K 31/401; A61K 31/416; A61K 31/4155
See application file for complete search history.

(56) References Cited

U.S. PATENT DOCUMENTS

| | | | |
|---|---|---|---|
| 5,628,984 A | 5/1997 | Boucher, Jr. | |
| 6,319,897 B1 | 11/2001 | Lambris et al. | |
| 6,489,476 B1 | 12/2002 | Dang et al. | |
| 6,653,340 B1 | 11/2003 | Babu et al. | |
| 7,888,323 B2 | 2/2011 | Lambris et al. | |
| 7,989,589 B2 | 8/2011 | Lambris | |
| 7,999,081 B2 | 8/2011 | Tedesco et al. | |
| 8,168,584 B2 | 5/2012 | Deschatelets et al. | |
| 8,241,628 B2 | 8/2012 | Diefenbach-Streiber et al. | |
| 8,580,735 B2 | 11/2013 | Francois et al. | |
| 8,883,158 B2 | 11/2014 | Diefenbach-Streiber et al. | |
| 8,946,145 B2 | 2/2015 | Lambris et al. | |
| 9,056,076 B2 | 6/2015 | Deschatelets et al. | |
| 9,085,555 B2 | 7/2015 | Altmann et al. | |
| 9,169,307 B2 | 10/2015 | Lambris et al. | |
| 9,291,622 B2 | 3/2016 | Zhang et al. | |
| 9,371,365 B2 | 6/2016 | Lambris et al. | |
| 9,421,240 B2 | 8/2016 | Francois et al. | |
| 9,468,661 B2 | 10/2016 | Altmann et al. | |
| 9,796,741 B2 * | 10/2017 | Gadhachanda | A61K 31/444 |
| 10,092,547 B2 | 10/2018 | Wiles et al. | |
| 10,138,225 B2 * | 11/2018 | Wiles | C07D 495/04 |
| 10,660,876 B2 | 5/2020 | Wiles et al. | |
| 10,662,175 B2 | 5/2020 | Wiles et al. | |
| 10,689,409 B2 | 6/2020 | Gadhachanda et al. | |
| 10,807,952 B2 | 10/2020 | Wiles et al. | |
| 10,822,352 B2 | 11/2020 | Wiles et al. | |
| 10,906,887 B2 | 2/2021 | Wiles et al. | |
| 10,919,884 B2 | 2/2021 | Wiles et al. | |
| 11,001,600 B2 | 5/2021 | Wiles et al. | |
| 11,053,253 B2 | 7/2021 | Wiles et al. | |
| 11,084,800 B2 | 8/2021 | Wiles et al. | |
| 11,407,738 B2 | 8/2022 | Wiles et al. | |
| 11,447,465 B2 | 9/2022 | Wiles et al. | |
| 2002/0133004 A1 | 9/2002 | Sekiyama et al. | |
| 2005/0228000 A1 | 10/2005 | Smallheer et al. | |
| 2005/0267108 A1 | 12/2005 | Hsieh et al. | |
| 2007/0155712 A1 | 7/2007 | Zahn et al. | |
| 2008/0075720 A1 | 3/2008 | Holers et al. | |
| 2008/0075728 A1 | 3/2008 | Newman | |
| 2008/0108691 A1 | 5/2008 | Hamann et al. | |
| 2010/0041628 A1 | 2/2010 | Enomoto et al. | |
| 2011/0280808 A1 | 11/2011 | Kroth et al. | |
| 2012/0231471 A1 | 9/2012 | Sato et al. | |
| 2012/0237515 A1 | 9/2012 | Bell et al. | |
| 2012/0295884 A1 | 11/2012 | Altmann et al. | |
| 2013/0029912 A1 * | 1/2013 | Holers | A61K 38/178 514/13.5 |
| 2013/0035392 A1 | 2/2013 | McGeer et al. | |
| 2013/0296377 A1 | 11/2013 | Adams et al. | |
| 2013/0324482 A1 | 12/2013 | Francois et al. | |
| 2014/0050739 A1 | 2/2014 | Francois et al. | |
| 2014/0323407 A1 | 10/2014 | Francois et al. | |
| 2014/0371133 A1 | 12/2014 | Francois et al. | |
| 2015/0141455 A1 | 5/2015 | Altmann et al. | |

(Continued)

FOREIGN PATENT DOCUMENTS

| | | |
|---|---|---|
| CN | 103402996 A | 11/2013 |
| EA | 201890594 A1 | 8/2018 |

(Continued)

OTHER PUBLICATIONS

US, U.S. Pat. No. 9,598,446 B2, U.S. Appl. No. 14/631,312, Gadhachanda et al., Mar. 21, 2017.

(Continued)

*Primary Examiner* — Theodore R. Howell
*Assistant Examiner* — George W Kosturko
(74) *Attorney, Agent, or Firm* — Clark & Elbing LLP

(57) ABSTRACT

Provided herein are methods for treating a subject with PNH comprising administering to a subject a therapeutically effective amount of complement component C5 (C5) inhibitor, complement component C3 (C3) inhibitor, or complement factor B (CFB) inhibitor in combination with a therapeutically effective amount of small molecule complement factor D (CFD) inhibitor of Formula I or Formula II, or a pharmaceutically acceptable salt thereof.

24 Claims, 17 Drawing Sheets

(56) References Cited

U.S. PATENT DOCUMENTS

| | | |
|---|---|---|
| 2015/0148374 A1 | 5/2015 | Hommel et al. |
| 2015/0158915 A1 | 6/2015 | Lambris et al. |
| 2015/0191462 A1 | 7/2015 | Hommel et al. |
| 2015/0239837 A1 | 8/2015 | Wiles et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2015/0322060 A1 | 11/2015 | Flohr et al. |
| 2016/0015810 A1 | 1/2016 | Deschatelets et al. |
| 2016/0024079 A1 | 1/2016 | Adams et al. |
| 2016/0060297 A1 | 3/2016 | Deschatelets et al. |
| 2016/0194359 A1 | 7/2016 | Francois et al. |
| 2016/0215020 A1 | 7/2016 | Cedric et al. |
| 2016/0215022 A1 | 7/2016 | Francois et al. |
| 2016/0361329 A1 | 12/2016 | Wiles et al. |
| 2016/0362398 A1 | 12/2016 | Wiles et al. |
| 2016/0362399 A1 | 12/2016 | Wiles et al. |
| 2016/0362432 A1 | 12/2016 | Wiles et al. |
| 2016/0362433 A1 | 12/2016 | Wiles et al. |
| 2017/0056428 A1 | 3/2017 | Wiles et al. |
| 2017/0057950 A1 | 3/2017 | Wiles et al. |
| 2017/0057983 A1 | 3/2017 | Wiles et al. |
| 2017/0057993 A1 | 3/2017 | Wiles et al. |
| 2017/0066783 A1 | 3/2017 | Wiles et al. |
| 2017/0189410 A1 | 7/2017 | Gadhachanda et al. |
| 2017/0202821 A1 | 7/2017 | Bekker |
| 2017/0202935 A1 | 7/2017 | Lambris et al. |
| 2017/0226142 A1 | 8/2017 | Wiles et al. |
| 2017/0260219 A1 | 9/2017 | Wiles et al. |
| 2017/0298084 A1 | 10/2017 | Wiles et al. |
| 2017/0298085 A1 | 10/2017 | Wiles et al. |
| 2018/0022766 A1 | 1/2018 | Wiles et al. |
| 2018/0022767 A1 | 1/2018 | Wiles et al. |
| 2018/0030075 A1 | 2/2018 | Wiles et al. |
| 2018/0072762 A1 | 3/2018 | Wiles et al. |
| 2018/0291046 A1 | 10/2018 | Wiles et al. |
| 2018/0291047 A1 | 10/2018 | Wiles et al. |
| 2018/0305375 A1 | 10/2018 | Wiles et al. |
| 2019/0023729 A1 | 1/2019 | Wiles et al. |
| 2019/0031692 A1 | 1/2019 | Wiles et al. |
| 2019/0085005 A1 | 3/2019 | Wiles et al. |
| 2020/0101071 A1 | 4/2020 | Huang et al. |
| 2020/0262818 A1 | 8/2020 | Wiles et al. |
| 2021/0332026 A1 | 10/2021 | Phadke et al. |
| 2022/0079943 A1 | 3/2022 | Huang et al. |

FOREIGN PATENT DOCUMENTS

| | | |
|---|---|---|
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2015-522008 A | 8/2015 |
| JP | 2015-522062 A | 8/2015 |
| JP | 2017-511815 A | 4/2017 |
| JP | 6400738 B2 | 10/2018 |
| JP | 2018-199714 A | 12/2018 |
| JP | 6537532 B2 | 7/2019 |
| JP | 6688352 B2 | 4/2020 |
| JP | 6877406 B2 | 5/2021 |
| KR | 2014-0027090 A | 3/2014 |
| RU | 2202344 C2 | 4/2003 |
| RU | 2470918 C2 | 12/2012 |
| WO | WO-1993/020099 A2 | 10/1993 |
| WO | WO-1995/029697 A1 | 11/1995 |
| WO | WO-1999/048492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2011/057158 A1 | 5/2011 |
| WO | WO-2012/093101 A1 | 7/2012 |
| WO | WO-2012/177782 A1 | 12/2012 |
| WO | WO-2013/166436 A1 | 11/2013 |
| WO | WO 2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/005150 A1 | 1/2014 |
| WO | WO-2014/009833 A2 | 1/2014 |
| WO | WO-2014/037480 A1 | 3/2014 |
| WO | WO-2014/116880 A1 | 7/2014 |
| WO | WO-2015/008861 A1 | 1/2015 |
| WO | WO-2015/021166 A2 | 2/2015 |
| WO | WO-2015/054569 A1 | 4/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO 2015/130838 A1 | 9/2015 |
| WO | WO-2015/130842 A2 | 9/2015 |
| WO | WO-2015/130845 A1 | 9/2015 |
| WO | WO-2015/130854 A1 | 9/2015 |
| WO | WO-2015130838 A1 * | 9/2015 ......... A61K 31/4178 |
| WO | WO 2017/035348 A1 | 3/2017 |
| WO | WO 2017/035349 A1 | 3/2017 |
| WO | WO 2017/035351 A1 | 3/2017 |
| WO | WO 2017/035352 A1 | 3/2017 |
| WO | WO 2017/035353 A1 | 3/2017 |
| WO | WO 2017/035355 A1 | 3/2017 |
| WO | WO 2017/035357 A1 | 3/2017 |
| WO | WO 2017/035360 A1 | 3/2017 |
| WO | WO 2017/035361 A1 | 3/2017 |
| WO | WO 2017/035362 A1 | 3/2017 |
| WO | WO-2017/035401 A1 | 3/2017 |
| WO | WO-2017/035405 A1 | 3/2017 |
| WO | WO-2017/035408 A1 | 3/2017 |
| WO | WO-2017/035409 A1 | 3/2017 |
| WO | WO-2017/035411 A1 | 3/2017 |
| WO | WO-2017/035413 A2 | 3/2017 |
| WO | WO-2017/035415 A1 | 3/2017 |
| WO | WO-2017/035417 A1 | 3/2017 |
| WO | WO-2017/035418 A1 | 3/2017 |
| WO | WO-2017/098328 A2 | 6/2017 |
| WO | WO 2017/127761 A1 | 7/2017 |
| WO | WO 2018/005552 A1 | 1/2018 |
| WO | WO-2018/026722 A1 | 2/2018 |
| WO | WO 2018/160889 A1 | 7/2018 |
| WO | WO-2018/160891 A1 | 9/2018 |
| WO | WO-2018/160892 A1 | 9/2018 |
| WO | WO-2019/028284 A1 | 2/2019 |
| WO | WO-2019/070714 A1 | 4/2019 |
| WO | WO-2020/069024 A1 | 4/2020 |
| WO | WO-2020/109343 A1 | 6/2020 |

OTHER PUBLICATIONS

US, U.S. Pat. No. 9,643,986 B2, U.S. Appl. No. 14/630,959, Wiles et al., May 9, 2017.

US, U.S. Pat. No. 9,663,543 B2, U.S. Appl. No. 14/631,785, Wiles et al., May 30, 2017.

US, U.S. Pat. No. 9,695,205 B2, U.S. Appl. No. 14/631,233, Wang et al., Jul. 4, 2017.

US, U.S. Pat. No. 9,732,103 B2, U.S. Appl. No. 14/631,440, Wiles et al., Aug. 15, 2017.

US, U.S. Pat. No. 9,732,104 B2, U.S. Appl. No. 14/631,683, Wiles et al., Aug. 15, 2017.

US, U.S. Pat. No. 9,758,537 B2, U.S. Appl. No. 14/631,828, Phadke et al., Sep. 12, 2017.

US, U.S. Pat. No. 9,796,741 B2, U.S. Appl. No. 14/631,625, Wiles et al., Oct. 24, 2017.

US, U.S. Pat. No. 9,828,396 B2, U.S. Appl. No. 14/631,090, Pais et al., Nov. 28, 2017.

(56) References Cited

OTHER PUBLICATIONS

US, U.S. Pat. No. 10,000,516 B2, U.S. Appl. No. 15/247,424, Wiles et al., Jun. 19, 2018.
US, U.S. Pat. No. 10,005,802 B2, U.S. Appl. No. 15/245,712, Wiles et al., Jun. 26, 2018.
US, U.S. Pat. No. 10,011,612 B2, U.S. Appl. No. 15/247,399, Wiles et al., Jul. 3, 2018.
US, U.S. Pat. No. 10,081,645 B2, U.S. Appl. No. 15/711,794, Wiles et al., Sep. 25, 2018.
US, U.S. Pat. No. 10,087,203 B2, U.S. Appl. No. 15/700,550, Wiles et al., Oct. 2, 2018.
US, U.S. Pat. No. 10,092,584 B2, U.S. Appl. No. 15/247,429, Wiles et al., Oct. 9, 2018.
US, U.S. Pat. No. 10,100,072 B2, U.S. Appl. No. 15/607,120, Wiles et al., Oct. 16, 2018.
US, U.S. Pat. No. 10,106,563 B2, U.S. Appl. No. 15/676,411, Wiles et al., Oct. 23, 2018.
US, U.S. Pat. No. 10,138,225 B2, U.S. Appl. No. 15/247,440, Wiles et al., Nov. 27, 2018.
US, U.S. Pat. No. 10,189,869 B2, U.S. Appl. No. 15/463,701, Gadhachanda et al., Jan. 29, 2019.
US, U.S. Pat. No. 10,253,053 B2, U.S. Appl. No. 16/140,148, Wiles et al., Apr. 9, 2019.
US, U.S. Pat. No. 10,287,301 B2, U.S. Appl. No. 16/010,081, Wiles et al., May 14, 2019.
US, U.S. Pat. No. 10,301,336 B2, U.S. Appl. No. 16/162,162, Wiles et al., May 28, 2019.
US, U.S. Pat. No. 10,428,095 B2, U.S. Appl. No. 16/148,622, Wiles et al., Oct. 1, 2019.
US, U.S. Pat. No. 10,464,956 B2, U.S. Appl. No. 16/276,139, Wiles et al., Nov. 5, 2019.
US, U.S. Pat. No. 10,370,394 B2, U.S. Appl. No. 15/638,081, Wiles et al., Aug. 6, 2019.
US, U.S. Pat. No. 10,385,097 B2, U.S. Appl. No. 15/247,410, Wiles et al., Aug. 20, 2019.
US, U.S. Pat. No. 10,428,094 B2, U.S. Appl. No. 15/638,076, Wiles et al., Oct. 1, 2019.
US, U.S. Pat. No. 10,550,140 B2, U.S. Appl. No. 16/164,632, Wiles et al., Feb. 4, 2020.
US, 2018/0177761 A1, U.S. Appl. No. 15/905,427, Wiles et al., Jun. 28, 2018.
US, 2018/0179236 A1, U.S. Appl. No. 15/905,504, Wiles et al., Jun. 28, 2018.
US, 2018/0179185 A1, U.S. Appl. No. 15/905,535, Wiles et al., Jun. 28, 2018.
US, 2018/0179186 A1, U.S. Appl. No. 15/905,524, Wiles et al., Jun. 28, 2018.
US, 2018/0186782 A1, U.S. Appl. No. 15/905,461, Wiles et al., Jul. 5, 2018.
US, 2018/0201580 A1, U.S. Appl. No. 15/905,537, Wiles et al., Jul. 19, 2018.
US, 2019/0038623 A1, U.S. Appl. No. 16/053,716, Huang et al., Feb. 7, 2019.
US, 2019/0048033 A1, U.S. Appl. No. 16/164,632, Wiles et al., Feb. 14, 2019.
US, 2019/0144473 A1, U.S. Appl. No. 16/246,832, Gadhachanda et al., May 16, 2019.
US, 2019/0211033 A1, U.S. Appl. No. 16/351,203, Wiles et al., Jul. 11, 2019.
US, 2019/0382376 A1, U.S. Appl. No. 16/555,946, Wiles et al., Dec. 19, 2019.
US, 2020/0002347 A1, U.S. Appl. No. 16/555,930, Wiles et al., Jan. 2, 2020.
US, 2020/0062790 A1, U.S. Appl. No. 16/672,114, Wiles et al., Feb. 27, 2020.
US, 2020/0071301 A1, U.S. Appl. No. 16/555,914, Wiles et al., Mar. 5, 2020.
Brodsky, "Eculizumab: another breakthrough" Blood. Feb. 23, 2017, vol. 129, No. 8.
DeZern et al.; "Paroxysmal Nocturnal Hemoglobinuria: A Complement-Mediated Hemolytic Anemia" Hematol Oncol Clin North Am. Jun. 2015 ; 29(3): 479-494. doi:10.1016/j.hoc.2015.01.005.
Gavriilaki et al., "275 Small molecule factor D inhibitors block complement activation in Paroxysmal Nocturnal Hemoglobinuria and atypical hemolytic uremic syndrome", 57th ASH Annual Meeting, Dec. 2015.
Le et al., "A Mechanistic Pharmacokinetic/Pharmacodynamic Model of Factor D Inhibition in Cynomolgus Monkeys by Lampalizumab for the Treatment of Geographic Atrophy" J. Pharmacol. Exp. Ther. 2015: 355: 288-296.
Mastellos et al.; "Complement in paroxysmal nocturnal hemoglobinuria: exploiting our current knowledge to improve the treatment landscape" Expert Rev Hematol. 2014; 7(5): 583-598.
NCT03472885—A Treatment Study of ACH-0144471 in Patients With Paroxysmal Nocturnal Hemoglobinuria (PNH) With Inadequate Response to Eculizumab (PNH), First Posted Mar. 15, 2018, available at: https://clinicaltrials.gov/ct2/show/NCT03472885.
Parker; "Update on the diagnosis and management of paroxysmal nocturnal hemoglobinuria" Hematology Am Soc Hematol Educ Program 2016; 2016 (1): 208-216. doi: https://doi.org/10.1182/asheducation-2016.1.208.
Ricklin et al.; "Complement in immune and inflammatory disorders: pathophysiological mechanisms" J Immunol. Apr. 15, 2013; 190(8): 3831-3838. doi:10.4049/jimmunol.1203487.
Risitano; "Paroxysmal nocturnal hemoglobinuria in the era of complement inhibition" American Journal of Hematology, vol. 91, No. 4, Apr. 2016 doi:10.1002/ajh.24323.
Risitano; "Anti-Complement Treatment in Paroxysmal Nocturnal Hemoglobinuria: Where we Stand and Where we are Going" Transl Med UniSa. Feb. 4, 2014; 8: 43-52. eCollection Jan. 2014.
Risitano and Marotta, "Toward complement inhibition 2.0: Next generation anticomplement agents for paroxysmal nocturnal hemoglobinuria" Am. J. Hematol. 2018; 93: 564-577. First published Jan. 4, 2018.
Risitano et al.; "Safety and Pharmacokinetics of the Complement Inhibitor TT30 in a Phase I Trial for Untreated PNH Patients" Blood 2015; 126 (23): 2137. doi: https://doi.org/10.1182/blood.V126.23.2137.2137.
Sica et al. Journal of Hematology & Oncology (2017) 10:126 DOI 10.1186/s13045-017-0496-x.
Yuan et al., "Small-molecule factor D inhibitors selectively block the alternative pathway of complement in paroxysmal nocturnal hemoglobinuria and atypical hemolytic uremic syndrome" Haematologica 2017, vol. 102(3): 466-475. Pre-published Nov. 3, 2016.
Harder et al., "Incomplete inhibition by eculizumab: mechanistic evidence for residual C5 activity during strong complement activation" Blood, 2017, 129:970.
International Search Report and Written Opinion for PCT/US2018/045057 mailed Nov. 15, 2018.
Patel et al., "In Vitro Combination Studies of ACH-4471 with Eculizumab to Assess a Potential 'Switch' Treatment Approach for Paroxysmal Nocturnal Hemoglobinuria" Poster, 2017.
Risitano et al., Blood, 2009, 113:4094.
Risitano et al., Blood, Mar. 27 2014; 123(13):2094-101.
U.S. Appl. No. 16/006,476, Wiles et al.
U.S. Appl. No. 16/006,533, Wiles et al.
Airey et al. "A Convenient Preparation of Thieno[3,2-c]pyrazole" Synthesis, 2014; 46: 96-100.
Babiker et al., PubMed Abstract (Am J Reprod Immunol. 47(3): 183-92), 2002.
Barraclough et al. "Synthesis of (2S,3R)- and (2S,3S)-[3-$^2$H$_1$]-proline via highly selective hydrolysis of a silyl enol ether," Tetrahedron Letters. 46(1): 4653-4655 (2005).
Barraclough et al. "Two separate and distinct syntheses of stereospecifically deuterated samples of (2S)-proline" Organic & Biomolecular Chemistry, 2006; 4: 1483-1491.
Borowitz et al., "Guidelines for the Diagnosis and Monitoring of Paroxysmal Nocturnal Hemoglobinuria and Related Disorders by Flow Cytometry," Cytometry Part B (Clinical Cytometry) 78B(4): 211-230, (2010).

(56) References Cited

OTHER PUBLICATIONS

Carter, "Complement Activation: An Emerging Player in the Pathogenesis of Cardiovascular Disease," Scientifica. 2012(1):1-14 (2012).
Cofiell et al., "Eculizumab reduces complement activation, inflammation, endothelial damage, thrombosis, and renal injury markers in aHUS," Blood 125(21):3253-62 (2015).
Cole et al. "Structure of 3,4-Dichloroisocoumarin-Inhibited Factor D," Acta Crystallogr D Biol Crystallogr, 54(Pt 5): 711-717 (1998).
Compound Summary for CID 1129904, PubChem. <https://pubchem.ncbi.nlm.nih.gov/compound/1129904>, entered Jul. 10, 2005 (10 pages).
Compound Summary for CID 59912842, PubChem, <https://pubchem.ncbi.nlm.nih.gov/compound/59912842>, entered Aug. 20, 2012 (9 pages).
Damasio, "Alzheimer's disease and related dementias," Cecil Textbook of Medicine, 20th Edition, vol. 2. Bennet and Plum, Jun. 1992 (1996).
Database Registry Chemical Abstracts Service, Columbus, Ohio, Accession No. RN1236248-20- 6, Entered STN: Aug. 16, 2010.
Database Registry Chemical Abstracts Service, Columbus, Ohio, Accession No. RN1380849-41-1, Entered STN: Jul. 3, 2012.
De Luca et al. "HIV-1 integrase strand-transfer inhibitors: Design, synthesis and molecular modeling investigation" Eur J Med Chem, 46(2): 756-764 (2011).
Donthiri et al., "Copper-Catalyzed C—H Functionalization of Pyridines and Isoquinolines with Vinyl Azides: Synthesis of Imidazo Heterocycles," J Org Chem, 79(22): 11277-11284 (2014).
Dormoy et al., "Synthesis of N-t-Butoxycarbonyl-4,4-dideuterio-L-proline," Synthesis, 1: 81-82 (1986).
Gura, "Systems for identifying new drugs are often faulty," Science. 278(5340):1041-2 (1997).
Hartmann et al., "Diagnostic Specificity of Sucrose Hemolysis Test for Paroxysmal Nocturnal Hemoglobinuria," Blood. 35(4):462-475, (1970).
Hecker et al., "Liver-Targeted Prodrugs of 2'-C-Methyladenosine for Therapy of Hepatitis C Virus Infection," J Med Chem, 50(16): 3891-3896 (2007).
Hruby et al., "Carbon-13 NMR studies of the Peptide hormones oxytocin, arginine vasopressin, isotocin, mesotocin, glumitocin, aspartocin, related analogs, and diastereoisomers. Use of specifically deuterated hormone derivatives for assignments andeffects of structural changes on carbon-13 NMR chemical shifts in peptides," Journal of the American Chemical Society, 101(1): 202-212 (1979).
International Search Report and Written Opinion for PCT/US2015/017523 dated May 14, 2015.
International Search Report and Written Opinion for PCT/US2015/017538 dated May 14, 2015.
International Search Report and Written Opinion for PCT/US2015/017554 dated May 14, 2015.
International Search Report and Written Opinion for PCT/US2015/017583 dated May 27, 2015.
International Search Report and Written Opinion for PCT/US2015/017593 dated Jun. 16, 2015.
International Search Report and Written Opinion for PCT/US2015/017597 dated Jan. 29, 2016.
International Search Report and Written Opinion for PCT/US2015/017609 dated May 29, 2015.
International Search Report and Written Opinion for PCT/US2015/17600 dated May 27, 2015.
International Search Report and Written Opinion for PCT/US2016/048688 dated Dec. 28, 2016.
International Search Report and Written Opinion for PCT/US2016/048690 dated Dec. 28, 2016.
International Search Report and Written Opinion for PCT/US2016/048693 dated Jan. 13, 2017.
International Search Report and Written Opinion for PCT/US2016/048695 dated Dec. 30, 2016.
International Search Report and Written Opinion for PCT/US2016/048696 dated Jan. 5, 2017.
International Search Report and Written Opinion for PCT/US2016/048701 dated Jan. 10, 2017.
International Search Report and Written Opinion for PCT/US2016/048704 dated Dec. 27, 2016.
International Search Report and Written Opinion for PCT/US2016/048707 dated Jan. 5, 2017.
International Search Report and Written Opinion for PCT/US2016/048709 dated Jan. 17, 2017.
International Search Report and Written Opinion for PCT/US2016/048710 dated Jan. 5, 2017.
International Search Report and Written Opinion for PCT/US2016/048779 dated Dec. 27, 2016.
International Search Report and Written Opinion for PCT/US2016/048783 dated Feb. 3, 2017.
International Search Report and Written Opinion for PCT/US2016/048787 dated Jan. 5, 2017.
International Search Report and Written Opinion for PCT/US2016/048788 dated Jan. 5, 2017.
International Search Report and Written Opinion for PCT/US2016/048793 dated Dec. 28, 2016.
International Search Report and Written Opinion for PCT/US2016/048795 dated Feb. 17, 2017.
International Search Report and Written Opinion for PCT/US2016/048797 dated Jan. 5, 2017.
International Search Report and Written Opinion for PCT/US2016/048799 dated Dec. 28, 2016.
International Search Report and Written Opinion for PCT/US2016/048800 dated Jan. 5, 2017.
International Search Report for International Application No. PCT/US2019/034210, mailed Sep. 13, 2019 (4 pages).
International Search Report for International Application No. PCT/US2019/050073, mailed Nov. 21, 2019 (3 pages).
Johnson et al., "Relationships between drug activity in NCI preclinical in vitro and in vivo models and early clinical trials," Br J Cancer. 84(10):1424-31 (2001).
Józsi, "Anti-Complement Autoantibodies in Membranoproliferative Glomerulonephritis and Dense Deposit Disease", An Update on Glomerulopathies—Etiology and Pathogenesis. Prof. Sharma Prabhakar, 11-46 (2011).
Kobayashi et al. "Carboxylation of alkynylsilanes with carbon dioxide mediated by cesium fluoride in DMSO," Org Biomol Chem. 11:3773-3775 (2013).
Komiya et al., CAplus Database Summary Sheet for Document No. 162:229476, Acession No. 2015:126147, CAplus on STN. (2015) (2 pages).
Krauss, "Laboratory Diagnosis of Paroxysmal Nocturnal Hemoglobinuria," Annals of Clinical & Laboratory Science. 33(4): 401-406, (2003).
Kuang et al. "Synthesis of (Z)-1-bromo-1-alkenes and terminal alkynes from anti-2,3-dibromoalkanoic acids by microwave-induced reaction," Tetrahedron. 61(16):4043-4052 (2005).
Lassmann. "What drives disease in multiple sclerosis: Inflammation or neurodegeneration?" Clinical and Experimental Neuroimmunology. 1:2-11 (2010).
Layzer, "Degenerative Diseases of the Nervous System", Cecil Textbook of Medicine, 20th Edition, Vo. 2, pp. 2050-2057 (1996).
MacKay et al., "Rapid Synthesis of the N-Methylwelwitindolinone Skeleton," Org Lett. 7(16):3421-4 (2005).
Noris et al. "Overview of Complement Activation and Regulation," Semin Nephrol. 33:479-492 (2013).
Okutani et al. "Conversion of Bromoalkenes into Alkynes by Wet Tetra-n-butylammonium Fluoride," J Org Chem. 74(1):442-444 (2009).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Qu et al., "Recent Developments in Low Molecular Weight Complement Inhibitors," Mol Immunol. 47(2-3):185-195 (2009).
Quesada et al. "One-pot conversion of activated alcohols into terminal alkynes using manganese dioxide in combination with the Bestmann—Ohira reagent," Tetrahedron Letters. 46:6473-6476 (2005).

(56) References Cited

OTHER PUBLICATIONS

Rohrer et al., "Eliminating complement factor D reduces photoreceptor susceptibility to light-induced damage," Invest Ophthalmol Vis Sci. 48(11):5282-9 (2007).
Roth et al. "Further Improvements of the Synthesis of Alkynes from Aldehydes," Synthesis. 1:59-62 (2004).
Ruiz-Gómez et al. "Structure-Activity Relationships for Substrate-Based Inhibitors of Human Complement Factor B," J Med Chem. 52(19):6042-6052 (2009).
Simone, "Oncology: Introduction," Cecil Textbook of Medicine, 20th Edition, vol. 1, pp. 1004-1010, (1996).
Stanton et al. "Complement Factor D in Age-Related Macular Degeneration," Invest Ophthalmol Vis Sci. 52(12):8828-8834 (2011) (15 pages).
Strobel et al., "Anti-factor B autoantibody in dense deposit disease," Mol Immunol. 47(7-8):1476-1483 (2010).
Tandon et al., "Substrate specificity of human prolyl-4-hydroxylase," Bioorg Med Chem Lett. 8(10):1139-1144 (1998).
Tang et al. "Palladium-Catalyzed Carbonylative Sonogashira Coupling of Aryl Bromides via tert-Butyl Isocyanide Insertion," J Org Chem. 78(7):3170-3175 (2013).
Wehling et al., "Monitoring of complement activation biomarkers and eculizumab in complement-mediated renal disorders," Clin Exp Immunol. 187(2):304-15 (2017).
What is Dementia?[online] retrieved from the internet on Sep. 4, 2018. URL; https://www.alz.org/alzheimers-dementia/ what-is-dementia.
Written Opinion for International Application No. PCT/US2019/034210, mailed Sep. 13, 2019 (17 pages).
Written Opinion for International Application No. PCT/US2019/050073, mailed Nov. 21, 2019 (4 pages).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available <https://library.ehaweb.org/eha/2016/21st/135361/roderick.b.ellis-pegler.an.orally.administered.small.molecule.factor.d.html> (2016) (2 pages).
Ellis-Pegler et al., "An Orally Administered Small Molecule Factor D Inhibitor (ACH-4471) For Treatment of PNH, C3G and Complement-Mediated Diseases: Interim Phase 1 Results In Healthy Volunteers," European Hematology Association, Copenhagen 21st Congress, Jun. 9-12, Abstract ID: EHA-4145 (2016).
Extended European Search Report for European Application No. 18840849.6, dated Mar. 17, 2021 (11 pages).

Konar et al., "Eculizumab treatment and impaired opsonophagocytic killing of meningococci by whole blood from immunized adults," Blood. 130(7):891-9 (2017).
"Patient Information for TARPEYO (tar-PAY-oh) (budesonide) delayed release capsules," Calliditas Therapeutics AB, Dec. 2021 (2 pages).
Andrighetto et al., "Complement and Complement Targeting Therapies in Glomerular Diseases," Int J Mol Sci. 20(24):6336 (Dec. 2019), available <https://www.ncbi.nlm.nih.gov/pmc/articles/PMC6940904/>, retrieved on May 26, 2022 (21 pages).
Extended European Search Report for European Application No. 19857780.1, dated May 13, 2022 (9 pages).
Extended European Search Report for European Application No. 19897806.6, dated Jul. 18, 2022 (12 pages).
Gilkeson, "Complement-Targeted Therapies in Lupus," Curr Treat Options in Rheum. 1:10-18 (Jan. 22, 2015).
Harris et al., "Developments in anti-complement therapy; from disease to clinical trial," Mol Immunol. 102:89-119 (Oct. 2018).
Hom et al., "Complement Inhibitors for Treatment of Geographic Atrophy and Advanced Nonexudative AMD," Retinal Physician. 16:28-31 (Mar. 1, 2019) (7 pages).
Iatropoulos et al., "Cluster Analysis Identifies Distinct Pathogenetic Patterns in C3 Glomerulopathies/Immune Complex-Mediated Membranoproliferative GN," J Am Soc Nephrol. 29(1):283-94 (with supplemental material) (Jan. 2018) (36 pages).
International Preliminary Report on Patentability for International Application No. PCT/US2021/018871, mailed Sep. 1, 2022 (6 pages).
Mantegazza et al., "Complement Inhibition for the Treatment of Myasthenia Gravis," Immunotargets Ther. 9:317-31 (Dec. 2020), <https://www.ncbi.nlm.nih.gov/pmc/articles/PMC7751298/>, retrieved on May 26, 2022 (24 pages).
Marinozzi et al., "C5 nephritic factors drive the biological phenotype of C3 glomerulopathies," Kidney Int. 92(5):1232-41 (Nov. 2017).
Michels et al., "Long-term follow-up including extensive complement analysis of a pediatric C3 glomerulopathy cohort," Pediatr Nephrol. 37(3):601-12 (Mar. 2022).
Partial Supplementary European Search Report for European Application No. 19857913.8, dated Apr. 13, 2022 (17 pages).
Risitano et al., "Danicopan: an oral complement factor D inhibitor for paroxysmal nocturnal hemoglobinuria," Haematologica. 106(12):3188-97 (Dec. 1, 2021).
Varelas et al., "Complement in Sickle Cell Disease: Are We Ready for Prime Time?," J Blood Med. 12:177-87 (2021), <https://www.ncbi.nlm.nih.gov/pmc/articles/PMC8001680/>, dated Mar. 23, 2021, retrieved on May 26, 2022 (19 pages).
Willows et al., "The role of complement in kidney disease," Clin Med (Lond). 20(2):156-60 (Mar. 2020) (9 pages).
Zhang et al., "Defining the complement biomarker profile of C3 glomerulopathy," Clin J Am Soc Nephrol. 9(11):1876-82 (supplemental materials) (Nov. 7, 2014) (10 pages).

\* cited by examiner

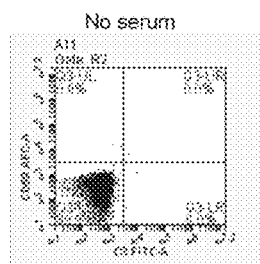 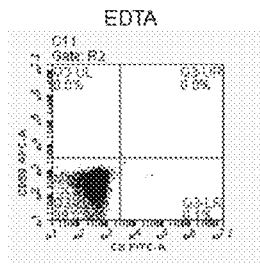 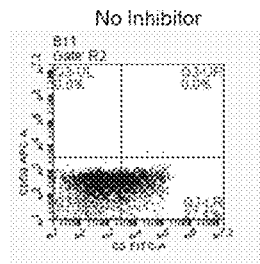 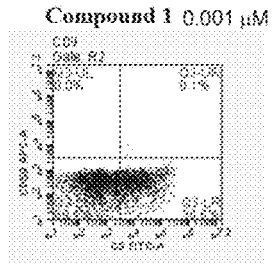
FIG. 7A    FIG. 7B    FIG. 7C    FIG. 7D
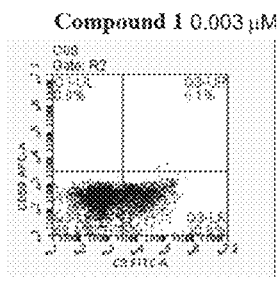 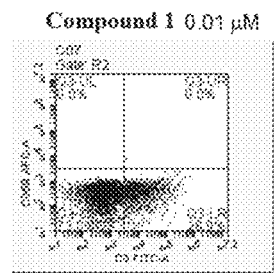 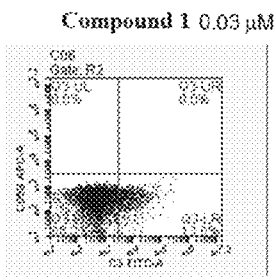 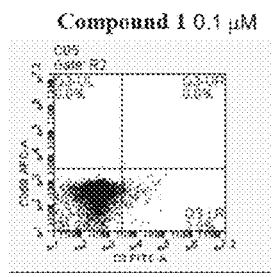
FIG. 7E    FIG. 7F    FIG. 7G    FIG. 7H
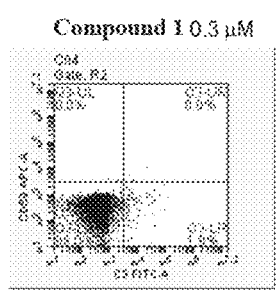 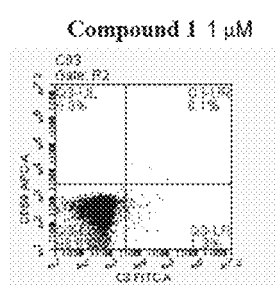 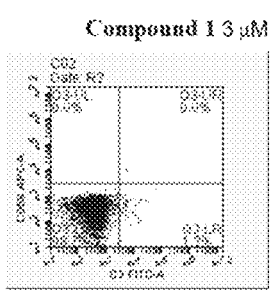 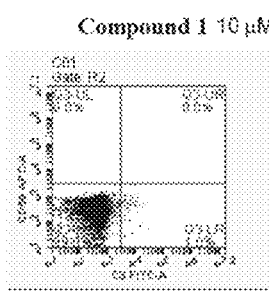
FIG. 7I    FIG. 7J    FIG. 7K    FIG. 7L

THERAPEUTIC REGIMENS FOR TREATMENT OF PAROXYSMAL NOCTURNAL HEMOGLOBINURIA

STATEMENT OF RELATED APPLICATIONS

This application is a continuation application of U.S. application Ser. No. 16/053,716, filed Aug. 2, 2018, which claims the benefit of U.S. Provisional Application No. 62/540,451, filed on Aug. 2, 2017, and U.S. Provisional Application No. 62/593,669, filed Dec. 1, 2017. The entirety of each of these applications is incorporated herein by reference for all purposes.

FIELD OF THE INVENTION

This invention is in the area of therapeutic regimens for the treatment of the complement-mediated disorder paroxysmal nocturnal hemoglobinuria (PNH).

BACKGROUND OF THE INVENTION

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within C3 to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

Paroxysmal nocturnal hemoglobinuria (PNH) is a clonal hematopoietic stem cell (HSC) disease that presents with hemolytic anemia, thrombosis, and smooth muscle dystonia, as well as bone marrow failure in some cases. PNH is caused by somatic mutations in PIGA (which encodes phosphatidylinositol N-acetylglucosaminyltransferase subunit A) in one or more HSC clones. The gene product of PIGA is required for the biosynthesis of glycosylphosphatidylinositol (GPI) anchors; thus, PIGA mutations lead to a deficiency of GPI-anchored proteins, such as complement decay-accelerating factor (also known as CD55) and CD59 glycoprotein (CD59), which are both complement inhibitors. The loss of CD55 and CD59 renders PNH erythrocytes susceptible to destructive C3 convertase and terminal complex assembly on their membranes following normal slow AP activation ("tickover") in the fluid phase, resulting in intravascular hemolysis, which can lead to thrombosis and much of the morbidity and mortality associated with PNH.

Eculizumab (SOLARIS, Alexion Pharmaceuticals, Inc.), a monoclonal antibody complement inhibitor, is the only approved therapy for PNH. As an inhibitor of the terminal component C5, eculizumab blocks assembly of the hemolytic terminal complex (also known as membrane attack complex, MAC). C5 blockade by eculizumab prevents complement-mediated intravascular hemolysis in PNH. Eculizumab treatment, however, leads to increased deposition of complement C3 fragments on PNH membranes, which can result in extravascular phagocytic elimination of opsonized erythrocytes in the spleen and the liver (A. M. Risitano et al, Blood, 2009, 113:4094) and incomplete inhibition of intravascular hemolysis (M. J. Harder et al, Blood, 2017, 129:970), and consequently to the continued anemia and transfusion dependence observed in a significant subset of subjects. Approximately 30% of patients on eculizumab continue to have severe anemia due to ongoing extravascular hemolysis.

Suboptimal inhibition of hemolysis, both intravascular and extravascular, remains a major problem in treating PNH. It is an object of the present invention to provide improved methods and treatments which sufficiently inhibit intravascular and extravascular hemolysis of PNH erythrocytes. It is a further object of the present invention to inhibit or reduce the deposition of C3 fragments on PNH erythrocytes. It is further object of the present invention to improve the efficacy of complement inhibitor therapy for the treatment of PNH.

SUMMARY OF THE INVENTION

Provided herein are methods for treating a subject with PNH comprising administering to a subject a therapeutically effective amount of complement component C5 (C5) inhibitor, complement component C3 (C3) inhibitor, or complement factor B (CFB) inhibitor in combination with a therapeutically effective amount of small molecule complement factor D (CFD) inhibitor. By including a CFD inhibitor described herein in combination with, or following administration of, a C5 inhibitor, C3 inhibitor, or a CFB inhibitor, significant improvement in the inhibition of intravascular hemolysis associated with PNH is attained. Furthermore, by including a CFD inhibitor in the therapeutic regimen, prohibition of the upstream C3 convertase assembly and C3 fragment deposition contributing to extravascular hemolysis associated with the clinical use of C5 inhibitors alone, for example eculizumab, is achieved. In addition, by including a CFD inhibitor described herein in combination with, or following administration of, a C3 inhibitor, or a CFB inhibitor, significant improvement in the inhibition of the upstream C3 convertase assembly and C3 fragment deposition contributing to extravascular hemolysis associated with PNH is attained.

It has been surprisingly found that the use of CFD inhibitor described herein in combination with a C5 inhibitor or C3 inhibitor synergistically enhances inhibition of hemolysis. By including a CFD inhibitor described herein in a therapeutic protocol, an improved treatment regimen is provided for subjects with PNH who experience incomplete intravascular hemolysis inhibition with a C5 inhibitor or C3 inhibitor treatment alone. Accordingly, the inclusion of a CFD inhibitor described herein in the treatment regimen acts as an effective salvage therapy and drastically extends the therapeutic effectiveness of the C5 and/or C3 inhibitor.

It has also been found that the use of a CFD inhibitor described herein in combination with a C5 inhibitor synergistically enhances inhibition of hemolysis, including C3-fragment deposition induced hemolysis associated with extravascular hemolysis in PNH, a major complication associated with the clinical use of standard of care C5 inhibitor treatments such as eculizumab. The clinical use of, for example, the C5 inhibitor eculizumab has been associated with the development of extravascular hemolysis through C3-fragment deposition and, in certain subpopulations, an incomplete inhibition of intravascular hemolysis. As shown in the examples below, the use of a CFD inhibitor described herein inhibits the membrane deposition of C3 fragments on PNH erythrocytes. By incorporating a CFD inhibitor described herein in combination with, for example, eculizumab both MAC assembly and C3 fragment deposition on PNH erythrocytes can be inhibited. Therefore, the combination of a CFD inhibitor described herein and a C5 inhibitor, for example eculizumab, provides an improved therapeutic approach to treat PNH subjects who are suboptimal responders to a C5 inhibitor and/or subject to extravascular hemolysis.

It is believed that the use of a CFD inhibitor described herein reduces the density of deposited C3b clusters, to which C5 binding is thereby more readily inhibited by a C5 inhibitor, for example eculizumab. While eculizumab binds to C5 and blocks the terminal pathway of complement upstream of CD59, it does not address the deposition of C3 fragments as a result of the complement alternative pathway due to the absence of CD55 on PNH erythrocytes. As a result, PNH erythrocytes accumulate C3 fragment and are susceptible to extravascular hemolysis by opsonization. In contrast, inclusion of a CFD inhibitor described herein inhibits both complement terminal pathway activation as well as opsonization, complementing in a synergistic fashion the effects of C5 inhibitors.

Accordingly, in one aspect, the present invention provides methods for treating a subject with PNH comprising administering to the subject a therapeutically effective amount of a C5 inhibitor, a C3 inhibitor, a CFB inhibitor or a pan-inhibitor to complement components in combination with a therapeutically effective amount of a CFD inhibitor described herein.

Factor D inhibitors for use in the present invention are described herein. In one aspect, a CFD inhibitor of Formula I may be used:

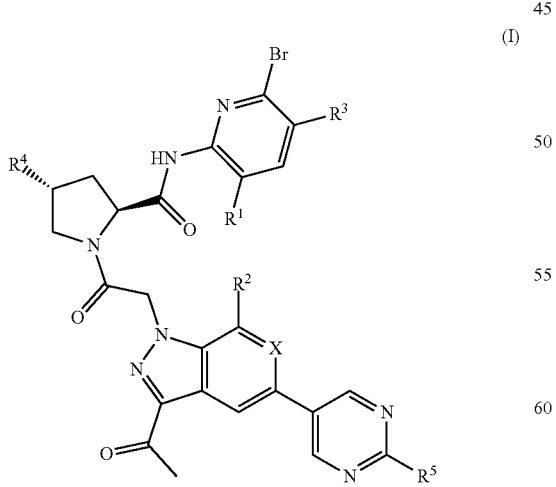

(I)

or a pharmaceutically acceptable salt, N-oxide, isotopic derivative, or prodrug thereof, optionally in a pharmaceutically acceptable carrier to form a composition;

wherein:

X is selected from N and CH;

$R^1$ is selected from hydrogen, $C_1$-$C_3$ alkyl, and halogen;

$R^2$ is selected from hydrogen and $C_1$-$C_3$ alkyl;

$R^3$ is selected from hydrogen, $C_1$-$C_3$ alkyl, and halogen;

$R^4$ is selected from hydrogen, $C_1$-$C_3$ alkyl, and halogen; and $R^5$ is selected from hydrogen, $C_1$-$C_3$ alkyl, halogen, and cyano.

In one embodiment, the compound of Formula I is selected from:

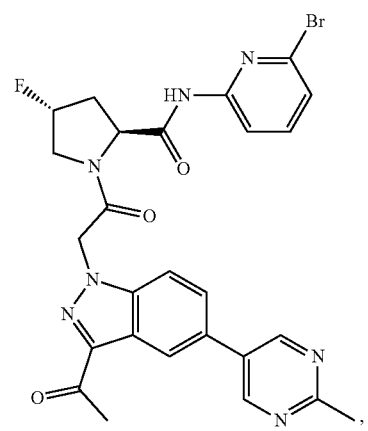

1

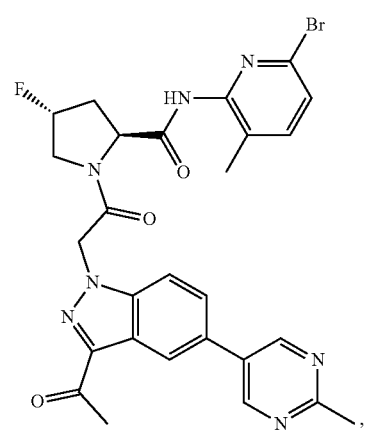

2

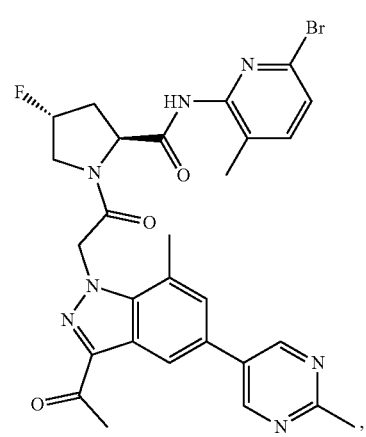

3

4
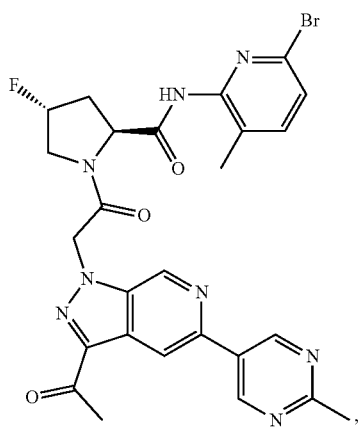
5
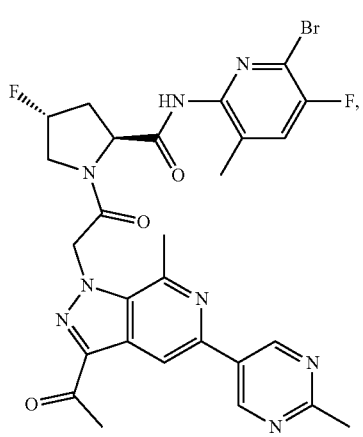
6
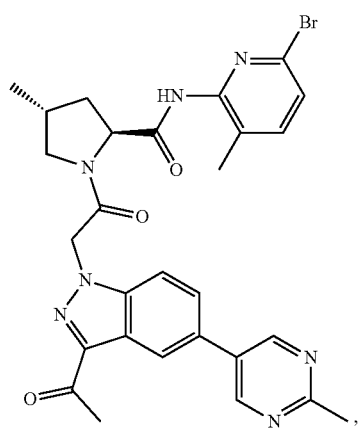
7
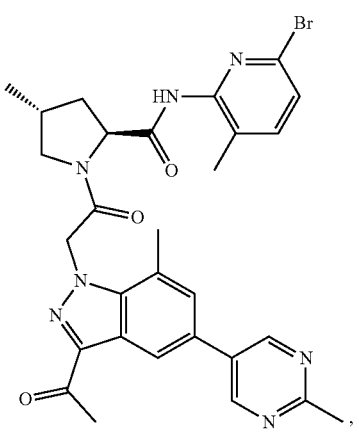
8
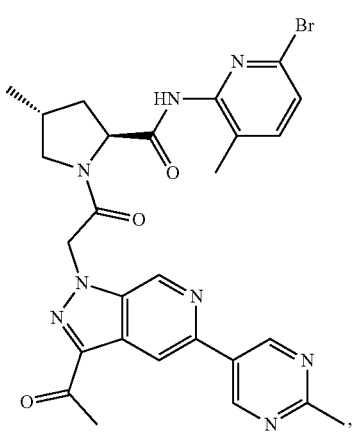
9
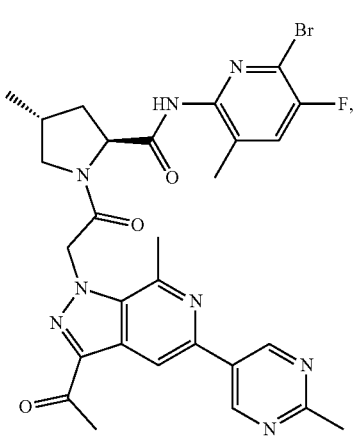

10

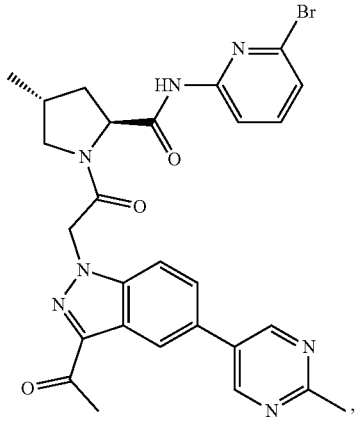

11

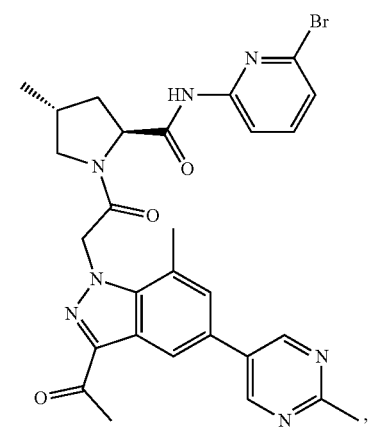

12

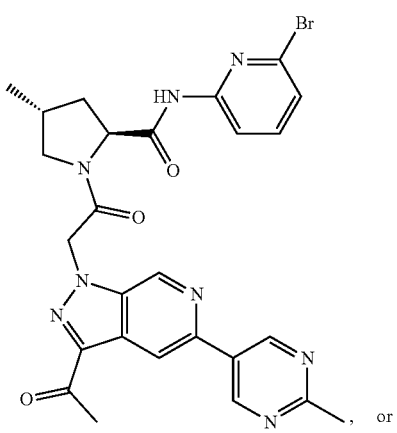

or

13

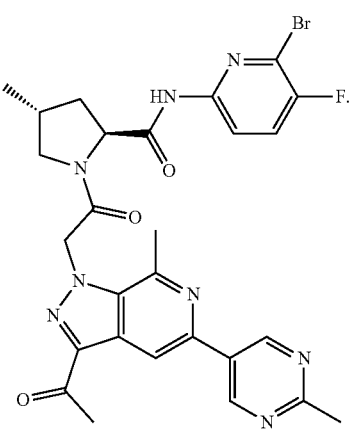

In an alternative aspect, a CFD inhibitor of Formula II may be used:

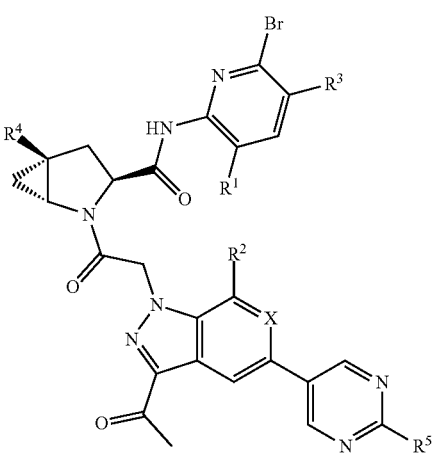

(II)

or a pharmaceutically acceptable salt, N-oxide, isotopic derivative, or prodrug thereof, optionally in a pharmaceutically acceptable carrier to form a composition;

wherein:

X is selected from N and CH;

$R^1$ is selected from hydrogen, $C_1$-$C_3$ alkyl, and halogen;

$R^2$ is selected from hydrogen and $C_1$-$C_3$ alkyl;

$R^3$ is selected from hydrogen, $C_1$-$C_3$ alkyl, and halogen;

$R^4$ is selected from hydrogen, $C_1$-$C_3$ alkyl, and halogen; and $R^5$ is selected from hydrogen, $C_1$-$C_3$ alkyl, halogen, and cyano.

In one embodiment, the compound of Formula II is selected from:

14
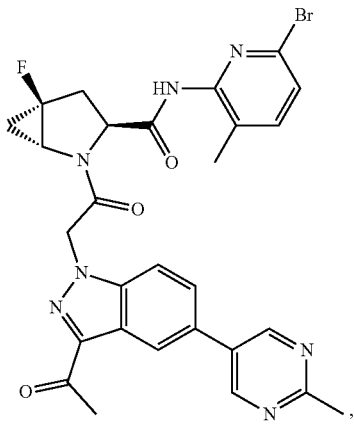
15
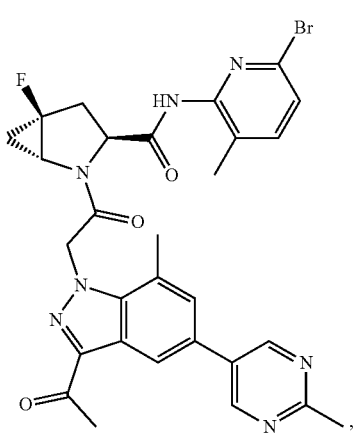
16
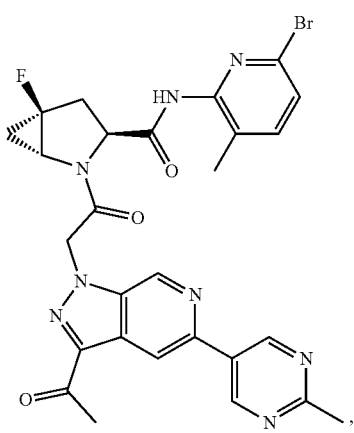
17
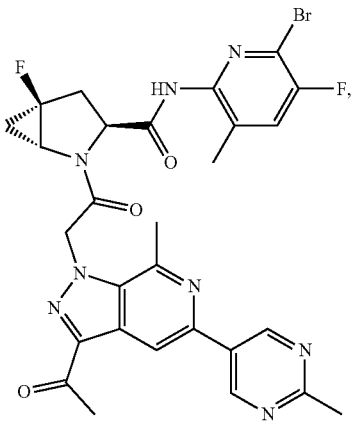
18
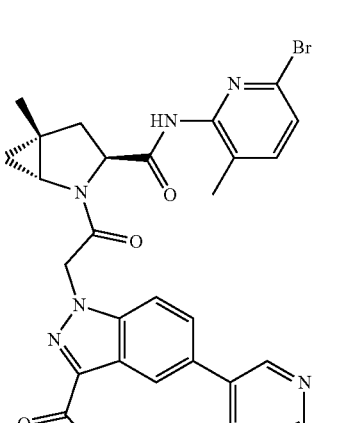
19
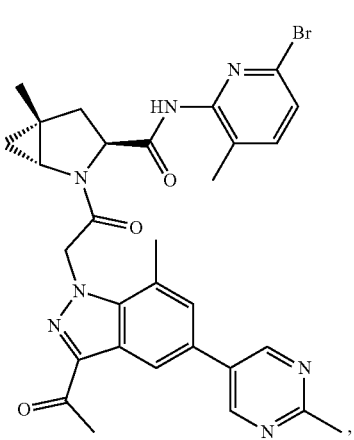

20

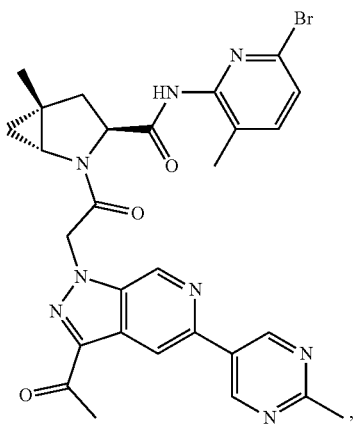

21

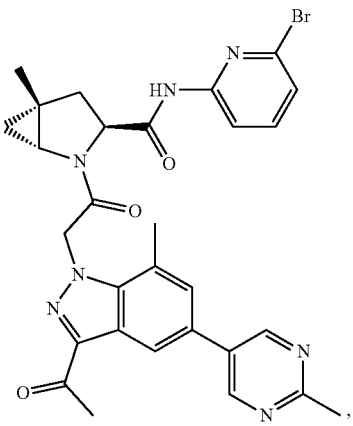

22

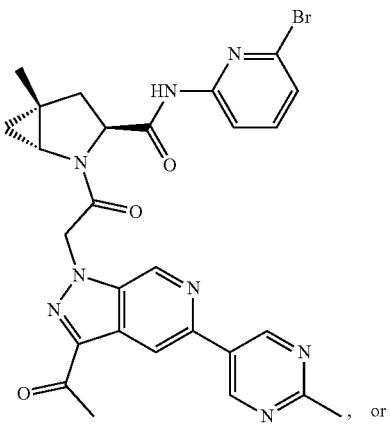

23

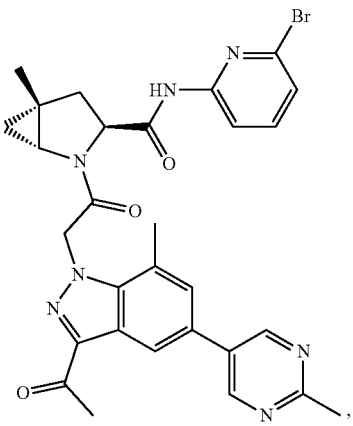

24

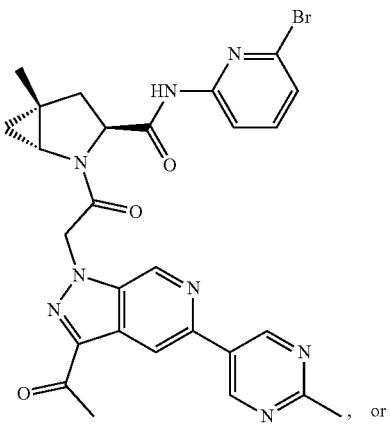

, or

25

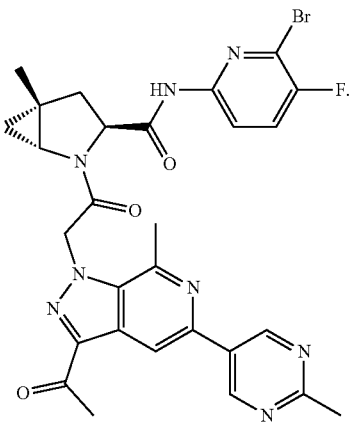

In one aspect, provided herein is a method of treating a subject with PNH comprising administering to the subject a therapeutically effective amount of a C5 inhibitor in combination or alternation with a therapeutically effective amount of a CFD inhibitor selected from Formula I or Formula II, or a pharmaceutically acceptable salt thereof. In a particular embodiment, the C5 inhibitor is a monoclonal antibody to C5. In one embodiment, the C5 inhibitor is eculizumab. Other C5 inhibitors for use in the methods described herein include, but are not limited to: a recombinant human minibody, for example Mubodina® (Adienne Pharma and Biotech); coversin (Akari Therapeutics); Tesidolumab/LFG316 (Novartis/Morphosys); ARC-1905 (Ophthotech); RA101348 (Ra Pharmaceuticals); RA101495 (Ra Pharmaceuticals); SOBI002 (Swedish Orphan Biovitrum);

ARC1005 (Novo Nordisk); a SOMAmer for C5 (SomaLogic); SSL7; MEDI7814 (MedImmune); aurin tricarboxylic acid (Aurin Biotech); an aurin tricarboxylic acid derivative (Aurin Biotech); RG6107/SKY59 (Roche Pharmaceuticals); ALXN1210 (Alexion Pharmaceuticals); ALXN5500 (Alexion Pharmaceuticals); TT30 (Alexion Pharmaceuticals); ABP959 (Amgen); Anti-C5 siRNA (Alnylam Pharmaceuticals); Erdigna (Adienne Pharma); avacincaptad pegol/Zimura® (Ophthotech); SOBI005 (Swedish Orphan Biovitrum); ISU305 (ISU ABXIS); and REGN3918 (Regeneron). In one embodiment, the C5 inhibitor is eculizumab, and the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25. In one embodiment, the subject has a genetic polymorphism in Complement Receptor 1 gene (CR1). In one embodiment, the CR1 polymorphism is HindIII H/L or L/L genotype (see, for example, Rondelli et al., Polymorphism of the complement receptor 1 gene correlates with the hematologic response to eculizumab in patients with paroxysmal nocturnal hemoglobinuria, Haematologica. 2014 February; 99(2): 262-266, incorporated herein by reference).

In one aspect, provided herein is a method of treating a subject with PNH comprising administering to the subject a CFD inhibitor selected from Formula I or Formula II, or a pharmaceutically acceptable salt thereof, wherein the subject at the time of administration of the CFD inhibitor has been or is currently receiving a therapeutic regimen comprising the administration of a C5 inhibitor and is experiencing extravascular hemolysis or residual intravascular hemolysis. Subjects receiving a C5 inhibitor who develop extravascular hemolysis may remain or become anemic, that is, have a hemoglobin level of less than about 12 g/dL, and more particularly less than about 10 g/dL, while maintaining, for example, normalized or slightly elevated lactate dehydrogenase (LDH) levels, for example LDH levels of less than about 250 U/L. Comparatively, subjects receiving a C5 inhibitor suffering from incomplete inhibition or residual intravascular hemolysis remain anemic, and may also have elevated LDH levels, for example an LDH levels 1.0× upper limit of normal (ULN) or greater. In a particular embodiment, upon administration of the CFD inhibitor, the C5 inhibitor also continues to be administered. In an alternative embodiment, upon administration of the CFD inhibitor, the C5 inhibitor is no longer administered. In a particular embodiment, the C5 inhibitor is a monoclonal antibody to C5. In one embodiment, the C5 inhibitor is eculizumab, and the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25. In one embodiment, the subject has been on a C5 therapeutic regimen for at least 3-months prior to administration of the CFD inhibitor.

In one aspect of the present invention, provided herein is a method of treating a subject with PNH comprising administering to the subject an effective amount of a CFD inhibitor selected from a compound of Formula I or Formula II, or a pharmaceutically acceptable salt therein, wherein, at the time of the administration of the CFD inhibitor, the subject has been or is currently receiving a therapeutic regimen comprising the administration of a C5 inhibitor, and wherein the subject has a Hgb level of less than about 12 g/dL. In one embodiment, the subject has a Hgb of less than about 10 g/dL. In one embodiment, the subject has a Hgb of less than about 8 g/dL. In one embodiment, at the time of administration of the CFD inhibitor, the subject is blood transfusion dependent. In one embodiment, the subject, at the time of administration of the CFD inhibitor, has received one or more blood transfusions within the prior twelve months. In one embodiment, the subject has received two or more blood transfusions with in the prior six months. In one embodiment, the subject has been on a C5 therapeutic regimen for at least 3-months prior to administration of the CFD inhibitor. In a particular embodiment, upon administration of the CFD inhibitor, the C5 inhibitor also continues to be administered. In an alternative embodiment, upon administration of the CFD inhibitor, the C5 inhibitor is no longer administered. In a particular embodiment, the C5 inhibitor is a monoclonal antibody to C5. In one embodiment, the C5 inhibitor is eculizumab, and the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25. In one embodiment, the subject has been on a C5 therapeutic regimen for at least 3-months prior to administration of the CFD inhibitor.

In one aspect of the present invention, provided herein is a method of treating a subject with PNH comprising administering to the subject an effective amount of a CFD inhibitor selected from a compound of Formula I or Formula II, or a pharmaceutically acceptable salt therein, wherein, at the time of the administration of the CFD inhibitor, the subject has been or is currently receiving a therapeutic regimen comprising the administration of a C5 inhibitor, and wherein the subject has a Hgb level of less than about 12 g/dL and an LDH level greater than 1.0×ULN. In one embodiment, the subject has a Hgb of less than about 10 g/dL. In one embodiment, the subject has a Hgb of less than about 8 g/dL. In one embodiment, the subject has an LDH level greater than 1.0×ULN. In one embodiment, the subject, at the time of administration of the CFD inhibitor, has received one or more blood transfusions within the prior twelve months. In one embodiment, the subject has received two or more blood transfusions with in the prior six months. In one embodiment, the subject has been on a C5 therapeutic regimen for at least 3-months prior to administration of the CFD inhibitor. In a particular embodiment, upon administration of the CFD inhibitor, the C5 inhibitor also continues to be administered. In an alternative embodiment, upon administration of the CFD inhibitor, the C5 inhibitor is no longer administered. In a particular embodiment, the C5 inhibitor is a monoclonal antibody to C5. In one embodiment, the C5 inhibitor is eculizumab, and the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25. In one embodiment, the subject has been on a C5 therapeutic regimen for at least 3-months prior to administration of the CFD inhibitor.

In one aspect of the present invention, provided herein is a method of treating a subject with PNH comprising administering to the subject an effective amount of a CFD inhibitor selected from a compound of Formula I or Formula II, or a pharmaceutically acceptable salt therein, wherein, at the time of the administration of the CFD inhibitor, the subject has been or is currently receiving a therapeutic regimen comprising the administration of a C5 inhibitor, and wherein the subject has a Hgb level of less than about 12 g/dL and an LDH level less than about 0.25×ULN. In one embodiment, the subject has a Hgb of less than about 10 g/dL. In one embodiment, the subject has a Hgb of less than about 8 g/dL. In one embodiment, the subject has an LDH level within a normal range. In one embodiment, the subject, at the time of administration of the CFD inhibitor, has received one or more blood transfusions within the prior twelve months. In one embodiment, the subject has received two or more blood transfusions with in the prior six months. In one embodiment, the subject has been on a C5 therapeutic regimen for at least 3-months prior to administration of the CFD inhibitor. In a particular embodiment, upon administration of the CFD inhibitor, the C5 inhibitor also continues to be administered. In an alternative embodiment, upon administration of the CFD inhibitor, the C5 inhibitor is no longer administered. In a particular embodiment, the C5 inhibitor is a monoclonal antibody to C5. In one embodiment, the C5 inhibitor is eculizumab, and the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25. In one embodiment, the subject has been on a C5 therapeutic regimen for at least 3-months prior to administration of the CFD inhibitor.

Also provided herein is a method of treating a subject with PNH comprising administering to the subject a therapeutically effective amount of a CFD inhibitor selected from Formula I or Formula II in combination with a C3 inhibitor. As described further below, the use of a CFD inhibitor selected from Formula I or Formula II in combination with a complement component C3 inhibitor also provides for synergistic inhibition of hemolysis of PNH erythrocytes. These synergistic effects provide for increased therapeutic efficacy in the treatment of PNH, while reducing the required amount of inhibitor necessary for therapeutic efficacy. In a particular embodiment, the C3 inhibitor is selected from compstatin or a compstatin analog or derivative. In a particular embodiment, the C3 inhibitor is compstatin. In a particular embodiment, the C3 inhibitor is the compstatin analog 4(1MeW)/APL-1. In a particular embodiment, the C3 inhibitor is the compstatin analog CP-40/AMY-101. In a particular embodiment, the C3 inhibitor is the compstatin analog Peg-CP-40. 4(1MeW)/APL-1, CP40/AMY-101, and Peg-CP-40 are described in Risitano, Ricklin et al., Peptide inhibitors of C3 activation as a novel strategy of complement inhibition for the treatment of paroxysmal nocturnal hemoglobinuria, Blood. 2014 Mar. 27; 123(13):2094-101, incorporated herein by reference. In a particular embodiment, the C3 inhibitor is AMY-201 (Amyndas Pharmaceuticals). In a particular embodiment, the C3 inhibitor is APL-2 (Apellis Pharmaceuticals). In a particular embodiment, the C3 inhibitor is ATA (aurin tricarboxylic acid) (Aurin Biotech, US Pat Appl Pub US20130035392, incorporated herein by reference). In one embodiment, the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25.

Further provided herein is a method of treating a subject with PNH comprising administering to the subject a therapeutically effective amount of a CFD inhibitor selected from Formula I or Formula II in combination with a complement factor B inhibitor. By targeting multiple mechanisms of complement inhibition, it is believed that the use of a CFD inhibitor selected from a compound of Formula I or Formula II in combination with a factor B inhibitor provides for improved inhibition of hemolysis of PNH erythrocytes, allowing for increased therapeutic efficacy in the treatment of PNH, while reducing the required amount of inhibitor necessary for therapeutic efficacy. In a particular embodiment, the CFB inhibitor is LNP023 (Novartis). In a particular embodiment, the CFB inhibitor is selected from an inhibitor described in WO2013/192345, incorporated by reference herein. In a particular embodiment, the CFB inhibitor is

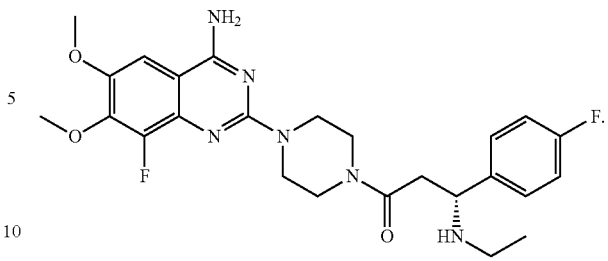

In a particular embodiment, the CFB inhibitor is selected from an inhibitor described in International Application No. PCT/US17/39587, incorporated herein by reference. In one embodiment, the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25.

In a further aspect, provided herein is a method of treating a subject with PNH comprising administering to the subject a therapeutically effective amount of a CFD inhibitor selected from Formula I or Formula II in combination with a pan-inhibitor to complement components. In one embodiment, the inhibitor is FUT-175. In one embodiment, the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25.

In an aspect of the present invention, provided herein is a pharmaceutically acceptable combination or composition as described herein, comprising a CFD inhibitor selected from Formula I or Formula II or its pharmaceutically acceptable salt and a C3 or C5 inhibitor. In one embodiment, the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25.

In an aspect of the present invention, provided herein is a pharmaceutically acceptable combination or composition as described herein, comprising a CFD inhibitor of Formula I or Formula II or its pharmaceutically acceptable salt and a CFB inhibitor. In one embodiment, the CFB inhibitor is a compound as described in PCT/US17/39587, incorporated herein by references. In one embodiment, the CFB inhibitor is:

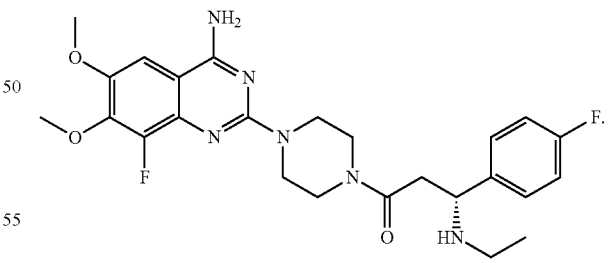

In one embodiment, the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25.

In an additional aspect, the present invention provides a pharmaceutically acceptable combination or composition as described herein, comprising a CFD inhibitor of Formula I or Formula II or its pharmaceutically acceptable salt and a pan-inhibitor to complement components. In one embodiment, the pan-inhibitor is FUT-175. In one embodiment, the CFD inhibitor is selected from Compounds 1, 2, 3, 4, 5, 6, 7, 8, 9, 10, 11, 12, 13, 14, 15, 16, 17, 18, 19, 20, 21, 22, 23, 24, or 25.

BRIEF DESCRIPTION OF THE FIGURES

FIGS. 7A-7L are flow cytometry analyses of C3 fragment deposition on artificial PNH cells under the treatment of various concentrations of Compound 1 as described in Example 12. The dot plots show the distribution of erythrocytes after being labeled with anti-human CD59 (y-axis) and anti-human C3c (x-axis) antibodies.

DETAILED DESCRIPTION OF THE INVENTION

Figure 1A:
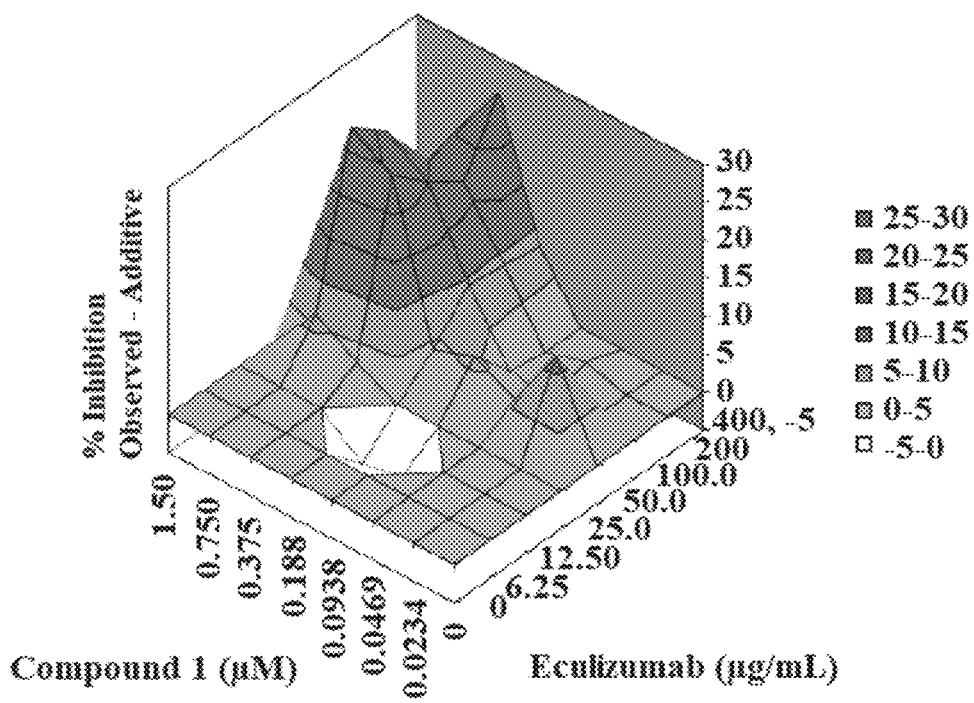
FIGS. 1A-1B are three-dimensional surface graphs showing that the combination of Compound 1 and eculizumab synergistically inhibit complement-mediated hemolysis of PNH erythrocytes. Each of the surface graphs have distinct and consistent positive peaks and as described in Example 1, substantial synergy volume. The concentration of eculizumab (μg/mL) is measured on the x-axis and the concentration of Compound 1 (μM) is measured on the y-axis. The z-axis represents the difference between measured inhibition and a theoretically determined additive inhibition. The positive surface peaks indicate greater inhibition than expected and therefore synergy, while negative surface peaks indicate less inhibition than expected and therefore antagonism.

The dysfunction, or excessive activation, of complement has been linked to many diseases, including Paroxysmal Nocturnal Hemoglobinuria (PNH), a clonal hematopoietic stem cell (HSC) disease that presents with hemolytic anemia, thrombosis, and smooth muscle dystonia, as well as bone marrow failure in some cases. Currently, the only approved treatment for PNH is the C5 monoclonal antibody eculizumab (Soliris™, Alexion Pharmaceuticals, Inc.). Provided herein are improved therapeutic regimens incorporating a CFD inhibitor selected from Formula I or II in combination with C5 inhibitors, C3, inhibitors, CFB inhibitors, or a pan-complement inhibitor, or a combination thereof.

Definitions

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The "subject" treated is typically a human subject, although it is to be understood the methods described herein are effective with respect to other animals, such as mammals and vertebrate species. More particularly, the term "subject" can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

The term "pharmaceutically acceptable salt" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salt" refers to the relatively non-toxic, inorganic and organic acid addition salts of compounds of the presently disclosed subject matter. These salts can be prepared in situ during the final isolation and purification of the compounds or by separately reacting the purified Compound in its free base form with a suitable organic or inorganic acid and isolating the salt thus formed. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N-dibenzylethylenediamine, chloroprocaine, choline, diethanolamine, ethylenediamine, N-methylglucamine, and procaine.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

"Pharmaceutical compositions" are compositions comprising at least one active agent, and at least one other substance, such as a pharmaceutically acceptable carrier or pharmaceutically acceptable excipient.

A "pharmaceutically acceptable excipient" means an excipient that is useful in preparing a pharmaceutical composition that is generally safe, non-toxic and neither biologically nor otherwise inappropriate for administration to a host, typically a human. In one embodiment, an excipient is used that is acceptable for veterinary use.

As used herein, the term "prodrug" means a compound which when administered to a host in vivo is converted into the parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

In one embodiment, the compounds of Formula I or Formula II include desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium ($^3H$) may be used anywhere in described structures. Alternatively, or in addition, isotopes of carbon, e.g., $^{13}C$ and $^{14}C$, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of, or eliminate, the metabolism at that bond. At any position of the compound that a hydrogen atom may be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium ($^1H$), is substituted by a H-isotope, i.e., deuterium ($^2H$). Deuterium substitution can be partial or complete. Partial deuterium substitution means that at least one hydrogen is substituted by at least one deuterium. In certain embodiments, the isotope is 90%, 95%, or 99% or more enriched in an isotope at any location of interest. In some embodiments, it is deuterium that is 90%, 95%, or 99% enriched at a desired location.

In the description above, below, and herein generally, whenever any of the terms referring to Formula I, Formula II, or a specific compound, for example Compound 1, are used, it should be understood that pharmaceutically acceptable salts, prodrugs, or compositions are considered included, unless otherwise stated or inconsistent with the text.

As contemplated herein and for purposes of the disclosed ranges herein, all ranges described herein include any and all numerical values occurring within the identified ranges. For example, a range of 1 to 10, or between 1 and 10, as contemplated herein, would include the numerical values 1, 2, 3, 4, 5, 6, 7, 8, 9, 10, as well as fractions thereof.

Paroxysmal Nocturnal Hemoglobinuria (PNH)

PNH is caused by somatic mutations in PIGA in bone marrow stem cells. Because stem cells give rise to all mature blood elements, including red blood cells, white blood cells, and platelets, cells derived from an abnormal stem cell will also carry the PIGA mutation. Cells harboring the PIGA mutation are deficient in a class of proteins called GPI-anchored proteins that are important for anchoring proteins in the cell membrane. Two important proteins that are unable to attach to the cell membrane via a GPI-anchor in PIGA-mutated cells are the CD59 glycoprotein (CD59) and the decay-accelerating factor (DAF, also known as CD55). These proteins are important for regulating the complement system, and their absence on the cell surface results in their susceptibility to destruction. The destruction of red blood cells (hemolysis), extravascular and intravascular, is associated with PNH.

In intravascular hemolysis, red blood cells lyse in circulation and release hemoglobin into the plasma (hemoglobinemia). One way to measure intravascular hemolysis is a test that measures the level of the enzyme lactate dehydrogenase (LDH). Subjects with PNH experiencing intravascular hemolysis have elevated levels of LDH. In extravascular hemolysis, red blood cells are phagocytized by macrophages. Extravascular hemolysis can be tracked indirectly by the continued loss of red blood cells (monitored by hemoglobin and transfusion dependence, i.e., the number of transfusions required over a specified time period). In subjects with PNH, the reticulocyte counts often remain elevated during treatment with eculizumab, because of the persistence of some extravascular hemolysis due to deposition of C3 fragments on PNH red cells. Additionally, extravascular hemolysis will result in increased presentation of unconjugated bilirubin to the hepatocyte. If the ability of the hepatocyte to take up and conjugate this bilirubin is overwhelmed, unconjugated bilirubin will accumulate in plasma, causing an increase in total and indirect bilirubin.

The only approved treatment for PNH is eculizumab, a monoclonal antibody inhibitor that binds to C5 and prevents the generation of C5a and C5b. While this prevents complement-mediated intravascular hemolysis, eculizumab leads to increased deposition of complement C3 fragments on PNH cells that may result in extravascular hemolysis. Eculizumab is unable to treat extravascular hemolysis, and therefore, even if intravascular hemolysis is prevented with eculizumab treatment, subjects can still experience extravascular hemolysis. A number of subjects ("partial responders" or "suboptimal responders") continue to suffer from anemia due to either incomplete inhibition of intravascular hemolysis or extravascular hemolysis.

Factor D Inhibitors

Factor D inhibitors for use in the present invention are selected from Formula I or Formula II:

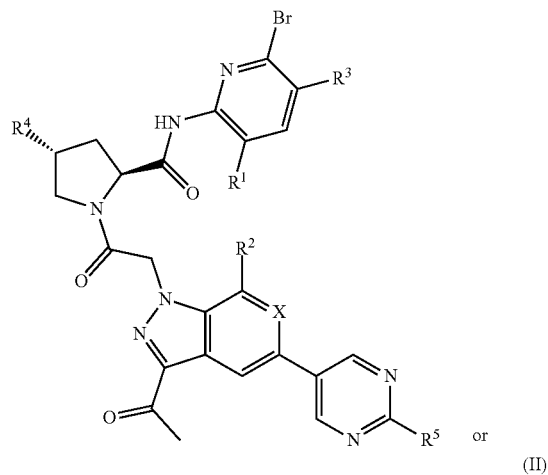

(I)

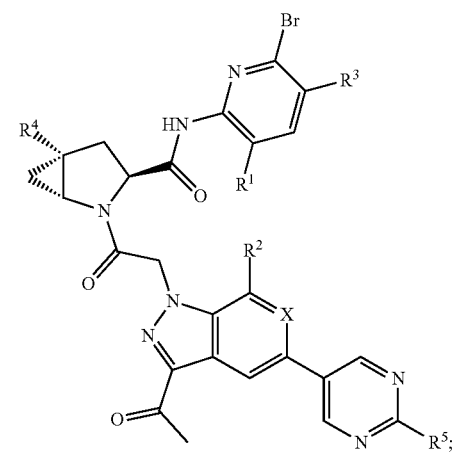

(II)

or a pharmaceutically acceptable composition, salt, N-oxide, isotopic analog, or prodrug thereof, wherein X, $R^1$, $R^2$, $R^3$, $R^4$, and $R^5$ are defined as above.

a. In one embodiment of any one of Formula I or Formula II, $R^1$ is hydrogen.
b. In one embodiment of any one of Formula I or Formula II, $R^1$ is $C_1$-$C_3$ alkyl.
c. In one embodiment of any one of Formula I or Formula II, $R^1$ is methyl.
d. In one embodiment of any one of Formula I or Formula II, $R^1$ is ethyl.
e. In one embodiment of any one of Formula I or Formula II, $R^1$ is halogen.
f. Any one of embodiments a-e, wherein X is N.
g. Any one of embodiments a-e, wherein X is CH.
h. Any one of embodiments a-g, wherein $R^2$ is $C_1$-$C_3$ alkyl.
i. Any one of embodiments a-g, wherein $R^2$ is hydrogen.
j. Any one of embodiments a-g, wherein $R^2$ is methyl.
k. Any one of embodiments a-g, wherein $R^2$ is ethyl.
l. Any one of embodiments a-k, wherein $R^3$ is hydrogen.
m. Any one of embodiments a-k, wherein $R^3$ is methyl.
n. Any one of embodiments a-k, wherein $R^3$ is ethyl.
o. Any one of embodiments a-k, wherein $R^3$ is fluorine.
p. Any one of embodiments a-o, wherein $R^4$ is $C_1$-$C_3$ alkyl.
q. Any one of embodiments a-o, wherein $R^4$ is methyl.
r. Any one of embodiments a-o, wherein $R^4$ is halogen.

s. Any one of embodiments a-r, wherein $R^5$ is cyano.
t. Any one of embodiments a-r, wherein $R^5$ is $C_1$-$C_3$ alkyl.
u. Any one of embodiments a-r, wherein $R^5$ is methyl.
v. Any one of embodiments a-r, wherein $R^5$ is halogen.

Compounds of Formula I and II can be synthesized using the methods disclosed in WO 2017/035353 and WO 2015/130838.

Non-limiting examples of compounds of Formula I and II are provided below in Table 1.

TABLE 1

| Cmpd # | Structure | IUPAC Name |
|---|---|---|
| 1 | 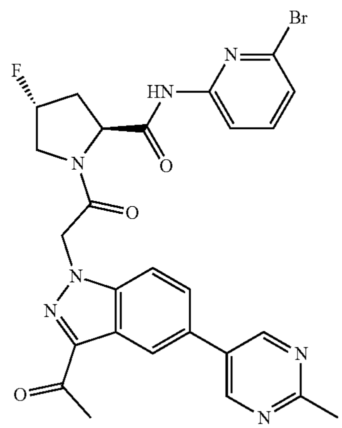 | (2S,4R)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide |
| 2 | 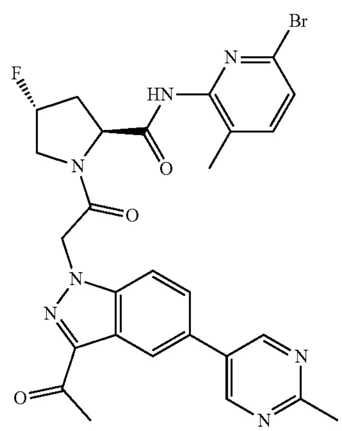 | (2S,4R)-1-(2-(3-acetyl-5-(2-methylpyrimidin-5-yl)-1H-indazol-1-yl)acetyl)-N-(6-bromo-3-methylpyridin-2-yl)-4-fluoropyrrolidine-2-carboxamide |
| 3 | 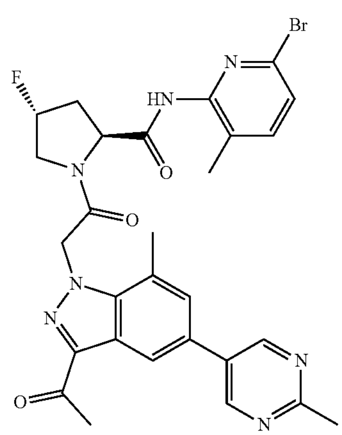 | (2S,4R)-1-(2-(3-acetyl-7-methyl-5-(2-methylpyrimidin-5-yl)-1H-indazol-1-yl)acetyl)-N-(6-bromo-3-methylpyridin-2-yl)-4-fluoropyrrolidine-2-carboxamide |

TABLE 1-continued

| Cmpd # | Structure | IUPAC Name |
|---|---|---|
| 4 | 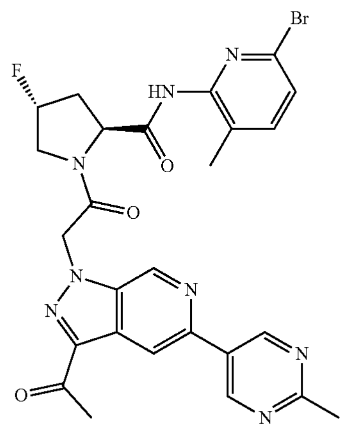 | (2S,4R)-1-(2-(3-acetyl-5-(2-methylpyrimidin-5-yl)-1H-pyrazolo[3,4-c]pyridin-1-yl)acetyl)-N-(6-bromo-3-methylpyridin-2-yl)-4-fluoropyrrolidine-2-carboxamide |
| 5 | 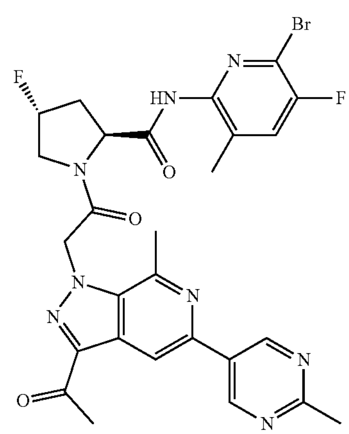 [SMILES: CC(=O)c1nn(CC(=O)N2C[C@H](F)C[C@H]2C(=O)Nc2nc(Br)c(F)cc2C)c2c(C)nc(-c3cnc(C)nc3)cc12] | (2S,4R)-1-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-4-fluoropyrrolidine-2-carboxamide |
| 6 | 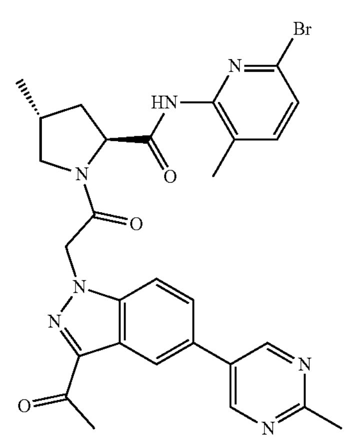 | (2S,4R)-1-(2-(3-acetyl-5-(2-methylpyrimidin-5-yl)-1H-indazol-1-yl)acetyl)-N-(6-bromo-3-methylpyridin-2-yl)-4-methylpyrrolidine-2-carboxamide |

TABLE 1-continued

| Cmpd # | Structure | IUPAC Name |
|---|---|---|
| 7 | 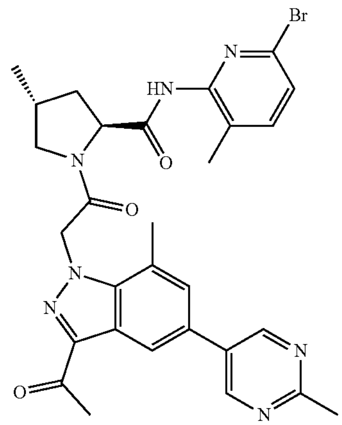 | (2S,4R)-1-(2-(3-acetyl-7-methyl-5-(2-methylpyrimidin-5-yl)-1H-indazol-1-yl)acetyl)-N-(6-bromo-3-methylpyridin-2-yl)-4-methylpyrrolidine-2-carboxamide |
| 8 | 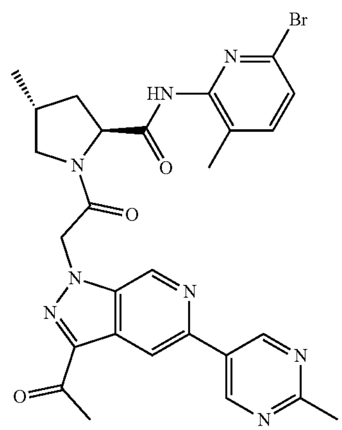 | (2S,4R)-1-(2-(3-acetyl-5-(2-methylpyrimidin-5-yl)-1H-pyrazolo[3,4-c]pyridin-1-yl)acetyl)-N-(6-bromo-3-methylpyridin-2-yl)-4-methylpyrrolidine-2-carboxamide |
| 9 | 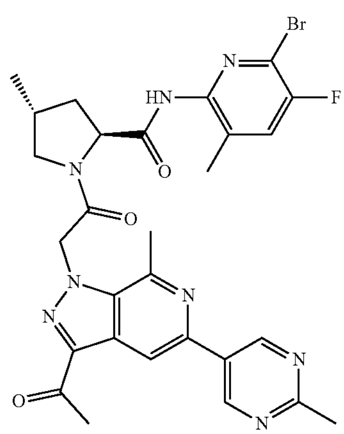 | (2S,4R)-1-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-4-methylpyrrolidine-2-carboxamide |

TABLE 1-continued

| Cmpd # | Structure | IUPAC Name |
| --- | --- | --- |
| 10 | 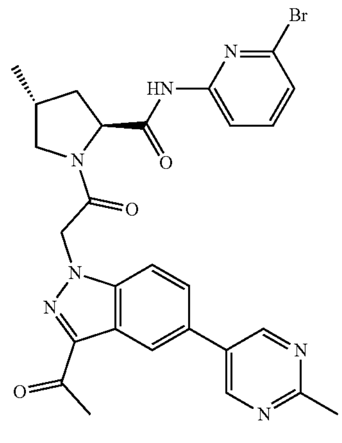 | (2S,4R)-1-(2-(3-acetyl-5-(2-methylpyrimidin-5-yl)-1H-indazol-1-yl)acetyl)-N-(6-bromopyridin-2-yl)-4-methylpyrrolidine-2-carboxamide |
| 11 | 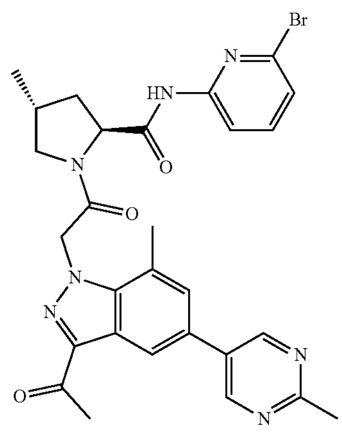 | (2S,4R)-1-(2-(3-acetyl-7-methyl-5-(2-methylpyrimidin-5-yl)-1H-indazol-1-yl)acetyl)-N-(6-bromopyridin-2-yl)-4-methylpyrrolidine-2-carboxamide |
| 12 | 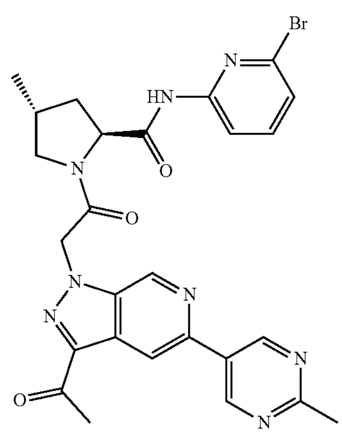 | (2S,4R)-1-(2-(3-acetyl-5-(2-methylpyrimidin-5-yl)-1H-pyrazolo[3,4-c]pyridin-1-yl)acetyl)-N-(6-bromopyridin-2-yl)-4-methylpyrrolidine-2-carboxamide |

TABLE 1-continued

| Cmpd # | Structure | IUPAC Name |
| --- | --- | --- |
| 13 | 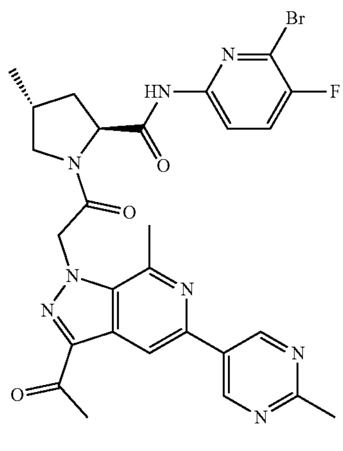 | (2S,4R)-1-(2-(3-acetyl-7-methyl-5-(2-methylpyrimidin-5-yl)-1H-pyrazolo[3,4-c]pyridin-1-yl)acetyl)-N-(6-bromo-5-fluoropyridin-2-yl)-4-methylpyrrolidine-2-carboxamide |
| 14 | 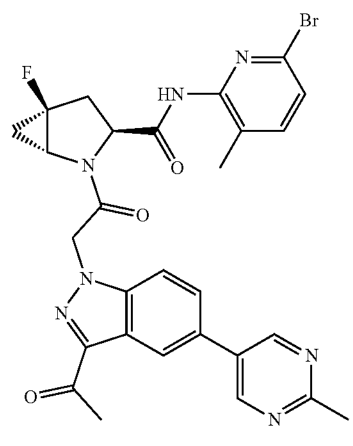 [SMILES: CC(=O)c1nn(CC(=O)N2[C@H](C(=O)Nc3nc(Br)ccc3C)C[C@@]3(F)C[C@@H]23)c2ccc(-c3cnc(C)nc3)cc12] | (1R,3S,5S)-2-(2-(3-acetyl-5-(2-methylpyrimidin-5-yl)-1H-indazol-1-yl)acetyl)-N-(6-bromo-3-methylpyridin-2-yl)-5-fluoro-2-azabicyclo[3.1.0]hexane-3-carboxamide |
| 15 | 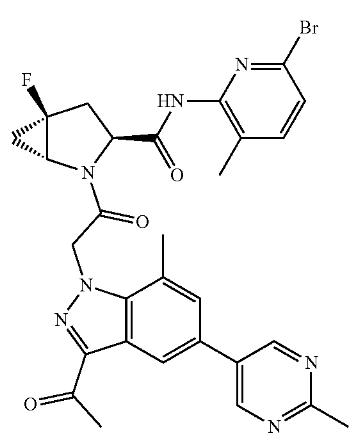 [SMILES: CC(=O)c1nn(CC(=O)N2[C@H](C(=O)Nc3nc(Br)ccc3C)C[C@@]3(F)C[C@@H]23)c2c(C)cc(-c3cnc(C)nc3)cc12] | (1R,3S,5S)-2-(2-(3-acetyl-7-methyl-5-(2-methylpyrimidin-5-yl)-1H-indazol-1-yl)acetyl)-N-(6-bromo-3-methylpyridin-2-yl)-5-fluoro-2-azabicyclo[3.1.0]hexane-3-carboxamide |

TABLE 1-continued

| Cmpd # | Structure | IUPAC Name |
|---|---|---|
| 16 | 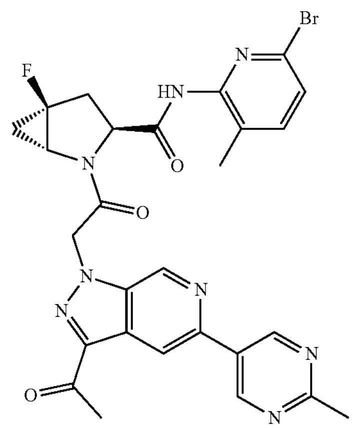 [SMILES: CC(=O)c1nn(CC(=O)N2[C@H](C(=O)Nc3nc(Br)ccc3C)C[C@@]3(F)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-fluoro-2-azabicyclo[3.1.0]hexane-3-carboxamide |
| 17 | 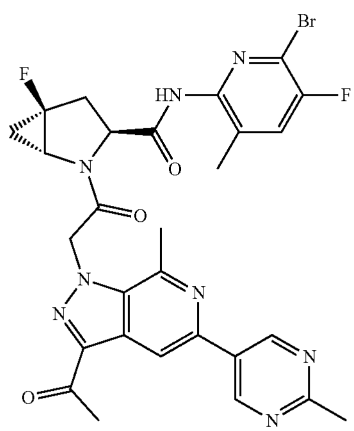 [SMILES: CC(=O)c1nn(CC(=O)N2[C@H](C(=O)Nc3nc(Br)c(F)cc3C)C[C@@]3(F)C[C@@H]23)c2c(C)nc(-c3cnc(C)nc3)cc12] | (1R,3S,5S)-2-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-5-fluoro-2-azabicyclo[3.1.0]hexane-3-carboxamide |
| 18 | 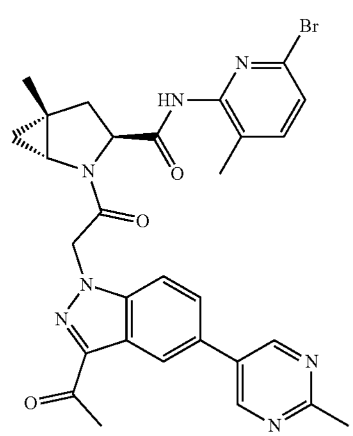 [SMILES: CC(=O)c1nn(CC(=O)N2[C@H](C(=O)Nc3nc(Br)ccc3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide |

TABLE 1-continued

| Cmpd # | Structure | IUPAC Name |
|---|---|---|
| 19 | 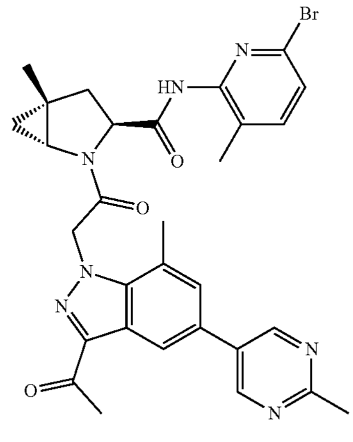 [SMILES: CC(=O)c1nn(CC(=O)N2[C@H](C(=O)Nc3nc(Br)ccc3C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide |
| 20 | 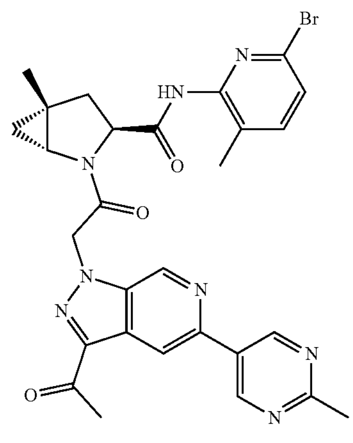 [SMILES: CC(=O)c1nn(CC(=O)N2[C@H](C(=O)Nc3nc(Br)ccc3C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide |
| 21 | 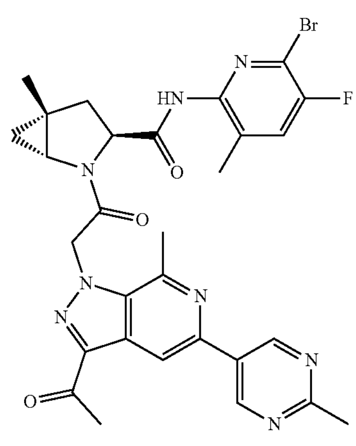 [SMILES: CC(=O)c1nn(CC(=O)N2[C@H](C(=O)Nc3nc(Br)c(F)cc3C)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide |

TABLE 1-continued

| Cmpd # | Structure | IUPAC Name |
|---|---|---|
| 22 | 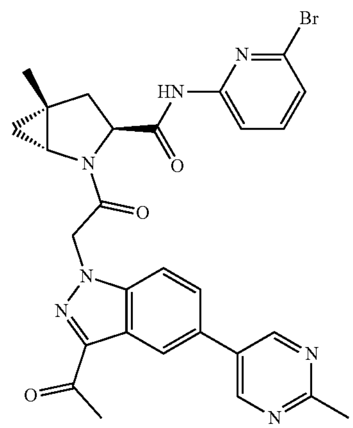 [SMILES: CC(=O)c1nn(CC(=O)N2[C@H](C(=O)Nc3cccc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromopyridin-2-yl)-5-methyl-2-azabicyclo[3.1.0]hexane-3-carboxamide |
| 23 | 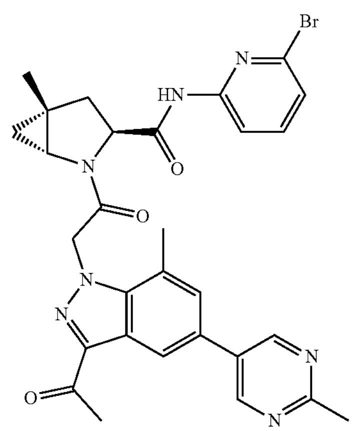 [SMILES: CC(=O)c1nn(CC(=O)N2[C@H](C(=O)Nc3cccc(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromopyridin-2-yl)-5-methyl-2-azabicyclo[3.1.0]hexane-3-carboxamide |
| 24 | 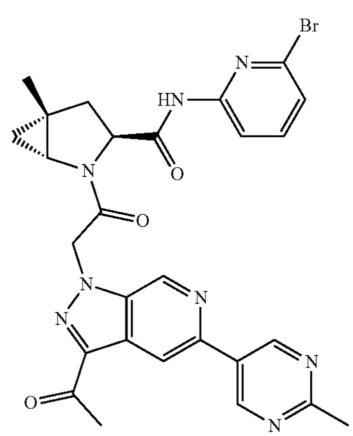 [SMILES: CC(=O)c1nn(CC(=O)N2[C@H](C(=O)Nc3cccc(Br)n3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromopyridin-2-yl)-5-methyl-2-azabicyclo[3.1.0]hexane-3-carboxamide |

TABLE 1-continued

| Cmpd # | Structure | IUPAC Name |
|---|---|---|
| 25 | 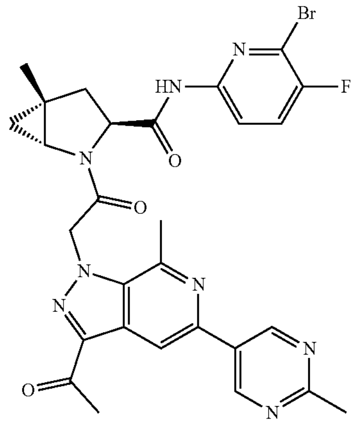 [SMILES: CC(=O)c1nn(CC(=O)N2[C@H](C(=O)Nc3ccc(F)c(Br)n3)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-5-fluoropyridin-2-yl)-5-methyl-2-azabicyclo[3.1.0]hexane-3-carboxamide |

An exemplary CFD inhibitor for use in the present invention is, for example, Compound 1. Compound 1 is a potent Factor D inhibitor, having a binding affinity to human CFD of $K_D$=0.54 nM, and an inhibition of catalytic activity of CFD against Factor B of $IC_{50}$=17 nM. It also strongly inhibits AP activity in vitro, showing an $IC_{50}$ of 27 nM for rabbit erythrocyte hemolysis, 14 nM for PNH erythrocyte hemolysis, and 26 nM by Wieslab assay.

Methods of making Compound 1 are provided below:

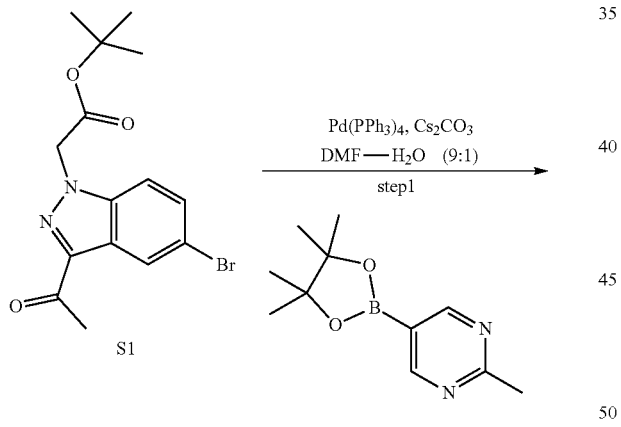

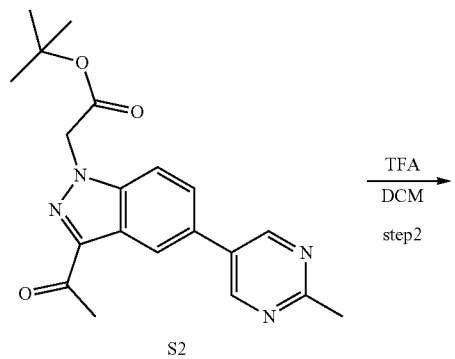

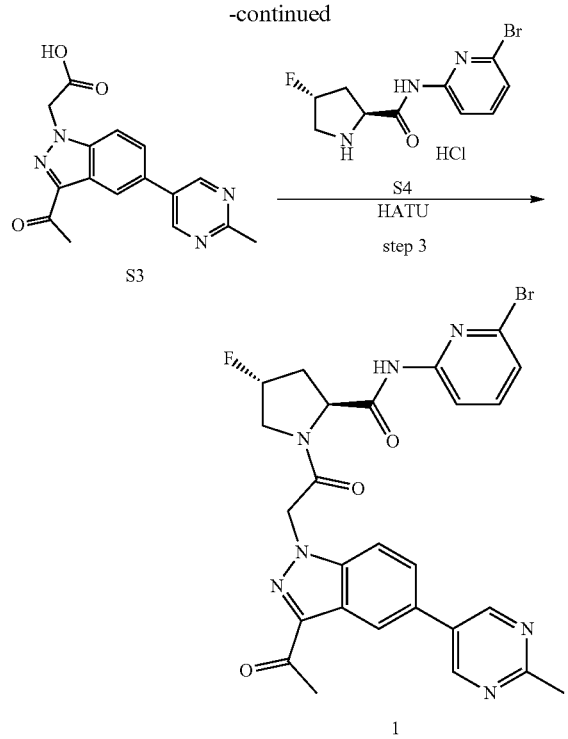

Factor D inhibitor ((2S,4R)-1-(2-(3-Acetyl-5-(2-methylpyrimidin-5-yl)-1H-indazol-1-yl)acetyl)-N-(6-bromopyridin-2-yl)-4-fluoropyrrolidine-2-carboxamide) (Compound 1) has been previously described, see U.S. Patent Appl. Pub. 2015/0239895 and 2017/0066783. Compound 1 may be synthesized by methods known to those in the art. In step 1, tert-butyl 2-(3-acetyl-5-bromo-1H-indazol-1-yl)acetate (S1) is coupled to 2-methyl-5-(4,4,5,5-tetramethyl-1,3,2-dioxaborolan-2-yl)pyrimidine using tetrakis(triphenylphosphine) palladium(0) in the presence of base to provide tert-butyl 2-(3-acetyl-5-(2-methylpyrimidin-5-yl)-1H-indazol-1-yl)acetate (S2). In step 2, hydrolysis of tert-butyl 2-(3-acetyl-5-(2-methylpyrimidin-5-yl)-1H-indazol-1-yl)acetate (S2) with trifluoroacetic acid provides 2-(3-acetyl-5-(2-methylpyrimidin-5-yl)-1H-indazol-1-yl)acetic acid (S3). In step 3, 2-(3-acetyl-5-(2-methylpyrimidin-5-yl)-1H-indazol-1-yl) acetic acid (S3) and (2S,4R)—N-(6-bromopyridin-2-yl)-4-fluoropyrrolidine-2-carboxamide (S4) are coupled using HATU to provide (2S,4R)-1-(2-(3-Acetyl-5-(2-methylpyrimidin-5-yl)-1H-indazol-1-yl)acetyl)-N-(6-bromopyridin-2-yl)-4-fluoropyrrolidine-2-carboxamide (1).

C5 Inhibitors

Provided herein are methods for treating PNH in a subject comprising administering to the subject an effective amount of a C5 inhibitor in combination or alternation with an effective amount of a CFD inhibitor selected from Formula I or Formula II.

C5 inhibitors are known in the art. In one embodiment, the C5 inhibitor is a monoclonal antibody targeting C5. In one embodiment, the C5 inhibitor is eculizumab (Soliris™ Alexion Pharmaceuticals, New Haven, CT, see, e.g., U.S. Pat. No. 9,352,035).

In some embodiments, the C5 inhibitor may be, but is not limited to: a recombinant human minibody, for example Mubodina® (monoclonal antibody, Adienne Pharma and Biotech, Bergamo, Italy; see U.S. Pat. No. 7,999,081); coversin (small animal protein, Volution Immuno-pharmaceuticals, Geneva, Switzerland; see e.g. Penabad et al. Lupus, 2012, 23(12):1324-6); LFG316 (monoclonal antibody, Novartis, Basel, Switzerland, and Morphosys, Planegg, Germany; see U.S. Pat. Nos. 8,241,628 and 8,883, 158); ARC-1905 (pegylated RNA aptamer, Ophthotech, Princeton, NJ and New York, NY; see Keefe et al., Nature Reviews Drug Discovery, 9, 537-550); RA101348 and RA101495 (macrocyclic peptides, Ra Pharmaceuticals, Cambridge, MA); SOBI002 (affibody, Swedish Orphan Biovitrum, Stockholm, Sweden); ALN-CC5 (Si-RNA, Alnylam Pharmaceuticals, Cambridge, MA); ARC1005 (aptamers, Novo Nordisk, Bagsvaerd, Denmark); SOMAmers (aptamers, SomaLogic, Boulder, CO); SSL7 (bacterial protein toxin, see, e.g. Laursen et al. Proc. Natl. Acad. Sci. U.S.A., 107(8):3681-6); MEDI7814 (monoclonal antibody, MedImmune, Gaithersburg, MD); aurin tricarboxylic acid; aurin tricarboxylic acid derivatives (Aurin Biotech, Vancouver, BC, see U.S. Patent Appl. Pub. 2013/003592); RG6107 (anti-C5 recycling antibody, Roche Pharmaceuticals, Basel, Switzerland); ALXN1210 and ALXN5500 (monoclonal antibodies, Alexion Pharmaceuticals, New Haven, CT); TT30 (fusion protein, Alexion Pharmaceuticals, New Haven, CT); REGN3918 (monoclonal antibody, Regeneron, Tarrytown, NY); ABP959 (eculizumab biosimilar, Amgen, Thousand Oaks, CA); or combinations thereof.

In one embodiment, the C5 inhibitor is a recombinant human minibody, for example Mubodina®. Mubodina® is a fully human recombinant antibody C5 developed by Adienne Pharma and Biotech. Mubodina® is described in U.S. Pat. No. 7,999,081.

In one embodiment, the C5 inhibitor is coversin. Coversin is a recombinant protein derived from a protein discovered in the saliva of the *Ornithodoros moubata* tick currently developed as a recombinant protein by Akari Therapeutics. Coversin is described in Penabad et al. Lupus 2012, 23(12): 1324-6.

In one embodiment, the C5 inhibitor is Tesidolumab/ LFG316. Tesidolumab is a monoclonal antibody developed by Novartis and Morphosys. Tesidolumab is described in U.S. Pat. Nos. 8,241,628 and 8,883,158.

In one embodiment, the C5 inhibitor is ARC-1905. ARC-1905 is a pegylated RNA aptamer developed by Ophthotech. ARC-1905 is described in Keefe et al. Nature Reviews Drug Discovery, 9:537-550.

In one embodiment, the C5 inhibitor is RA101348. RA101348 is a macrocyclic peptide developed by Ra Pharmaceuticals.

In one embodiment, the C5 inhibitor is RA101495. RA101495 is a macrocyclic peptide developed by Ra Pharmaceuticals.

In one embodiment, the C5 inhibitor is SOBI002. SOBI002 is an affibody developed by the Swedish Orphan Biovitrum.

In one embodiment, the C5 inhibitor is ARC1005. ARC1005 is an aptamer developed by Novo Nordisk.

In one embodiment, the C5 inhibitor is SOMAmers for C5. SOMAmers are aptamers developed by SomaLogic.

In one embodiment, the C5 inhibitor is SSL7. SSL7 is a bacterial protein toxin described in Laursen et al. Proc. Natl. Acad. Sci. U.S.A., 107(8):3681-6.

In one embodiment, the C5 inhibitor is MEDI7814. MEDI7814 is a monoclonal antibody developed by MedImmune.

In one embodiment, the C5 inhibitor is aurin tricarboxylic acid. In another embodiment, the C5 inhibitor is an aurin tricarboxylic acid derivative. These aurin derivatives were developed by Aurin Biotech and are further described in U.S. Patent Appl. Pub. No. 2013/003592).

In one embodiment, the C5 inhibitor is RG6107/SKY59. RG6107/SKY59 is an anti-C5 recycling antibody developed by Roche Pharmaceuticals.

In one embodiment, the C5 inhibitor is ALXN1210. In another embodiment, the C5 inhibitor is ALXN5500. ALXN1210 and ALXN5500 are monoclonal antibodies developed by Alexion Pharmaceuticals.

In one embodiment, the C5 inhibitor is TT30. TT30 is a fusion protein developed by Alexion Pharmaceuticals.

In one embodiment, the C5 inhibitor is ABP959. ABP959 is an eculizamab biosimilar monoclonal antibody developed by Amgen.

In one embodiment, the C5 inhibitor is Anti-C5 siRNA. Anti-C5 siRNA was developed by Alnylam Pharmaceuticals.

In one embodiment, the C5 inhibitor is Erdigna®. Erdigna® is an antibody developed by Adienne Pharma.

In one embodiment, the C5 inhibitor is avacincaptad pegol/Zimura®. Avacincaptad pegol is in aptamer developed by Opthotech.

In one embodiment, the C5 inhibitor is SOBI005. SOBI005 is a protein in developed by the Swedish Orphan Biovitrum.

In one embodiment, the C5 inhibitor is ISU305. ISU305 is a monoclonal antibody developed by ISU ABXIS.

In one embodiment, the C5 inhibitor is REGN3918. REGN3918 is a monoclonal antibody developed by Regeneron.

C3 Inhibitors

Provided herein are methods for treating PNH in a subject comprising administering to the subject an effective amount of a C3 inhibitor in combination or alternation with an effective amount of a CFD inhibitor selected from Formula I or Formula II.

C3 inhibitors are known in the art. In one embodiment, Compound 1 is administered in combination or alternation with compstatin and/or a compstatin analog. Compstatin and compastin analogs are known and are found to be useful inhibitors of C3, see U.S. Pat. Nos. 9,056,076; 8,168,584; 9,421,240; 9,291,622; 8,580,735; 9,371,365; 9,169,307; 8,946,145; 7,989,589; 7,888,323; 6,319,897; and US Patent Appl. Pub. Nos. 2016/0060297; 2016/0015810; 2016/ 0215022; 2016/0215020; 2016/0194359; 2014/0371133;

2014/0323407; 2014/0050739; 2013/0324482; and 2015/0158915. In one embodiment, the compstatin analog having the amino acid sequence ICVVQDWGHHCRT (SEQ. ID. NO. 1). In another embodiment, the C3 inhibitor is a compstatin analog. In one embodiment, the compstatin analog is 4(1MeW)/APL-1 of the sequence Ac-ICV(1-mW)QDWGAHRCT (SEQ. ID. NO. 2), wherein Ac is acetyl and 1-mW is 1-methyltryptophan. In another embodiment, the compstatin analog is Cp40/AMY-101, which has an amino acid sequence yICV(1mW)QDW-Sar-AHRC-mI (SEQ. ID. NO. 3), wherein y is D-tyrosine, 1 mW is 1-methyltryptophan, Sar is sarcosine, and mI is N-methylisoleucine. In yet another embodiment, the compstatin analog is PEG-Cp40, having the amino acid sequence PEG-yICV(1mW)QDW-Sar-AHRC-mI (SEQ. ID. NO. 4), wherein PEG is polyethyleneglycol (40 kDa), y is D-tyrosine, 1 mW is 1-methyltryptophan, Sar is sarcosine, and mI is N-methylisoleucine. In yet another embodiment, the compstatin analog is 4(1MeW)POT-4. 4(1MeW)POT-4 was developed by Potentia. In yet another embodiment, the compstatin analog is AMY-201. AMY-201 was developed by Amyndas Pharmaceuticals.

In some embodiments, Compound 1 can be combined with C3 inhibitors that include, but are not limited to: H17 (monoclonal antibody, EluSys Therapeutics, Pine Brook, NJ); mirococept (CR1-based protein); sCR1 (CR1-based protein, Celldex, Hampton, NJ); TT32 (CR-1 based protein, Alexion Pharmaceuticals, New Haven, CT); HC-1496 (recombinant peptide); CB 2782 (enzyme, Catalyst Biosciences, South San Francisco, CA); APL-2 (pegylated synthetic cyclic peptide, Apellis Pharmaceuticals, Crestwood, KY); or combinations thereof.

In one embodiment, the C3 inhibitor is H17. H17 is a humanized monoclonal antibody in development by EluSys Therapeutics. H17 is described in Paixao-Cavalcante et al. J. Immunol. 2014, 192(10):4844-4851.

In one embodiment, the C3 inhibitor is mirococept. Mirococept is a CR1-based protein developed by Inflazyme Pharmaceuticals.

In one embodiment, the C3 inhibitor is sCR1. sCR1 is a soluble form of the CR1 protein developed by Celldex.

In one embodiment, the C3 inhibitor is TT32. TT32 is a CR-1 based protein developed by Alexion Pharmaceuticals.

In one embodiment, the C3 inhibitor is HC-1496. HC-1496 is a recombinant peptide developed by InCode.

In one embodiment, the C3 inhibitor is CB 2782. CB 2782 is novel protease derived from human membrane type serine protease 1 (MTSP-1) that was developed by Catalyst Biosciences.

In one embodiment, the C3 inhibitor is APL-2. APL-2 is a pegylated version of APL-1 developed by Apellis Pharmaceuticals.

CFB Inhibitors

Provided herein are methods for treating PNH comprising administering a CFB inhibitor in combination or alternation with Compound 1. CFB inhibitors are known in the art. In some embodiments, Compound 1 can be combined with CFB inhibitors that include, but are not limited to: anti-FB SiRNA (Alnylam Pharmaceuticals, Cambridge, MA); TA106 (monoclonal antibody, Alexion Pharmaceuticals, New Haven, CT); LNP023 (small molecule, Novartis, Basel, Switzerland); SOMAmers (aptamers, SomaLogic, Boulder, CO); bikaciomab (Novelmed Therapeutics, Cleveland, OH); complin (see, Kadam et al., J. Immunol. 2010, DOI:10.409/jimmunol.10000200); Ionis-FB-L$_{Rx}$ (ligand conjugated antisense drug, Ionis Pharmaceuticals, Carlsbad, CA); or a combination thereof. In another embodiment, CFB inhibitors that can be combined with Compound 1 as described herein include those disclosed in PCT/US17/39587. In another embodiment, CFB inhibitors that can be combined with Compound 1 as described herein include those disclosed in PCT/US17/014458. In another embodiment, CFB inhibitors that can be combined with Compound 1 as described herein include those disclosed in U.S. Patent Appl. Pub. No. 2016/0024079 (assigned to Novartis AG). In one embodiment, the CFB inhibitor is

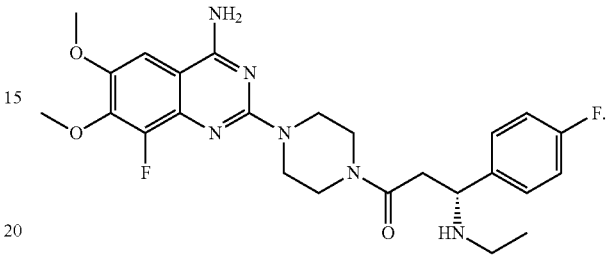

In one embodiment, the CFB inhibitor is anti-FB siRNA. Anti-FB siRNA was developed by Alnylam Pharmaceuticals.

In one embodiment, the CFB inhibitor is TA106. TA106 is a monoclonal antibody developed by Alexion Pharmaceuticals.

In one embodiment, the CFB inhibitor is LNP023. LNP023 is a small molecule inhibitor of CFB developed by Novartis. LNP023 and related inhibitors are described in Maibaum et al. Nat. Chem. Biol. 2016, 12:1105-1110.

In one embodiment, the CFB inhibitor is complin. Complin is a peptide inhibitor that is described in Kadam et al. J. Immunol. 2010 184(12):7116-24.

In one embodiment, the CFB inhibitor is Ionis-FB-LRx. Ionis-FB-LRx is a ligand conjugated antisense drug developed by Ionis Pharmaceuticals.

Pan-Inhibitors of Complement Components

Provided herein are methods for treating PNH comprising administering a pan-inhibitor of complement components in combination or alternation with Compound 1. Pan-inhibitors of complement components are known in the art. In one embodiment, the inhibitor is FUT-175.

Methods of Treatment

The present invention provides methods of treating a subject with PNH comprising administering to the subject a C5, C3, and/or pan-complement inhibitor in combination or alternation with a CFD inhibitor selected from Formula I or Formula II described herein, or a pharmaceutically acceptable salt thereof, including, but not limited to Compound 1, 2, 3, 4, 5, 6, 7, 8, 9, 10, 11, 12, 13, 14, 15, 16, 17, 18, 19, 20, 21, 22, 23, 24, or 25.

In one aspect, a method of treating a subject with PNH is provided comprising administrating to the subject a therapeutically effective amount of a C5 inhibitor in combination with a therapeutically effective amount of a CFD inhibitor selected from a compound of Formula I or Formula II, or a pharmaceutically acceptable salt thereof. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10, In one embodiment, the CFD inhibitor is Compound 11 In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a therapeutically effective amount of a C5 inhibitor in alternation with a therapeutically effective amount of a CFD inhibitor selected from a compound of Formula I or Formula II, or a pharmaceutically acceptable salt thereof. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFI) inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFI) inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a therapeutically effective amount of a C5 inhibitor in combination or alternation with a therapeutically effective amount of a CFD inhibitor selected from a compound of Formula I or Formula II, or a pharmaceutically acceptable salt thereof, wherein the subject has a genetic polymorphism of the Complement Receptor 1 gene (CR1). In one embodiment, the CR1 polymorphism is the HindIII H/L genotype. In one embodiment, the CR1 polymorphism is the HindIII L/L genotype. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MED17814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13, In one embodiment, the CFD inhibitor is Compound 14, In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been or is currently on a therapeutic regimen comprising the administration of a C5 inhibitor and is experiencing residual intravascular hemolysis. In one embodiment, the subject has a hemoglobin level of less than about 12 g/dL. In one embodiment, the subject has a hemoglobin level of less than about 10 g/dL. In one embodiment, the subject has a hemoglobin level of less than about 8 g/dL. In one embodiment, the subject has an LDH level greater than the upper limit of normal. In one embodiment, the subject has an LDH level greater than about 250 U/L. In one embodiment, the subject has an LDH level greater than about 500 U/L. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has had two or more blood transfusions within the prior six months. In one embodiment, the subject has had four or more blood transfusions within the prior six months. In a particular embodiment, upon administration of the CFD inhibitor, the C5 inhibitor is no longer administered. In another particular embodiment, upon administration of the CFD inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been on a therapeutic regimen comprising the administration of a C5 inhibitor and is experiencing extravascular hemolysis. In one embodiment, the subject has a hemoglobin level of less than about 12 g/dL. In one embodiment, the subject has a hemoglobin level of less than about 10 g/dL. In one embodiment, the subject has a hemoglobin level of less than about 8 g/dL. In one embodiment, the subject has an LDH level less than the upper limit of normal. In one embodiment, the subject has an LDH level less than about 250 U/L. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has had two or more blood transfusions within the prior six months. In one embodiment, the subject has had four or more blood transfusions within the prior six months. In a particular embodiment, upon administration of the CFD inhibitor, the C5 inhibitor is no longer administered. In another particular embodiment, upon administration of the CFD inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5, In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD) inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been on a therapeutic regimen comprising the administration of a C5 inhibitor, and wherein the subject at the time of administration of the CFD inhibitor has a hemoglobin level of less than about 12.0 g/dL. In one embodiment, the subject has a hemoglobin level of less than about 10.0 g/dL. In one embodiment, the subject has a hemoglobin level of less than about 8.0 g/dL. In one embodiment, the subject has an LDH level of greater than the upper limit of normal. In one embodiment, the subject has an LDH level of lesser than the upper limit of normal. In one embodiment, the subject has an LDH level of less than about 250 U/L. In one embodiment, the subject has an LDH level of greater than about 250 U/L. In one embodiment, the subject has an LDH level of greater than about 500 U/L. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has had two or more blood transfusions within the prior six months. In one embodiment, the subject has had four or more blood transfusions within the prior six months. In a particular embodiment, upon administration of the CFD inhibitor, the C5 inhibitor is no longer administered. In another particular embodiment, upon administration of the CFD) inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFI) inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been on a therapeutic regimen comprising the administration of a C5 inhibitor, and wherein the subject at the time of administration of the CFD inhibitor has a hemoglobin level of less than about 12.0 g/dL and a LDH level of greater than about 250 U/L. In one embodiment, the subject has a hemoglobin level of less than about 10.0 g/dL. In one embodiment, the subject has a hemoglobin level of less than about 8.0 g/dL. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has had two or more blood transfusions within the prior six months. In one embodiment, the subject has had four or more blood transfusions within the prior six months. In a particular embodiment, upon administration of the CFD inhibitor, the C5 inhibitor is no longer administered. In another particular embodiment, upon administration of the CFD inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been on a therapeutic regimen comprising the administration of a C5 inhibitor, and wherein the subject at the time of administration of the CFD inhibitor has a hemoglobin level of less than about 12.0 g/dL and a LDH level of greater than about 500 U/L. In one embodiment, the subject has a hemoglobin level of less than about 10.0 g/dL. In one embodiment, the subject has a hemoglobin level of less than about 8.0 g/dL. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has two or more blood transfusions within the prior six months. In a particular embodiment, upon administration of the CFD inhibitor, the C5 inhibitor is no longer administered. In another particular embodiment, upon administration of the CFD inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 1. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been on a therapeutic regimen comprising the administration of a C5 inhibitor, and wherein the subject at the time of administration of the CFD inhibitor has a hemoglobin level of less than about 12.0 g/dL and a LDH level of less than about 250 U/L. In one embodiment, the subject has a hemoglobin level of less than about 10.0 g/dL. In one embodiment, the subject has a hemoglobin level of less than about 8.0 g/dL. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has had two or more blood transfusions within the prior six months. In one embodiment, the subject has had found or more blood transfusions within the prior six months. In a particular embodiment, upon administration of the CFD inhibitor, the C5 inhibitor is no longer administered. In another particular embodiment, upon administration of the CFD inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been on a therapeutic regimen comprising the administration of a C5 inhibitor, and wherein the subject at the time of administration of the CFD inhibitor has a positive direct Coombs test. In one embodiment, the subject has a hemoglobin level of less than about 12 g/dL. In one embodiment, the subject has a hemoglobin level of less than about 10 g/dL. In one embodiment, the subject has a hemoglobin level of less than about 8 g/dL. In one embodiment, the subject has an LDH level that is greater than the upper limit of normal. In one embodiment, the subject has an LDH level that is less than the upper limit or normal. In one embodiment, the subject has an LDH level of less than about 250 U/L. In one embodiment, the subject has an LDH level of greater than about 250 U/L. In one embodiment, the subject has an LDH level of greater than about 500 U/L. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has two or more blood transfusions within the prior six months. In a particular embodiment, upon administration of the CFD inhibitor, the C5 inhibitor is no longer administered. In another particular embodiment, upon administration of the CFD inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD) inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment, 150 mg of Compound 1 is administered three times a day. In one embodiment, 200 mg of Compound 1 is administered three times a day.

In one aspect, a method of treating a subject with PNH is provided comprising administering to the subject a CFD inhibitor selected from a compound of Formula I or Formula II, or a pharmaceutically acceptable salt thereof, wherein the subject at the time of administration of the CFD inhibitor has been on a therapeutic regimen comprising the administration of a C5 inhibitor, and wherein the subject at the time of administration of the C5 inhibitor shows C3 fragment deposition. In one embodiment, the subject has a hemoglobin level of less than about 10 g/dL. In one embodiment, the subject has a hemoglobin level of less than about 8 g/dL. In one embodiment, the subject has an LDH level that is greater than the upper limit of normal. In one embodiment, the subject has an LDH level that is less than the upper limit or normal. In one embodiment, the subject has an LDH level of less than about 250 U/L. In one embodiment, the subject has an LDH level of greater than about 250 U/L. In one embodiment, the subject has an LDH level of greater than about 500 U/L. In one embodiment, at the time of administration of the CFD inhibitor, the subject is blood transfusion dependent. In one embodiment, at the time of administration of the CFD inhibitor, the subject has received one or more blood transfusions within the prior twelve months. In one embodiment, the subject has two or more blood transfusions within the prior six months. In a particular embodiment, upon administration of the CFD inhibitor, the C5 inhibitor is no longer administered. In another particular embodiment, upon administration of the CFD inhibitor, the C5 inhibitor also continues to be administered. In a particular embodiment, the C5 inhibitor is a monoclonal antibody to C5. In one embodiment, the C5 inhibitor is eculizamab. In one embodiment, the C5 inhibitor is a recombinant human minibody, for example Mubodina® (Adienne Pharma and Biotech). In one embodiment, the C5 inhibitor is coversin (Akari Therapeutics). In one embodiment, the C5 inhibitor is Tesidolumab/LFG316 (Novartis/Morphosys). In one embodiment, the C5 inhibitor is ARC-1905 (Ophthotech). In one embodiment, the C5 inhibitor is RA101348 (Ra Pharmaceuticals). In one embodiment, the C5 inhibitor is RA101495 (Ra Pharmaceuticals). In one embodiment, the C5 inhibitor is SOBI002 (Swedish Orphan Biovitrum). In one embodiment, the C5 inhibitor is ARC1005 (Novo Nordisk). In one embodiment, the C5 inhibitor is a SOMAmer for C5 (SomaLogic). In one embodiment, the C5 inhibitor is SSL7. In one embodiment, the C5 inhibitor is MEDI7814 (MedImmune). In one embodiment, the C5 inhibitor is aurin tricarboxylic acid (Aurin Biotech). In another embodiment, the C5 inhibitor is an aurin tricarboxylic acid derivative (Aurin Biotech). In one embodiment, the C5 inhibitor is RG6107/SKY59 (Roche Pharmaceuticals). In one embodiment, the C5 inhibitor is ALXN1210 (Alexion Pharmaceuticals). In another embodiment, the C5 inhibitor is ALXN5500 (Alexion Pharmaceuticals). In one embodiment, the C5 inhibitor is TT30 (Alexion Pharmaceuticals). In one embodiment, the C5 inhibitor is ABP959 (Amgen). In one embodiment, the C5 inhibitor is Anti-C5 siRNA (Alnylam Pharmaceuticals). In one embodiment, the C5 inhibitor is Erdigna (Adienne Pharma). In one embodiment, the C5 inhibitor is avacincaptad pegol/Zimura® (Ophthotech). In one embodiment, the C5 inhibitor is SOBI005 (Swedish Orphan Biovitrum). In one embodiment, the C5 inhibitor is ISU305 (ISU ABXIS). In one embodiment, the C5 inhibitor is REGN3918 (Regeneron). In one embodiment, the subject has been on a C5 therapeutic regimen for at least 3-months prior to administration of the CFD inhibitor. In one embodiment, the CFD inhibitor is Compound 1. In one embodiment, the CFD inhibitor is Compound 2. In one embodiment, the CFD inhibitor is Compound 3. In one embodiment, the CFD inhibitor is Compound 4. In one embodiment, the CFD inhibitor is Compound 5. In one embodiment, the CFD inhibitor is Compound 6. In one embodiment, the CFD inhibitor is Compound 7. In one embodiment, the CFD inhibitor is Compound 8. In one embodiment, the CFD inhibitor is Compound 9. In one embodiment, the CFD inhibitor is Compound 10. In one embodiment, the CFD inhibitor is Compound 11. In one embodiment, the CFD inhibitor is Compound 12. In one embodiment, the CFD inhibitor is Compound 13. In one embodiment, the CFD inhibitor is Compound 14. In one embodiment, the CFD inhibitor is Compound 15. In one embodiment, the CFD inhibitor is Compound 16. In one embodiment, the CFD inhibitor is Compound 17. In one embodiment, the CFD inhibitor is Compound 18. In one embodiment, the CFD inhibitor is Compound 19. In one embodiment, the CFD inhibitor is Compound 20. In one embodiment, the CFD inhibitor is Compound 21. In one embodiment, the CFD inhibitor is Compound 22. In one embodiment, the CFD inhibitor is Compound 23. In one embodiment, the CFD inhibitor is Compound 24. In one embodiment, the CFD inhibitor is Compound 25. In one embodiment, 100 mg of Compound 1 is administered three times a day. In one embodiment 150 mg of Compound 1 is administered three times a day. In one embodiment, 200 mg of Compound 1 is administered three times a day.

Accordingly, in one embodiment of the present invention, provided herein is a method of treating a subject with PNH comprising:
 a. administering to the subject an effective amount of a C5 inhibitor;
 b. monitoring the subject for the development of extravascular hemolysis; and,
 c. upon the development of extravascular hemolysis, administering to the subject an effective amount of a compound selected from Formula I or Formula II. The ability to administer a CFD inhibitor described herein upon the development of extravascular hemolysis while receiving a C5 inhibitor provides an effective therapeutic agent switching strategy, extending the effectiveness of the C5 inhibitor and providing additional therapeutic options for subjects with PNH showing suboptimal response to the C5 inhibitor. Determining the presence of extravascular hemolysis is well known in the art. For example, PNH subjects suffering from extravascular hemolysis may experience persistent lowered hemoglobin levels while having LDH levels return to normal upon administration of a C5 inhibitor. By monitoring a subject's hemoglobin and LDH levels while receiving a C5 inhibitor, for example eculizumab, the development of extravascular hemolysis can be detected, and the subject administered a CFD inhibitor selected from Formula I and Formula II. In one embodiment, the subject experiencing extravascular hemolysis is also experiencing intravascular hemolysis.

In another embodiment of the present invention, provided herein is a method of treating a subject with PNH comprising
 a. administering to the subject a therapeutically effective amount of a C5 inhibitor;
 b. monitoring the subject for evidence of incomplete inhibition of intravascular hemolysis or residual intravascular hemolysis; and,
 c. upon evidence of incomplete inhibition of intravascular hemolysis or residual intravascular hemolysis, administering to the subject a therapeutically effective amount of a CFD inhibitor selected from Formula I or Formula II. The ability to administer a CFD inhibitor described herein upon the occurrence of residual intravascular hemolysis while receiving a C5 inhibitor provides an effective synergistic therapeutic regimen, extending the effectiveness of the C5 inhibitor and providing additional therapeutic options for subjects with PNH showing suboptimal response to the C5 inhibitor. Determining the presence of residual intravascular hemolysis is well known in the art. For example, PNH subjects suffering from residual or recurrent intravascular hemolysis may have increasing levels of LDH over time, for example greater than or equal to 1.5×ULN (upper limit of normal) for LDH. Likewise, PNH subjects with residual intravascular hemolysis may have decreased levels of hemoglobin in their serum. In one embodiment, a PNH subject receiving a C5 inhibitor is further administered a CFD inhibitor described herein when their serum hemoglobin level is below about 7 g/dL. In one embodiment, a PNH subject receiving a C5 inhibitor is further administered a CFD inhibitor described herein when their serum hemoglobin level below about 8 g/dL. In one embodiment, a PNH subject receiving a C5 inhibitor is further administered a CFD inhibitor described herein when their serum hemoglobin level is below about 9 g/dL. In one embodiment, a PNH subject receiving a C5 inhibitor is further administered a CFD inhibitor described herein when their serum hemoglobin level is below about 10 g/dL. In one embodiment, a PNH subject receiving a C5 inhibitor is further administered a CFD inhibitor described herein when their serum hemoglobin level is below about 15, 14, 13, 12, or 11 g/dL. In an alternative embodiment, the PNH subject is administered an CFD inhibitor upon receiving 4 units of blood in a transfusion within about a 6-month period of time. In one embodiment, the subject is administered a CFD inhibitor if they have a hemoglobin level of below about 10 g/dL and a LDH level of about 140 units per liter (U/L) to 280 U/L following treatment with a C5 inhibitor. In an alternative embodiment, the subject is administered a CFD inhibitor if they have a hemoglobin level of below about 15, 14, 13, 12, or 11 g/dL and a LDH level of about 140 units per liter (U/L) to 280 U/L following treatment with a C5 inhibitor. In one embodiment, the subject is administered a CFD inhibitor if they have a transfusion dependence of about 4 units in 6 months and a LDH level of about 140 units per liter (U/L) to 280 U/L following treatment with a C5 inhibitor.

In an alternative embodiment, a method is provided wherein a subject with PNH with an LDH level greater than or equal to 1.5×ULN (upper limit for normal) for LDH is administered a therapeutically effective amount of a C5 inhibitor and the subject's LDH level decreases, but the subject still has continued anemia as indicated by low hemoglobin levels and/or high transfusion dependence, and the subject is administered a therapeutically effective amount of a CFD inhibitor selected from a compound of Formula I or Formula II, or a pharmaceutically salt thereof.

Methods to measure hemoglobin levels involve standard clinical chemistry protocols that would be known to those of skill in the art. One non-limiting example of a commercially available hemoglobin assay involves reaction of hemoglobin with Triton and sodium hydroxide to form a colorimetric product that is measurable at 400 nm. This assay can measure hemoglobin levels from 0.9 to 200 mg/dl. Additionally, commercially available hemoglobinometers can measure hemoglobin levels by spectrophotometric analysis. Normal hemoglobin levels are considered to be from about 13.5 to about 17.5 g/dL for men and from about 12.0 to about 15.5 g/dL for women. A patient is considered anemic if their hemoglobin levels fall below about 10.0 g/dL.

Methods to measure lactate dehydrogenase (LDH) levels involve standard clinical chemistry protocols that would be known to those of skill in the art. One non-limiting example of a commercially available assay involves reaction of free LDH with NAD) to form NADH, the formed NADH then interacting with a chemical probe to form a colorimetric product that is measurable at 450 nm. This assay can measure LDH levels from 1 to 100 U/L. Normal LDH levels are considered to be less than about 250 U/L, while LDH levels are considered elevated when greater than about 250 U/L. LDH levels are considered highly elevated when greater than about 500 U/L.

The direct Coombs test is a clinical blood test used to detect antibodies or complement proteins bound to the surface of red blood cells that would be known to those of skill in the art. In a typical protocol, a blood sample is taken and the red blood cells (RBCs) are washed to remove the patient's own plasma. The RBCs are then incubated with anti-human globulin ("Coombs reagent"). If agglutination of the RBCs occurs, then the direct Coombs test is positive, indicative of the presence of antibodies or complement proteins bound to the surface of the RBCs.

C3 fragment deposition is measured using blood by flow cytometry that would be known to those of skill in the art. In a typical protocol, a blood sample is collected from eculizumab-treated PNH patients or healthy individuals. Erythrocytes are harvested by centrifugation, washed with PBS several times until the supernatant remains clear. C3 fragment deposition on the PNH erythrocytes membrane is measured by flow cytometry using FITC-conjugated anti-C3c, PE conjugated anti-CD47 and APC-conjugated anti-CD59 following dilution of reaction mixtures in FC buffer. Intact and fragmented PNH erythrocytes are identified by anti-CD47 (positive) and anti-CD59 (negative) staining. C3 fragment deposition is assessed by anti-C3c staining.

Also provided herein is a method of treating a subject with PNH comprising administering to the subject a therapeutically effective amount of a CFD inhibitor selected from Formula I or Formula II in combination with a C3 inhibitor. As described further below, the use of a CFD inhibitor selected from Formula I or Formula II in combination with a complement component C3 inhibitor also provides for synergistic inhibition of hemolysis of PNH erythrocytes. These synergistic effects provide for increased therapeutic efficacy in the treatment of PNH, while reducing the required amount of inhibitor necessary for therapeutic efficacy. In a particular embodiment, the C3 inhibitor is selected from compstatin or a compstatin analog or derivative. In a particular embodiment, the C3 inhibitor is compstatin. In a particular embodiment, the C3 inhibitor is the compstatin analog 4(1MeW)/APL-1. In a particular embodiment, the C3 inhibitor is the compstatin analog CP-40. In a particular embodiment, the C3 inhibitor is the compstatin analog Peg-CP-40. 4(1MeW), CP40/AMY-101, and Peg-CP-40 are described in Risitano, Ricklin et al., Peptide inhibitors of C3 activation as a novel strategy of complement inhibition for the treatment of paroxysmal nocturnal hemoglobinuria, Blood. 2014 Mar. 27; 123(13):2094-101, incorporated herein by reference. In a particular embodiment, the C3 inhibitor is AMY-201 (Amyndas Pharmaceuticals). In a particular embodiment, the C3 inhibitor is APL-2 (Apellis Pharmaceuticals). In a particular embodiment, the C3 inhibitor is ATA (aurin tricarboxylic acid) (Aurin Biotech, US Pat Appl Pub US20130035392, incorporated herein by reference).

Further provided herein is a method of treating a subject with PNH comprising administering to the subject a therapeutically effective amount of a CFD inhibitor selected from Formula I or Formula II in combination with a complement factor B inhibitor. By targeting multiple mechanisms of complement inhibition, it is believed that the use of a Formula I or Formula II in combination with a factor B inhibitor provides for improved inhibition of hemolysis of PNH erythrocytes, allowing for increased therapeutic efficacy in the treatment of PNH, while reducing the required amount of inhibitor necessary for therapeutic efficacy. In a particular embodiment, the CFB inhibitor is LNP023 (Novartis). In a particular embodiment, the CFB inhibitor is selected from an inhibitor described in WO2013/192345, incorporated by reference herein. In a particular embodiment, the CFB inhibitor is

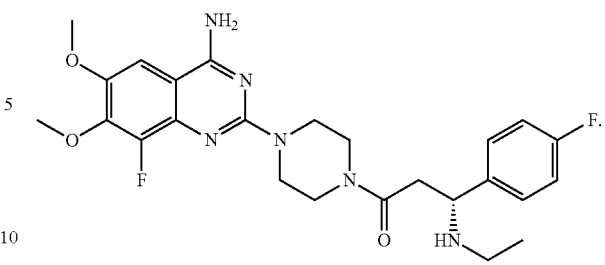

In a particular embodiment, the CFB inhibitor is selected from an inhibitor described in International Application No. PCT/US17/39587, incorporated herein by reference.

In a further aspect, provided herein is a method of treating a subject with PNH comprising administering to the subject a therapeutically effective amount of a CFD inhibitor selected from Formula I or Formula II in combination with a pan-inhibitor to complement components. In one embodiment, the inhibitor is FUT-175.

In particular embodiments, Compound 1 can be administered once a day, twice a day, or three times a day. In some embodiments, Compound 1 can be administered in a 100 mg, 150 mg, or 200 mg dose. In one embodiment, Compound 1 is administered in a 100 mg dose three times a day. In one embodiment, Compound 1 is administered in a 150 mg dose three times a day. In one embodiment, Compound 1 is administered in a 200 mg dose three times a day. In particular embodiments, 100 mg of Compound 1 is administered three times a day in combination or alternation with a C5 inhibitor. In particular embodiments, 150 mg of Compound 1 is administered three times a day in combination or alternation with a C5 inhibitor. In particular embodiments, 200 mg of Compound 1 is administered three times a day in combination or alternation with C5 inhibitor. In particular embodiments, 100 mg of Compound 1 is administered three times a day in combination or alternation with eculizamab. In particular embodiments, 150 mg of Compound 1 is administered three times a day in combination or alternation with eculizamab. In particular embodiments, 200 mg of Compound 1 is administered three times a day in combination or alternation with eculizamab.

Pharmaceutical Compositions and Dosage Forms

A CFD inhibitor described herein, or its salt, isotopic analog, or prodrug can be administered in an effective amount to a host to treat any of the disorders described herein using any suitable approach which achieves the desired therapeutic result. The amount and timing of active compound administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

The therapeutically effective dosage of any active compound described herein will be determined by the health care practitioner depending on the condition, size and age of the subject as well as the route of delivery. In one non-limited embodiment, a dosage from about 0.1 to about 200 mg/kg has therapeutic efficacy, with all weights being calculated based upon the weight of the active compound, including the cases where a salt is employed. In one embodiment, the dosage is at about or greater than 0.1, 0.5, 1, 5, 10, 25, 50, 75, 100, 125, 150, 175, or 200 mg/kg. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 M.

In certain embodiments, the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples include dosage forms with at least 5, 10, 15, 20, 25, 50, 100, 200, 250, 300, 400, 500, 600, 700, or 750 mg of active compound, or its salt. The pharmaceutical composition may also include a molar ratio of the active compound and an additional active agent, in a ratio that achieves the desired results.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intramuscular, inhalation, intra-aortal, intracranial, subdermal, intraperitoneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

In accordance with the presently disclosed methods, an oral administration can be in any desired form such as a solid, gel or liquid, including a solution, suspension, or emulsion. In some embodiments, the compounds or salts are administered by inhalation, intravenously, or intramuscularly as a liposomal suspension. When administered through inhalation the active compound or salt may be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise an active compound described herein or a pharmaceutically acceptable salt thereof, in any pharmaceutically acceptable carrier. If a solution is desired, water may sometimes be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

Carriers include excipients and diluents and must be of sufficiently high purity and sufficiently low toxicity to render them suitable for administration to the subject being treated. The carrier can be inert or it can possess pharmaceutical benefits of its own. The amount of carrier employed in conjunction with the Compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a subject through a needle or a catheter, propelled by a sterile syringe or some other mechanical device such as a continuous infusion system. A formulation provided by the disclosure can be administered using a syringe, injector, pump, or any other device recognized in the art for parenteral administration.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration, a pharmaceutical composition can take the form of a solution suspension, tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the Compound 1 is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In one embodiment, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

EXAMPLES

Figure 1B:
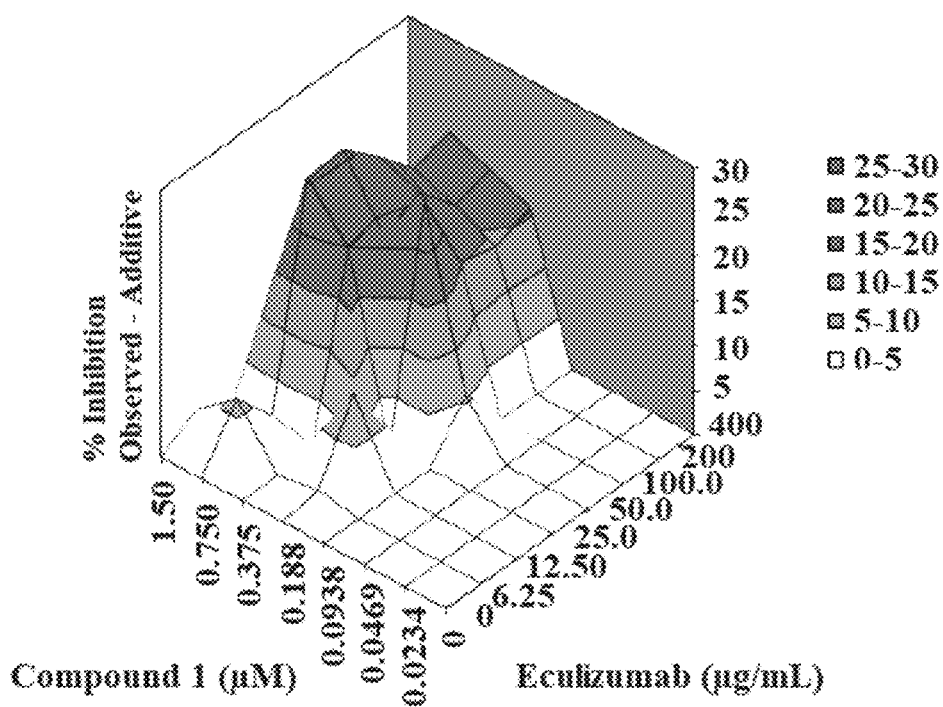

Example 1. Inhibitory Activity of Compound 1 in Combination with Eculizumab as Assessed Via a CAP-Mediated Hemolysis Assay with PNH Erythrocytes The inhibitory activity of Compound 1 and the humanized monoclonal antibody Eculizumab was assessed via a CAP-mediated hemolysis assay with PNH erythrocytes from subjects (described in Example 3). The CAP-mediated hemolysis assay with PNH erythrocytes was conducted two independent times and then analyzed by the method of Prichard and Shipman (described in Example 4). The inhibition of CAP activity for each experiment is shown in Table 2. The analytical results for each experiment, along with summary information, are shown in Table 3. The three-dimensional surface-graphs used in the analysis method of Prichard and Shipman are shown in FIGS. 1A-1B.

TABLE 2

Inhibition of CAP activity of Compound 1 and Eculizumab

| Eculi-zumab[a] | Compound 1 (µM) Inhibition (%), Experiment #1 | | | | | | | |
|---|---|---|---|---|---|---|---|---|
| | 0 | 0.0234 | 0.0469 | 0.0938 | 0.188 | 0.375 | 0.75 | 1.5 |
| 400 | 34 | 37 | 35 | 36 | 56 | 76 | 91 | 97 |
| 200 | 25 | 31 | 29 | 31 | 55 | 70 | 88 | 98 |
| 100 | 12 | 25 | 18 | 23 | 41 | 64 | 87 | 97 |
| 50 | 7 | 32 | 16 | 20 | 40 | 65 | 86 | 97 |
| 25 | 6 | 14 | 13 | 15 | 25 | 44 | 72 | 91 |
| 12.5 | 0 | 3 | 0 | 0 | 8 | 22 | 55 | 86 |
| 6.25 | 0 | 1 | 0 | 0 | 9 | 21 | 54 | 87 |
| 0 | 0 | 4 | 2 | 6 | 14 | 24 | 55 | 86 |

| | Inhibition (%), Experiment 2 | | | | | | | |
|---|---|---|---|---|---|---|---|---|
| | 0 | 0.0234 | 0.0469 | 0.0938 | 0.188 | 0.375 | 0.75 | 1.5 |
| 400 | 38 | 45 | 42 | 43 | 59 | 81 | 89 | 96 |
| 200 | 30 | 39 | 36 | 34 | 50 | 77 | 86 | 94 |
| 100 | 24 | 38 | 32 | 31 | 49 | 75 | 83 | 93 |
| 50 | 20 | 28 | 24 | 26 | 51 | 73 | 82 | 94 |
| 25 | 3 | 15 | 0 | 1 | 33 | 64 | 75 | 90 |
| 12.5 | 0 | 4 | 0 | 0 | 22 | 44 | 53 | 82 |
| 6.25 | 0 | 0 | 0 | 0 | 15 | 41 | 52 | 80 |
| 0 | 0 | 0 | 0 | 0 | 7 | 27 | 42 | 77 |

[a]Concentration of Eculizumab measured in µg/m

TABLE 3

Analysis of CAP-inhibition activity of Compound 1 and Eculizumab via the method of Prichard and Shipman Volume (µM · µg/mL · % inhibition)

| Synergy | Antagonism |
|---|---|
| Experiment #1 | |
| 265 | −8 |
| Experiment #2 | |
| 346 | 0 |
| Summary | |
| 306 ± 57 Strongly Synergistic | −4 ± 6 |

As assessed by the method of Prichard and Shipman, Compound 1 and Eculizumab exhibited a strongly synergistic inhibition of CAP activity as indicated by a substantial synergy volume (306+57 µM·g/mL·% inhibition, Table 2) and by the distinct and consistent positive peaks observed on the surface graphs from both independent experiments (FIGS. 1A-1B).

Figure 2A:
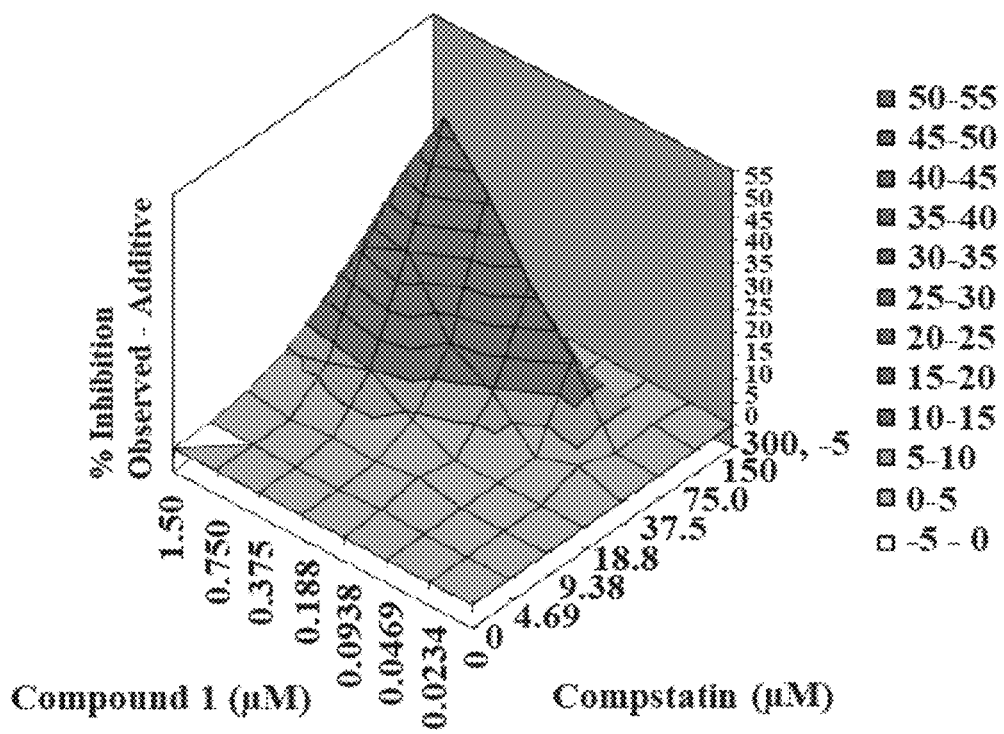
FIGS. 2A-2B are three-dimensional surface graphs showing that the combination of Compound 1 and Compstatin synergistically inhibit complement-mediated hemolysis of PNH erythrocytes. Each of the surface graphs have distinct and consistent positive peaks and as described in Example 2, substantial synergy volume. The concentration of Compstatin (μM) is measured on the x-axis and the concentration of Compound 1 (μM) is measured on the y-axis. The z-axis represents the difference between measured inhibition and a theoretically determined additive inhibition. The positive surface peaks indicate greater inhibition than expected and therefore synergy, while negative surface peaks indicate less inhibition than expected and therefore antagonism.
Figure 2B:
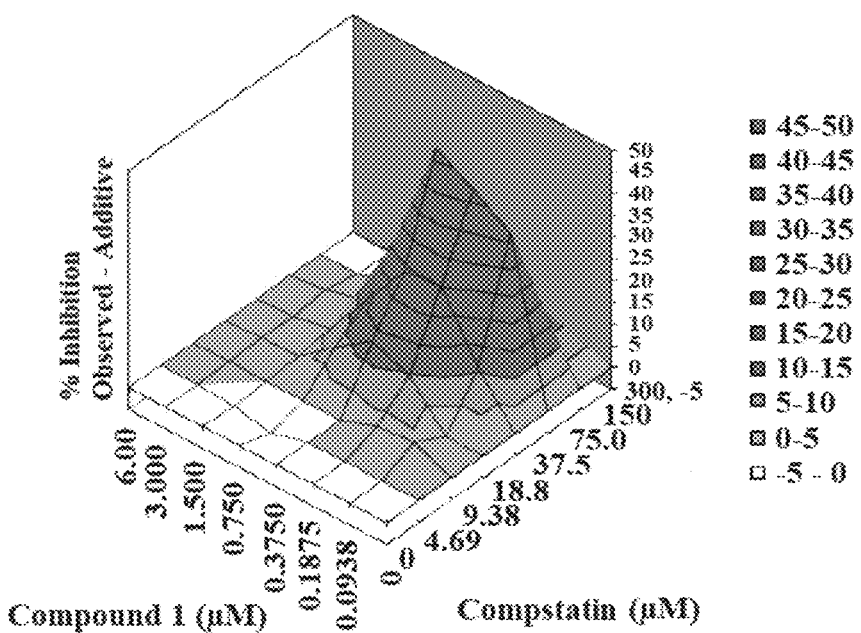
Figure 3A:
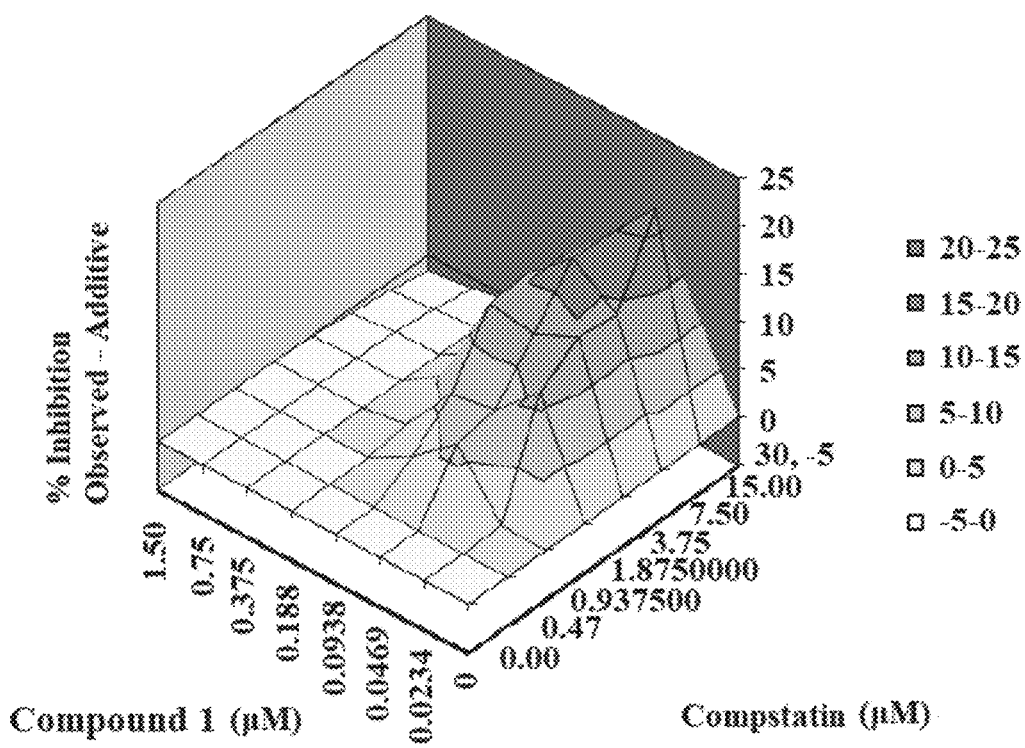
FIGS. 3A-3D are three-dimensional surface graphs showing that the combination of Compound 1 and Compstatin synergistically inhibit CAP activity as measured using hemolysis of rabbit erythrocytes. Each of the surface graphs have distinct and consistent positive peaks and as described in Example 6, substantial synergy volume. The concentration of Compstatin (μM) is measured on the x-axis and the concentration of Compound 1 (μM) is measured on the y-axis. The z-axis represents the difference between measured inhibition and a theoretically determined additive inhibition. The positive surface peaks indicate greater inhibition than expected and therefore synergy, while negative surface peaks indicate less inhibition than expected and therefore antagonism.
Figure 3B:
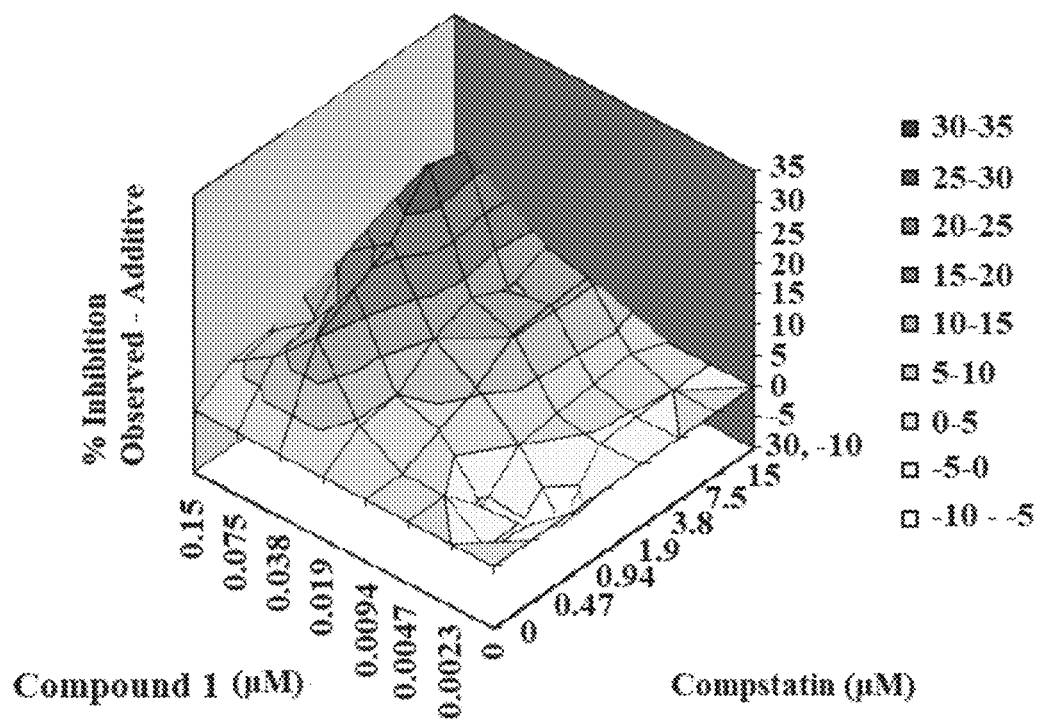
Figure 3C:
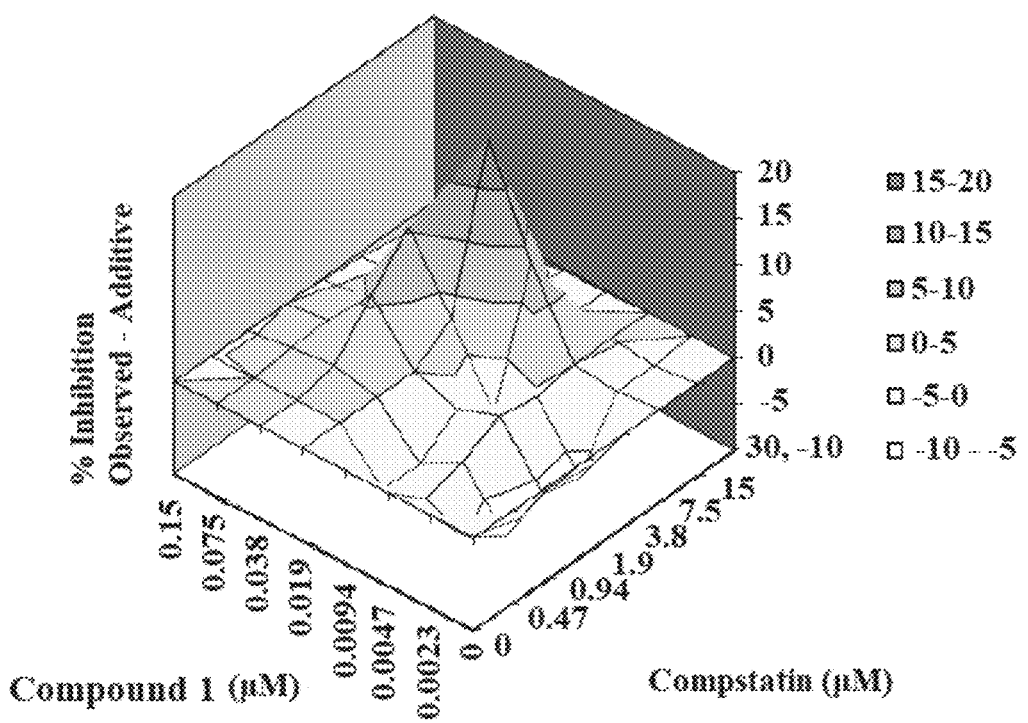
Figure 3D:
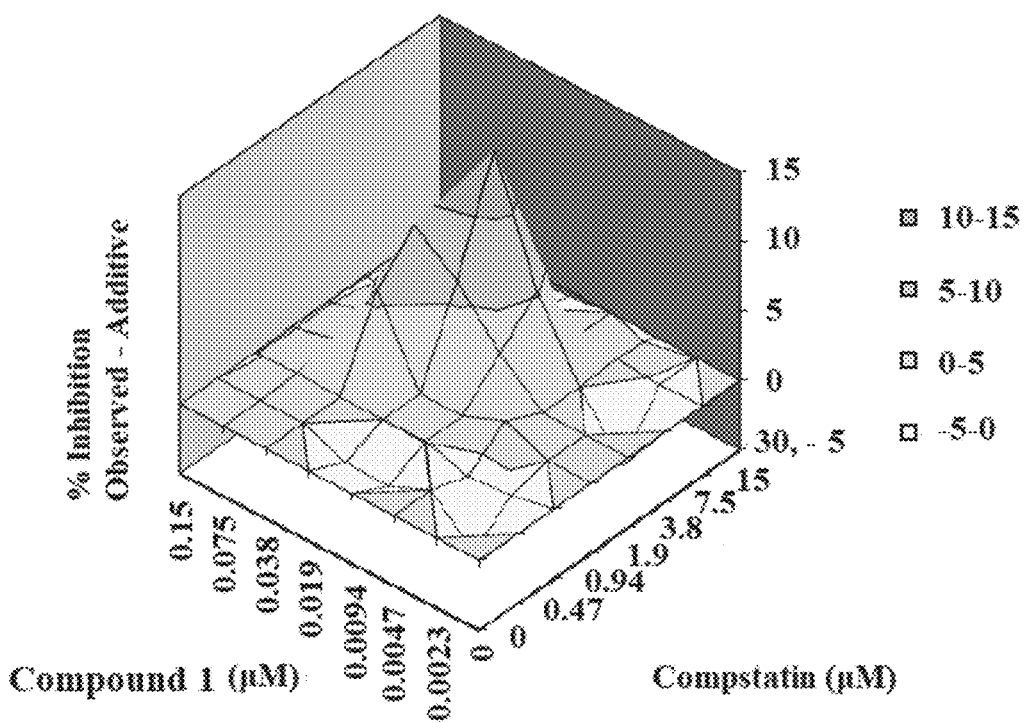

Example 2. Inhibitory Activity of Compound 1 in Combination with Compstatin as Assessed Via a CAP-Mediated Hemolysis Assay with PNH Erythrocytes The inhibitory activity of Compound 1 and the complement C3 inhibitor Compstatin was assessed via a CAP-mediated hemolysis assay with PNH erythrocytes from subjects (described in Example 3). The CAP-mediated hemolysis assay with PNH erythrocytes was conducted two independent times and then analyzed by the method of Prichard and Shipman (described in Example 4) and by the method of Chou and Talalay (described in Example 5). The inhibition of CAP activity for each experiment is shown in Table 4. The analytical results for each experiment are shown in Table 5. The three-dimensional surface-graphs used in the analysis method of Prichard and Shipman are shown in FIGS. 2A-2B.

TABLE 4

Inhibition of CAP activity of Compound 1 and Compstatin measured using the CAP-mediated hemolysis assay with PNH Erythrocytes

| Comp-statin | Compound 1 (µM) Inhibition (%), Experiment #1 | | | | | | | |
|---|---|---|---|---|---|---|---|---|
| (µM) | 0 | 0.0234 | 0.0469 | 0.0938 | 0.1875 | 0.375 | 0.75 | 1.5 |
| 300 | 98 | 99 | 99 | 98 | 99 | 98 | 99 | 99 |
| 150 | 86 | 90 | 87 | 90 | 93 | 96 | 98 | 98 |
| 75 | 9 | 31 | 33 | 44 | 61 | 81 | 92 | 96 |
| 37.5 | 0 | 4 | 3 | 13 | 27 | 50 | 78 | 90 |
| 18.8 | 0 | 0 | 0 | 3 | 16 | 34 | 59 | 85 |
| 9.38 | 0 | 0 | 0 | 3 | 13 | 24 | 50 | 81 |
| 4.69 | 0 | 0 | 0 | 1 | 12 | 23 | 50 | 79 |
| 0 | 0 | 0 | 0 | 0 | 11 | 19 | 51 | 80 |

| | Inhibition (%), Experiment 2 | | | | | | | |
|---|---|---|---|---|---|---|---|---|
| | 0 | 0.0938 | 0.1875 | 0.375 | 0.75 | 1.5 | 3 | 6 |
| 300 | 99 | 99 | 99 | 99 | 99 | 99 | 100 | 99 |
| 150 | 71 | 91 | 95 | 96 | 97 | 98 | 99 | 99 |
| 75 | 10 | 50 | 64 | 83 | 93 | 97 | 99 | 98 |
| 37.5 | 0 | 16 | 32 | 58 | 82 | 94 | 98 | 98 |
| 18.8 | 0 | 7 | 18 | 41 | 73 | 92 | 97 | 98 |
| 9.38 | 0 | 4 | 13 | 34 | 68 | 90 | 97 | 98 |
| 4.69 | 0 | 1 | 5 | 32 | 60 | 88 | 96 | 97 |
| 0 | 0 | 0 | 0 | 6 | 27 | 65 | 90 | 97 | 97 |

TABLE 5

Analysis of CAP-inhibition activity of Compound 1 and Compstatin

| Experiment 1 | | | | | |
|---|---|---|---|---|---|
| Prichard and Shipman | | Chou and Talalay | | | |
| Volume (µM$^2$ · % inhibition) | | Molar Ratio | CI at % inhibition Level | | |
| Synergy | Antagonism | | 50% | 75% | 90% |
| 325 | −1 | 0.0100 | 0.73 | 0.70 | 0.72 |
| | | 0.0050 | 0.77 | 0.78 | 0.83 |
| | | 0.0025 | 0.95 | 0.89 | 0.87 |
| Experiment 2 | | | | | |
| Prichard and Shipman | | Chou and Talalay | | | |
| Volume (µM$^2$ · % inhibition) | | Molar Ratio | CI at % inhibition Level | | |
| Synergy | Antagonism | | 50% | 75% | 90% |
| 324 | −4 | 0.0100 | 0.75 | 0.78 | 0.82 |
| | | 0.0050 | 0.72 | 0.75 | 0.79 |
| | | 0.0025 | 0.71 | 0.75 | 0.81 |

TABLE 5-continued

Analysis of CAP-inhibition activity of Compound 1 and Compstatin

| Summary | | | | | |
|---|---|---|---|---|---|
| Prichard and Shipman | | Chou and Talalay | | | |
| Volume ± SD (µM$^2$ · % inhibition) | | Molar Ratio of Compd 1 and | CI at % inhibition Level | | |
| Synergy | Antagonism | Compstatin | 50% | 75% | 90% |
| 324 ± 2 Strongly Synergistic | −2 ± 2 | 0.0100 | 0.74 ± 0.02 | 0.74 ± 0.05 | 0.77 ± 0.08 |
| | | 0.0050 | 0.75 ± 0.03 | 0.76 ± 0.02 | 0.81 ± 0.02 |
| | | 0.0025 | 0.83 ± 0.17 | 0.82 ± 0.10 | 0.84 ± 0.04 |

As assessed by the method of Prichard and Shipman, Compound 1 and Compstatin showed a strongly synergistic inhibition of CAP activity as indicated by a substantial synergy volume (324+2 µM$^2$·% inhibition, Table 4) and by the distinct and consistent positive peaks observed on the surface graphs from both independent experiments (FIGS. 2A-2B). No antagonistic interaction was observed.

The interaction was characterized as synergistic when analyzed by the method of Chou and Talalay. Compound 1 and Compstatin showed synergistic interactions when assessed at the 50%, 75% and 90% inhibition level (Table 4). Specifically, the CI values determined at all three inhibition levels fell within the synergistic interval (between 0.7 and 0.85) at all three fixed combination ratios.

Example 3. CAP-Mediated Hemolysis Assay with Erythrocytes from PNH Subject A

Combination studies of Compound 1 with Eculizumab (results are described in Example 1) and Compound 1 with Compstatin (results are described in Example 2) were performed using the CAP-mediated hemolysis assay with erythrocytes from PNH subject A and blood group ABO-compatible serum (NHS-AB, final assay concentration 20%). PNH Subject hematologic characteristics are shown in Table 6.

TABLE 6

| Characteristics of Subject A | |
|---|---|
| Age, Gender | 52, F |
| Blood type | B |
| Erythrocyte clone size Type II/III (%) | 3.1/88 |
| Granulocyte clone size (%) | 99 |
| LDH (U/L) | 293 |
| Hemoglobin (g/dL) | 9.8 |
| Direct Coombs C3 | Pos |
| Direct Coombs IgG | Neg |
| Absolute reticulocyte count (K/cu mm) | 288.3 |
| Start of Eculizumab use | Started March 2011 |

Compound 1 and Compstatin were prepared as 15 mM stocks in DMSO. Eculizumab was obtained as a 10 mg/mL stock in buffered saline. Complement-preserved normal human serum (NHS) from an individual donor of ABO blood group type AB (NHS-AB) was purchase from BioreclamationIVT (Westbury, NY). Gelatin veronal buffer (GVB), pH 7.3, without Ca$^{++}$ and Mg$^{++}$ (GVB$^0$) and 100 mM MgCl$_2$+100 mM EGTA (MgEGTA) were obtained from Complement Technology Inc. (Tyler, TX).

GVB⁰·MgEGTA was prepared by mixing GVB⁰ and 100 mM MgEGTA in a 9:1 ratio. PNH erythrocytes were used within five days of blood collection; before assay cells were collected by centrifugation at 800×g and 4° C. for 3 minutes and resuspended in fresh cold GVB⁰·MgEGTA to a density of 5×10⁸ cells/mL.

For the CAP-mediated hemolysis assay, Compound 1 and Compstatin were prepared individually in seven-point two-fold dilution series at 50× final assay concentration in dimethyl sulfoxide (DMSO) and Eculizumab was prepared in a seven-point two-fold dilution series at 25× final assay concentration in GVB⁰·MgEGTA; an eighth sample was prepared for each test compound containing DMSO or GVB⁰·MgEGTA without compound. Each of the 64 possible pairwise combinations of Compound 1 with Eculizumab or compstatin was tested in duplicate wells. Compound 1 (1 µL), compstatin (1 µL), and Eculizumab (2 µL) at the appropriate dilutions were added to wells of polypropylene V-bottom microtiter plates. 50 µL of NHS-AB was added to each well. The plates were mixed and incubated at room temperature for 5 minutes. 24 µL of this NHS-AB with compound was then transferred to duplicate wells of V-bottom microtiter plates each containing 76 µL GVB⁰·MgEGTA. 20 µL PNH erythrocytes was then added to each well and the plates were sealed, mixed, and incubated at 37° C. for 30 minutes with an added shaking for 15 minutes. The following controls were each included in quadruplicate for ACH-0141 with Eculizumab 1 µL DMSO+120 µL GVB0·MgEGTA (representing background signal); 1 µL DMSO+100 µL GVB⁰·MgEGTA+20 µL PNH cells (no serum, representing 0% CAP-mediated lysis); 1 µL DMSO+76 µL GVB⁰·MgEGTA+24 µL NHS-AB+20 µL PNH cells (no compound, representing 100% CAP-mediated lysis); 1 µL DMSO+76 µL GVB⁰·MgEGTA+24 µL heat-inactivated NHS-AB+20 µL Er (heat inactivated serum, representing 0% CAP-mediated lysis and serum back ground control); and 1 µL DMSO+100 µL $H_2O$+20 µL PNH cells (osmotic lysis, representing maximal lysis). For Compound 1 with compstatin similar controls were included except that 2 µL DMSO was used instead of 1 µL. Following incubation, PNH cells were removed by centrifugation at 800×g and 4° C. for 3 minutes, 100 µL supernatant per well was transferred to flat-bottom clear microtiter plates, and $A_{405}$ of the supernatant was measured in a Molecular Devices Spectramax Plus plate reader.

While cells from most PNH subjects show hemolysis only in serum in which CAP has been activated by mild acidification, erythrocytes from subject A were susceptible to CAP-mediated hemolysis in 20% ABO blood group-compatible serum at neutral pH. Two independent experiments each were conducted for evaluation of Compound 1 in respective pairwise combinations with Eculizumab and with Compstatin. The observed hemolysis in control wells without inhibitor ranged from 63% to 74%.

Compound 1 and Compstatin achieved complete inhibition at the high end of the combination's test concentration ranges, but Eculizumab achieved only 34% and 38% inhibition at its maximal test concentration of 400 µg/mL in two experiments.

Combinatorial interactions were analyzed via two methods. The three-dimensional surface-graphing method of Prichard and Shipman (described in Example 4), which can be conducted independent of inhibition behavior was therefore applicable to the combination of Compound 1 with Eculizumab and Compound 1 with Compstatin. The median-effect plot method of Chou and Talalay (described in Example 5) requires that each compound conform individually to standard inhibitor analysis and therefore was not applicable to combinations of Compound 1 and Eculizumab, but was applicable to combinations of Compound 1 and Compstatin.

Example 4. Analysis of Inhibition Via the Three-Dimensional Surface-Graphing Method of Prichard and Shipman Inhibition was analyzed by the method of Prichard and Shipman (Prichard, M. N. and C. Shipman, Jr. A Three-Dimensional Model to Analyze Drug-Drug Interactions. Antiviral Research 1990, 14: 181-205) Three-dimensional surface graphs of each experiment were generated and analyzed using an Excel spreadsheet program adapted from the MacSynergy II spreadsheet (University of Alabama, Birmingham, AL). The X-axis and Y-axis of each surface graph represent the concentrations of the two test compounds, and the Z-axis represents the difference between measured inhibition and a theoretically determined additive inhibition. For an additive relationship, the surface graph resembles a horizontal plane at Z=0, whereas positive surface peaks indicate greater inhibition than expected and therefore synergy, and negative surface peaks indicate less inhibition than expected and therefore antagonism.

Synergy and antagonism volumes were calculated separately as the summed volumes of peaks respectively above and below the Z=0 plane. Volumes were determined using 95% confidence limits to assure significance. Compounds were categorized as additive for volumes between −25 and 25 $\mu M^2 \cdot \%$ inhibition. Compounds were considered slightly synergistic for volumes between 25 and 50 $\mu M^2 \cdot \%$ inhibition, moderately synergistic for volumes between 50 and 100 $\mu M^2 \cdot \%$ inhibition, and strongly synergistic for volumes greater than 100 $\mu M^2 \cdot \%$ inhibition. Similarly, compounds were considered slightly antagonistic for volumes between −25 and −50 $\mu M^2 \cdot \%$ inhibition, moderately antagonistic for volumes between −50 and −100 $\mu M^2 \cdot \%$ inhibition, and strongly antagonistic for volumes less than −100 $\mu M^2 \cdot \%$ inhibition.

Example 5. Analysis of Inhibition Via the Median-Effect Equation of Chou and Talalay Inhibition was analyzed by the method of Chou and Talalay (Chou, T.-C. and P. Talalay. Analysis of Combined Drug Effects: A New Look at a Very Old Problem. Trends Pharmacol. Sci. 1983, 4: 450-454; Chou, T. C. Theoretical basis, experimental design, and computerized simulation of synergism and antagonism in drug combination studies. Pharmacological Reviews 2006, 58: 621-681). Analysis using the median-effect equation of Chou and Talalay was performed with CompuSyn software (ComboSyn, Inc, Paramus, NJ). Analysis of each experiment was conducted using constant-ratio combinations, in which the ratio of Compound 1 and the second compound remained constant as total concentration varied. Three constant ratios were analyzed in each experiment, centered approximately at the ratio of the individual $IC_{50}$ values for the two compounds and ranging two-fold higher and lower. Within each constant-ratio combination the analysis was limited to five total concentrations, separated by two-fold dilutions and centered at the $IC_{50}$ value of the combination, to exclude inaccuracies inherent in extreme data points of nearly 0% or 100% inhibition. Combination index (CI) values were determined at inhibition values of 50%, 75%, and 90%. Interactions were considered additive for CI values between 0.9 and 1.1.

Interactions were considered slightly synergistic for CI values between 0.85 and 0.9, moderately synergistic for CI values between 0.7 and 0.85; synergistic for CI values between 0.3 and 0.7, and strongly synergistic for CI values between 0.1 and 0.3. Interactions were considered slightly antagonistic for CI values between 1.1 and 1.2, moderately antagonistic for CI values between 1.2 and 1.45; antagonistic for CI values between 1.45 and 3.3, and strongly antagonistic for CI values between 3.3 and 10.

Example 6. Inhibitory Activity of Compound 1 in Combination with Compstatin

The inhibitory activity of Compound 1 against CAP activity in combination with the peptidic C3 inhibitor Compstatin was analyzed using the CAP-mediated hemolysis assay with rabbit erythrocytes. It was determined whether the combination was additive, synergistic, or antagonistic by two analytical methods: the three-dimensional surface-graphing method of Prichard and Shipman (described in Example 4) and the median-effect plot method of Chou and Talalay (described in Example 5).

The CAP-mediated hemolysis assay (described in Example 9) was conducted four independent times and then analyzed by the two methods. The inhibition of CAP activity for each experiment is shown in Table 7 and the analytical results for each experiment are shown in Table 8. The three-dimensional surface-graphs used in the analysis method of Prichard and Shipman are shown in FIGS. 3A-3D.

TABLE 7

Inhibition of CAP activity of Compound 1 and Compstatin measured using the CAP-mediated hemolysis assay

| Compstatin (μM) | Compound 1 (μM) Inhibition (%), Experiment #1 | | | | | | |
|---|---|---|---|---|---|---|---|
| | 0 | 0.0234 | 0.0469 | 0.0938 | 0.188 | 0.375 | 0.75 | 1.5 |
| 30 | 98 | 98 | 98 | 99 | 98 | 98 | 98 | 98 |
| 15 | 65 | 97 | 98 | 99 | 98 | 98 | 98 | 98 |
| 7.5 | 38 | 76 | 88 | 98 | 98 | 98 | 98 | 98 |
| 3.75 | 17 | 59 | 68 | 96 | 97 | 98 | 98 | 98 |
| 1.88 | 8.6 | 49 | 62 | 90 | 96 | 97 | 98 | 98 |
| 0.934 | 3.6 | 42 | 57 | 86 | 94 | 98 | 98 | 98 |
| 0.469 | 7.3 | 29 | 50 | 82 | 92 | 98 | 98 | 98 |
| 0 | 0.0 | 27 | 44 | 75 | 91 | 98 | 98 | 98 |

| | Inhibition (%), Experiment 2 | | | | | | |
|---|---|---|---|---|---|---|---|
| | 0 | 0.00234 | 0.00469 | 0.00938 | 0.0188 | 0.0375 | 0.075 | 0.15 |
| 30 | 98 | 98 | 98 | 98 | 99 | 99 | 99 | 98 |
| 15 | 80 | 79 | 86 | 93 | 97 | 99 | 99 | 99 |
| 7.5 | 41 | 39 | 46 | 56 | 71 | 97 | 98 | 98 |
| 3.75 | 15. | 15 | 24 | 35 | 49 | 88 | 96 | 98 |
| 1.88 | 10 | 0.0 | 10 | 19 | 34 | 75 | 92 | 97 |
| 0.934 | 6.0 | 0.0 | 0.0 | 13 | 29 | 69 | 88 | 96 |
| 0.469 | 6.9 | 0.0 | 2.0 | 12 | 26 | 68 | 85 | 96 |
| 0 | 0.0 | 0.0 | 0.0 | 3.2 | 16 | 45 | 72 | 91 |

| | Inhibition (%), Experiment 3 | | | | | | |
|---|---|---|---|---|---|---|---|
| | 0 | 0.00234 | 0.00469 | 0.00938 | 0.0188 | 0.0375 | 0.075 | 0.15 |
| 30 | 98 | 98 | 98 | 98 | 98 | 98 | 98 | 98 |
| 15 | 97 | 97 | 98 | 98 | 99 | 99 | 99 | 99 |
| 7.5 | 63 | 60 | 67 | 80 | 98 | 99 | 99 | 99 |
| 3.75 | 40 | 35 | 41 | 48 | 74 | 95 | 98 | 98 |
| 1.88 | 25 | 21 | 29 | 37 | 57 | 87 | 98 | 98 |
| 0.934 | 17 | 12 | 18 | 30 | 49 | 81 | 97 | 98 |
| 0.469 | 13 | 8.2 | 13 | 25 | 46 | 76 | 97 | 98 |
| 0 | 0.0 | 3.0 | 7.7 | 22 | 41 | 73 | 96 | 98 |

| | Inhibition (%), Experiment 4 | | | | | | |
|---|---|---|---|---|---|---|---|
| | 0 | 0.00234 | 0.00469 | 0.00938 | 0.0188 | 0.0375 | 0.075 | 0.15 |
| 30 | 99 | 99 | 99 | 98 | 99 | 99 | 99 | 99 |
| 15 | 98 | 97 | 98 | 98 | 99 | 99 | 99 | 99 |
| 7.5 | 64 | 59 | 65 | 77 | 94 | 99 | 99 | 99 |
| 3.75 | 34 | 31 | 40 | 51 | 70 | 97 | 99 | 99 |
| 1.88 | 22 | 15 | 29 | 38 | 54 | 93 | 98 | 99 |
| 0.934 | 12 | 6.8 | 17 | 30 | 46 | 87 | 98 | 99 |
| 0.469 | 9.0 | 5.0 | 11 | 24 | 42 | 83 | 97 | 99 |
| 0 | 0.0 | 0.8 | 7.1 | 20 | 41 | 81 | 97 | 99 |

TABLE 8

Analysis of CAP-inhibition activity of Compound 1 and Compstatin

Experiment 1

| Prichard and Shipman Volume ($\mu M^2 \cdot$ % inhibition) | | Molar Ratio of Compound 1 to | CI at % inhibition Level | | |
|---|---|---|---|---|---|
| Synergy | Antagonism | Compstatin | 50% | 75% | 90% |
| 171 | −7 | 0.0031 | 0.86 | 0.65 | 0.48 |
| | | 0.0063 | 1.03 | 0.70 | 0.47 |
| | | 0.0125 | 0.98 | 0.64 | 0.43 |

Experiment 2

| Prichard and Shipman Volume ($\mu M^2 \cdot$ % inhibition) | | Molar Ratio of Compound 1 to | CI at % inhibition Level | | |
|---|---|---|---|---|---|
| Synergy | Antagonism | Compstatin | 50% | 75% | 90% |
| 339 | −31 | 0.0025 | 1.03 | 0.76 | 0.57 |
| | | 0.0050 | 0.91 | 0.69 | 0.53 |
| | | 0.0100 | 0.78 | 0.62 | 0.50 |

Experiment 3

| Prichard and Shipman Volume ($\mu M^2 \cdot$ % inhibition) | | Molar Ratio of Compound 1 to | CI at % inhibition Level | | |
|---|---|---|---|---|---|
| Synergy | Antagonism | Compstatin | 50% | 75% | 90% |
| 58 | −58 | 0.0025 | 1.22 | 0.95 | 0.74 |
| | | 0.0050 | 1.10 | 0.92 | 0.77 |
| | | 0.0100 | 1.14 | 0.97 | 0.84 |

Experiment 4

| Prichard and Shipman Volume ($\mu M^2 \cdot$ % inhibition) | | Molar Ratio of Compound 1 to | CI at % inhibition Level | | |
|---|---|---|---|---|---|
| Synergy | Antagonism | Compstatin | 50% | 75% | 90% |
| 51 | −16 | 0.0025 | 1.30 | 1.10 | 0.93 |
| | | 0.0050 | 1.11 | 0.99 | 0.88 |
| | | 0.0100 | 1.09 | 0.97 | 0.86 |

Summary

| Prichard and Shipman Volume ($\mu M^2 \cdot$ % inhibition) | | Molar Ratio of Compound 1 to | CI at % inhibition Level | | |
|---|---|---|---|---|---|
| Synergy | Antagonism | Compstatin | 50% | 75% | 90% |
| 149 ± 125 Strongly Synergistic | −27 ± 22 | 0.0025 | 1.2 ± 0.1 | 0.94 ± 0.17 | 0.75 ± 0.18 |
| | | 0.0050 | 1.0 ± 0.1 | 0.87 ± 0.15 | 0.72 ± 0.18 |
| | | 0.0100 | 1.0 ± 0.2 | 0.85 ± 0.20 | 0.73 ± 0.20 |

[a] CI values were excluded from the Summary results

As assessed by the method of Prichard and Shipman, Compound 1 and Compstatin showed a strongly synergistic inhibition of CAP activity as indicated by a substantial synergy volume (149±125 $\mu M2 \cdot$% inhibition, Table 8) and by the distinct and consistent positive peaks observed on the surface graphs from all four independent experiments (FIGS. 3A-3D). Without wishing to be bound to any one theory, the antagonism volumes in these four experiments also suggests a slightly antagonistic relationship (−27±22 $\mu M2 \cdot$% inhibition, Table 8), although the dispersed and inconsistent appearance of the negative volumes across the four experiments might have been an experimental artifact.

The interaction was characterized as additive (synergistic to slightly antagonistic) when analyzed by the method of Chou and Talalay. The analysis was conducted on three of the four experiments, with experiment 1 excluded from the average CI values for having too few data points in the prescribed concentration ranges. Compound 1 and Compstatin showed primarily additive interactions, particularly when assessed at the 50% inhibition level (CI=1.0±0.1 at the molar ratio of 0.0050, Table 8). Synergy was observed at 75% and 90% inhibition levels.

Example 7. Inhibitory Activity of Compound 1 in Combination with Anti-C5

The inhibitory activity of Compound 1 against CAP activity in combination with the monoclonal antibody inhibitor of complement C5 was analyzed using the CAP Wieslab assay (described in Example 10). The CAP-mediated hemolysis assay could not be used because the antibody had previously shown insufficient activity in the hemolysis assay for use in combination experiments. It was determined whether the combination was additive, synergistic, or antagonistic by two analytical methods: the three-dimensional surface-graphing method of Prichard and Shipman (described in Example 4) and the median-effect plot method of Chou and Talalay (described in Example 5).

Figure 4A:
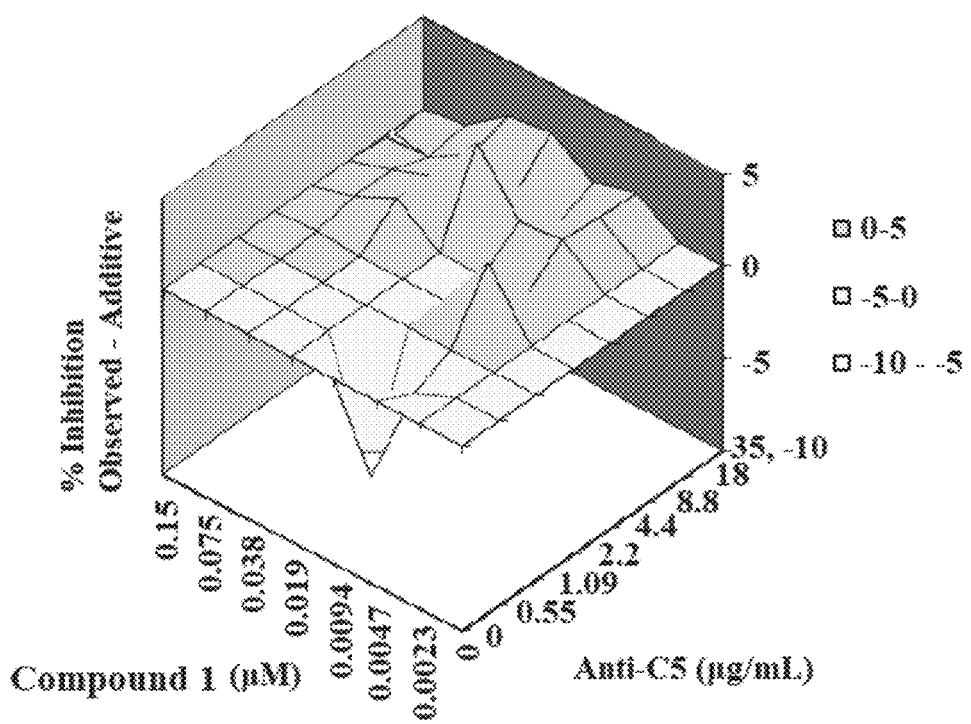
FIGS. 4A-4C are the three-dimensional surface graphs showing that the combination of Compound 1 and anti-C5 (murine monoclonal antibody to human C5, isotype IgG1K, product No. A217 from Quidel, San Diego, CA) are moderate synergistic inhibitors of CAP activity as measured using the Wieslab ELISA-based functional assay. Each of the surface graphs have distinct positive peaks and as described in Example 7, synergy volume. The concentration of anti-C5 (μg/mL) is measured on the x-axis and the concentration of Compound 1 (μM) is measured on the y-axis. The z-axis represents the difference between measured inhibition and a theoretically determined additive inhibition. The positive surface peaks indicate greater inhibition than expected and therefore synergy.
Figure 4B:
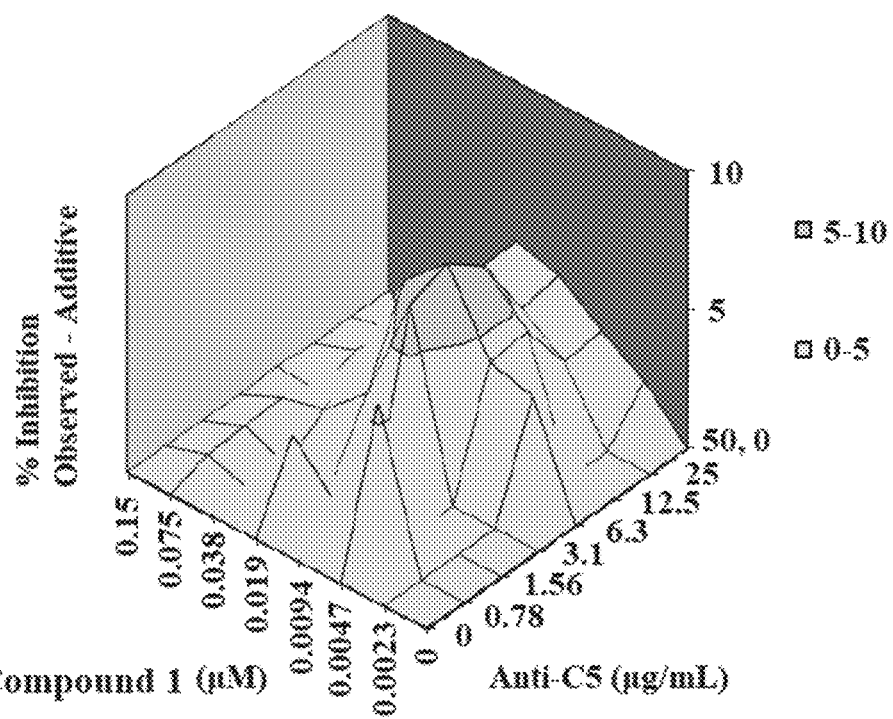
Figure 4C:
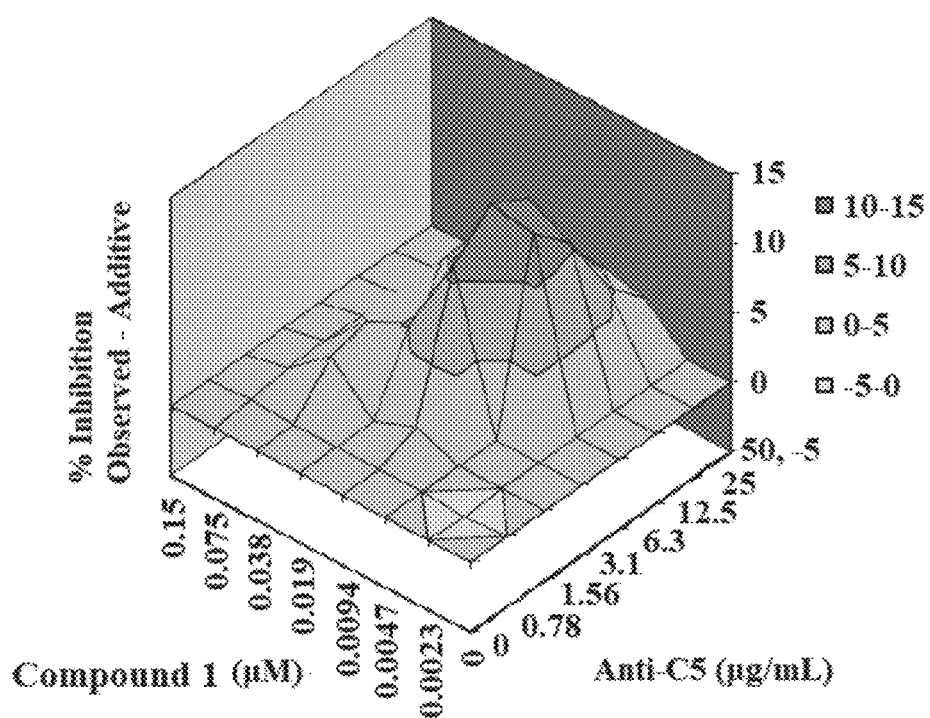

The CAP Wieslab assay (described in Example 10) was conducted three independent times and then analyzed by the two methods. The inhibition of CAP activity for each experiment is shown in Table 9 and the analytical results for each experiment are shown in Table 10. The three-dimensional surface-graphs used in the analysis method of Prichard and Shipman are shown in FIGS. 4A-4C.

TABLE 9

Inhibition of CAP activity of Compound 1 and Anti-C5 measured using the CAP Wieslab assay

| Anti-C5[a] | Compound 1 (μM) Inhibition (%), Experiment #1 | | | | | | | |
|---|---|---|---|---|---|---|---|---|
| | 0 | 0.00234 | 0.00469 | 0.0093 | 0.0188 | 0.0375 | 0.075 | 0.15 |
| 35 | 87 | 88 | 91 | 93 | 96 | 99 | 100 | 100 |
| 17.5 | 76 | 76 | 84 | 85 | 90 | 98 | 100 | 100 |
| 8.75 | 60 | 58 | 71 | 77 | 84 | 96 | 100 | 100 |
| 4.38 | 47 | 39 | 56 | 65 | 74 | 92 | 99 | 100 |
| 2.19 | 27 | 31 | 41 | 53 | 63 | 87 | 99 | 100 |
| 1.09 | 11 | 8.2 | 21 | 33 | 48 | 80 | 98 | 100 |
| 0.547 | 11 | 6.7 | 21 | 34 | 47 | 78 | 98 | 100 |
| 0 | 0.0 | 0.0 | 14 | 33 | 42 | 78 | 97 | 100 |

| | Inhibition (%), Experiment 2 | | | | | | | |
|---|---|---|---|---|---|---|---|---|
| | 0 | 0.00234 | 0.00469 | 0.00938 | 0.0188 | 0.0375 | 0.075 | 0.15 |
| 50 | 90 | 93 | 94 | 96 | 98 | 99 | 100 | 100 |
| 25 | 85 | 87 | 90 | 92 | 94 | 98 | 100 | 100 |
| 12.5 | 75 | 78 | 83 | 87 | 88 | 96 | 100 | 100 |
| 6.25 | 61 | 68 | 72 | 76 | 80 | 93 | 97 | 100 |
| 3.13 | 46 | 49 | 56 | 62 | 70 | 89 | 99 | 100 |
| 1.56 | 20 | 23 | 28 | 35 | 49 | 81 | 98 | 100 |
| 0.781 | 8.1 | 14 | 22 | 26 | 45 | 77 | 98 | 100 |
| 0.0 | 0 | 5.6 | 8.9 | 17 | 30 | 72 | 97 | 100 |

| | Inhibition (%), Experiment 3 | | | | | | | |
|---|---|---|---|---|---|---|---|---|
| | 0 | 0.00234 | 0.00469 | 0.00938 | 0.0188 | 0.037 | 0.075 | 0.15 |
| 50 | 90 | 92 | 95 | 97 | 99 | 100 | 100 | 100 |
| 25 | 79 | 84 | 90 | 93 | 96 | 99 | 100 | 100 |
| 12.5 | 64 | 68 | 81 | 87 | 92 | 98 | 100 | 100 |
| 6.25 | 45 | 52 | 71 | 75 | 87 | 86 | 100 | 100 |
| 3.13 | 31 | 34 | 53 | 68 | 78 | 94 | 100 | 100 |
| 1.56 | 16 | 3.8 | 27 | 47 | 62 | 91 | 99 | 100 |
| 0.781 | 10 | 1.8 | 19 | 39 | 55 | 87 | 99 | 100 |
| 0.0 | 0.0 | 0.0 | 12 | 30 | 48 | 81 | 98 | 100 |

[a]Concentration of Anti-C5 measured in μg/mL

TABLE 10

Analysis of CAP-inhibition activity of Compound 1 and Anti-C5

| Experiment 1 | | | | | |
|---|---|---|---|---|---|
| Prichard and Shipman | | Chou and Talalay[a] | | | |
| Volume (μM · μg/mL · % inhibition) | | Molar Ratio of Compound 1 to Anti-C5 | CI at % inhibition Level | | |
| Synergy | Antagonism | | 50% | 75% | 90% |
| 26 | −8 | 0.16 | 0.95 | 0.85 | 0.82 |
| | | 0.32 | 1.03 | 0.81 | 0.68 |
| | | 0.64 | 1.00 | 0.88 | 0.83 |

| Experiment 2 | | | | | |
|---|---|---|---|---|---|
| Prichard and Shipman | | Chou and Talalay[a] | | | |
| Volume (μM · μg/mL · % inhibition) | | Molar Ratio of Compound 1 to Anti-C5 | CI at % inhibition Level | | |
| Synergy | Antagonism | | 50% | 75% | 90% |
| 88 | 0 | 0.23 | 0.90 | 0.83 | 0.81 |
| | | 0.45 | 0.93 | 0.81 | 0.75 |
| | | 0.90 | 1.04 | 0.95 | 0.91 |

TABLE 10-continued

Analysis of CAP-inhibition activity of Compound 1 and Anti-C5

| Experiment 3 | | | | | |
|---|---|---|---|---|---|
| Prichard and Shipman | | Chou and Talalay[a] | | | |
| Volume (μM · μg/mL · % inhibition) | | Molar Ratio of Compound 1 to Anti-C5 | CI at % inhibition Level | | |
| Synergy | Antagonism | | 50% | 75% | 90% |
| 128 | −1 | 0.23 | 1.06 | 0.78 | 0.62 |
| | | 0.45 | 0.99 | 0.78 | 0.66 |
| | | 0.90 | 1.00 | 1.14 | 1.36 |

| Summary | | | | | |
|---|---|---|---|---|---|
| Prichard and Shipman | | Chou and Talalay | | | |
| Volume (μM² · % inhibition) | | Molar Ratio of Compound 1 to Anti-C5[a] | CI at % inhibition Level | | |
| Synergy | Antagonism | | 50% | 75% | 90% |
| 81 ± 51 Synergistic | −3 ± 4 | 0.23 | 0.97 ± 0.09 | 0.82 ± 0.03 | 0.75 ± 0.11 |
| | | 0.45 | 0.98 ± 0.05 | 0.80 ± 0.02 | 0.70 ± 0.05 |

TABLE 10-continued

Analysis of CAP-inhibition activity of Compound 1 and Anti-C5

| | | | |
|---|---|---|---|
| 0.90 | 1.0 ± 0.0 | 0.99 ± 0.13 | 1.0 ± 0.30 |

[a] Molar Ratios of Compound 1 to Anti-C5 were 0.16, 0.32, and 0.64 in Experiment 1

As assessed by the method of Prichard and Shipman, Compound 1 and anti-C5 showed synergistic inhibition of CAP activity as indicated by synergy volume (81±51 μM·μg/mL·% inhibition, Table 10) and by the distinct positive peak evident on the surface graphs from the three experiments (FIGS. 4A-4C). No antagonistic interaction was observed.

The interaction was characterized as additive (synergistic to additive) when characterized by the method of Chou and Talaly. Compound 1 and anti-C5 showed primarily additive interactions, particularly when assessed at the 50% inhibition level (CI=0.98±0.05 at the molar ratio of 0.45, Table 10). Additive to synergistic interactions were observed at the 75% and 90% inhibition levels.

Example 8. Inhibitory Activity of Compound 1 in Combination with FUT-175

The inhibitory activity of Compound 1 against CAP activity in combination with the broad-spectrum complement inhibitor FUT-175 was analyzed using the CAP-mediated hemolysis assay. It was determined whether the combination was additive, synergistic, or antagonistic by two analytical methods: the three-dimensional surface-graphing method of Prichard and Shipman (described in Example 4) and the median-effect plot method of Chou and Talalay (described in Example 5).

Figure 5A:
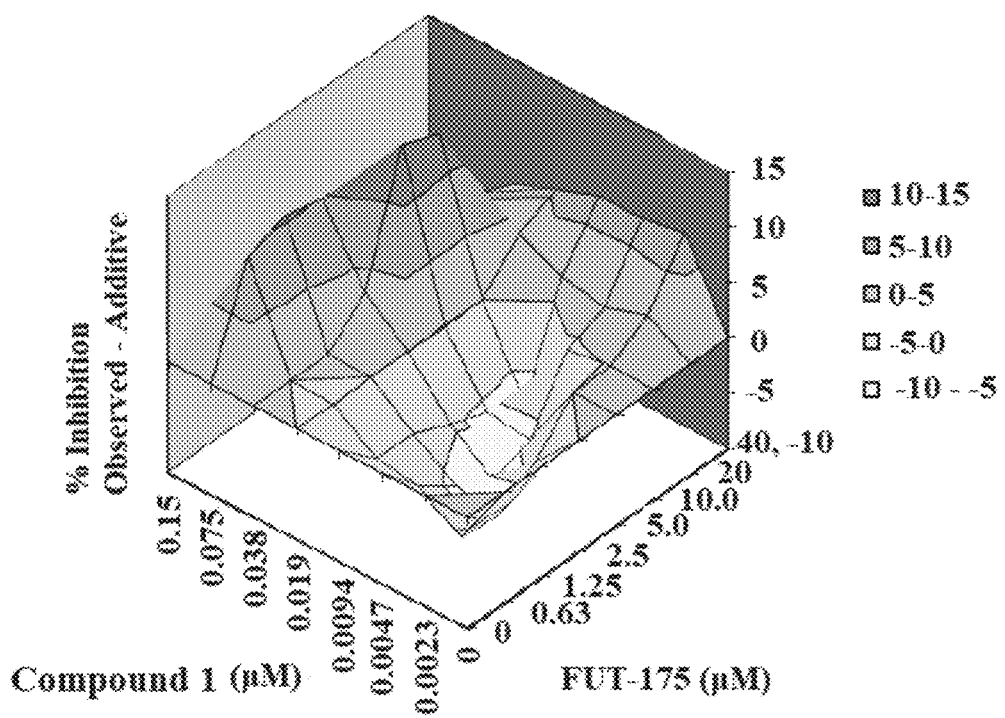
FIGS. 5A-5C are the three-dimensional surface graphs showing that the combination of Compound 1 and FUT-175 are moderate synergistic inhibitors of CAP activity as measured using hemolysis of rabbit erythrocytes. Each of the surface graphs have distinct positive peaks and as described in Example 8, synergy volume. The concentration of FUT-175 (μM) is measured on the x-axis and the concentration of Compound 1 (μM) is measured on the y-axis. The z-axis represents the difference between measured inhibition and a theoretically determined additive inhibition. The positive surface peaks indicate greater inhibition than expected and therefore synergy, while negative surface peaks indicate less inhibition than expected and therefore antagonism.
Figure 5B:
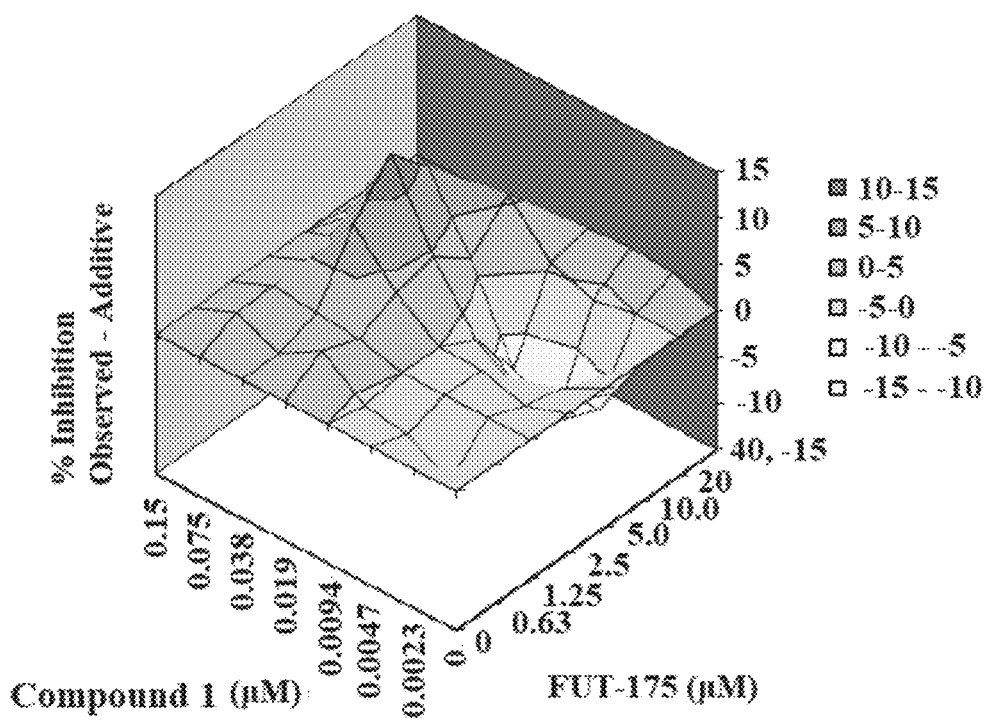
Figure 5C:
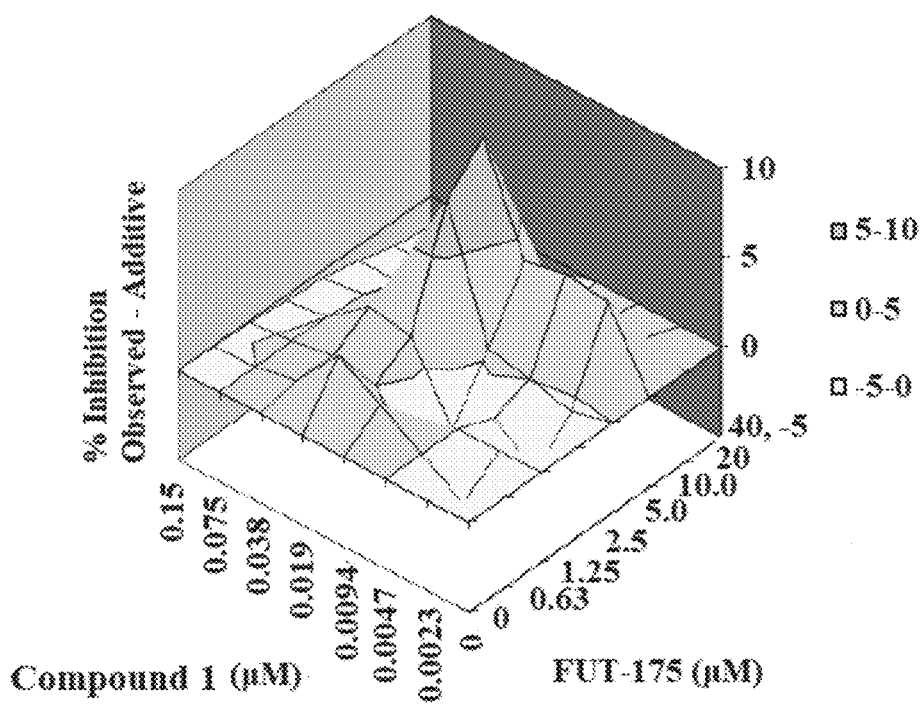

The CAP-mediated hemolysis assay (described in Example 9) was conducted three independent times and then analyzed by the two analytical methods. The inhibition of CAP activity for each experiment is shown in Table 11 and the analytical results for each experiment are shown in Table 12. The three-dimensional surface-graphs used in the analysis method of Prichard and Shipman are shown in FIGS. 5A-5C.

TABLE 11

Inhibition of CAP activity of Compound 1 and FUT-175 measured using the CAP-mediated hemolysis assay

| FUT-175 | Compound 1 (μM) | | | | | | | |
|---|---|---|---|---|---|---|---|---|
| | Inhibition (%), Experiment #1 | | | | | | | |
| (μM) | 0 | 0.00234 | 0.00469 | 0.0093 | 0.0188 | 0.0375 | 0.075 | 0.15 |
| 40 | 90 | 98 | 98 | 98 | 98 | 98 | 98 | 98 |
| 20 | 87 | 92 | 89 | 92 | 96 | 98 | 98 | 97 |
| 10 | 67 | 74 | 64 | 64 | 77 | 95 | 98 | 98 |
| 5 | 41 | 40 | 39 | 42 | 56 | 83 | 97 | 98 |
| 2.5 | 26 | 22 | 24 | 31 | 46 | 70 | 96 | 98 |
| 1.25 | 17 | 14 | 16 | 24 | 40 | 60 | 95 | 98 |
| 0.625 | 12 | 9.6 | 11 | 20 | 37 | 50 | 93 | 98 |
| 0 | 0.0 | 4.5 | 8.3 | 16 | 31 | 44 | 79 | 96 |

| | Inhibition (%), Experiment 2 | | | | | | | |
|---|---|---|---|---|---|---|---|---|
| | 0 | 0.00234 | 0.00469 | 0.00938 | 0.0188 | 0.0375 | 0.075 | 0.15 |
| 40 | 96 | 98 | 98 | 98 | 98 | 98 | 98 | 98 |
| 20 | 84 | 83 | 83 | 88 | 95 | 98 | 98 | 98 |
| 10 | 60 | 49 | 50 | 57 | 75 | 97 | 98 | 98 |
| 5 | 29 | 25 | 28 | 36 | 56 | 92 | 98 | 98 |
| 2.5 | 14 | 15 | 18 | 26 | 46 | 86 | 97 | 98 |
| 1.25 | 7.0 | 10 | 13 | 20 | 41 | 80 | 97 | 98 |
| 0.625 | 7.7 | 7.7 | 11 | 18 | 39 | 77 | 97 | 98 |
| 0 | 0.0 | 5.0 | 7.0 | 13 | 31 | 70 | 95 | 98 |

| | Inhibition (%), Experiment 3 | | | | | | | |
|---|---|---|---|---|---|---|---|---|
| | 0 | 0.00234 | 0.00469 | 0.00938 | 0.0188 | 0.037 | 0.075 | 0.15 |
| 40 | 98 | 98 | 98 | 99 | 98 | 98 | 98 | 98 |
| 20 | 97 | 98 | 98 | 98 | 98 | 98 | 98 | 98 |
| 10 | 67 | 76 | 77 | 84 | 96 | 98 | 98 | 98 |
| 5 | 38 | 43 | 46 | 59 | 85 | 98 | 98 | 98 |
| 2.5 | 23 | 26 | 35 | 45 | 75 | 98 | 98 | 98 |
| 1.25 | 13 | 20 | 25 | 36 | 63 | 96 | 98 | 98 |
| 0.625 | 9.4 | 17 | 23 | 40 | 64 | 96 | 98 | 98 |
| 0 | 0.0 | 11 | 17 | 32 | 54 | 94 | 98 | 98 |

TABLE 12

Analysis of CAP-inhibition activity of Compound 1 and FUT-175

Experiment 1

| Prichard and Shipman | | Chou and Talalay [a] | | | |
|---|---|---|---|---|---|
| Volume ($\mu M^2 \cdot$ % inhibition) | | Molar | CI at % inhibition Level | | |
| Synergy | Antagonism | Ratio | 50% | 75% | 90% |
| 122 | −67 | 0.0019 | 1.10 | 0.75 | 0.52 |
| | | 0.0038 | 0.98 | 0.74 | 0.56 |
| | | 0.0075 | 0.98 | 0.69 | 0.50 |

Experiment 2

| Prichard and Shipman | | Chou and Talalay [a] | | | |
|---|---|---|---|---|---|
| Volume ($\mu M^2 \cdot$ % inhibition) | | Molar | CI at % inhibition Level | | |
| Synergy | Antagonism | Ratio | 50% | 75% | 90% |
| 69 | −52 | 0.0019 | 1.15 | 0.93 | 0.76 |
| | | 0.0038 | 1.01 | 0.86 | 0.74 |
| | | 0.0075 | 1.04 | 0.86 | 0.72 |

Experiment 3

| Prichard and Shipman | | Chou and Talalay [a] | | | |
|---|---|---|---|---|---|
| Volume ($\mu M^2 \cdot$ % inhibition) | | Molar | CI at % inhibition Level | | |
| Synergy | Antagonism | Ratio | 50% | 75% | 90% |
| 42 | −23 | 0.0019 | 1.22 | 1.04 | 0.88 |
| | | 0.0038 | 1.10 | 0.97 | 0.86 |
| | | 0.0075 | 1.18 | 0.96 | 0.77 |

Summary

| Prichard and Shipman Volume ($\mu M^2 \cdot$ % inhibition) | | Molar Ratio of Compound 1 to Anti-C5 [a] | Chou and Talalay CI at % inhibition Level | | |
|---|---|---|---|---|---|
| Synergy | Antagonism | | 50% | 75% | 90% |
| 78 ± 40 Synergistic (Slightly Antagonistic) | −47 ± 22 | 0.0019 | 1.2 ± 0.1 | 0.91 ± 0.15 | 0.72 ± 0.19 |
| | | 0.0038 | 1.0 ± 0.1 | 0.86 ± 0.12 | 0.72 ± 0.15 |
| | | 0.0075 | 1.1 ± 0.1 | 0.84 ± 0.13 | 0.66 ± 0.15 |

As assessed by the method of Prichard and Shipman, Compound 1 and FUT-175 showed synergistic inhibition of CAP activity as indicated by synergy volume (78±40 μM2·% inhibition, Table 12) and by the distinct positive peak evident on the surface graphs from the three experiments (FIGS. 5A-5C). A slightly antagonistic interaction was also suggested by the observed antagonism volume (−47±22 μM2·% inhibition, Table 12), although without committing to any one theory, the dispersed and inconsistent appearance might have been an experimental artifact.

Compound 1 and FUT-175 showed primarily additive interactions by the method of Chou and Talalay, particularly when assessed at the 50% inhibition level (CI=1.0±0.1 at the molar ratio of 0.0038, Table 12). Synergistic to slightly antagonistic interactions were observed at the 75% and 90% inhibition levels.

Example 9. CAP-Mediated Hemolysis Assay

Compound 1 was fully characterized by $^1$H-NMR, HPLC, and mass spectrometry. Compstatin was obtained from Tocris Bioscience (Bristol, UK). The murine monoclonal antibody to human C5, isotype IgG1K, was obtained as product number A217 from Quidel (San Diego, CA). FUT-175 (nafamostat) was obtained from Calbiochem EMD Millipore (Billerica, MA).

Compound 1, FUT-175, and Compstatin were prepared as 10 mM stocks in DMSO. Anti-C5 (murine monoclonal antibody to human C5, isotype IgG1K, product No. A217 from Quidel, San Diego, CA) was obtained as a 1.1 mg/mL stock in buffered saline. Gelatin veronal buffer (GVB) without Ca$^{++}$ and Mg$^{++}$ (GVB$^0$), 100 mM MgCl$_2$+100 mM EGTA (MgEGTA), normal human serum (NHS), and 5×10$^8$/mL rabbit erythrocytes (Er) were obtained from Complement Technology Inc. (Tyler, TX).

GVB$^0$·MgEGTA was prepared by mixing GVB$^0$ and 100 mM MgEGTA in a 9:1 ratio. Er cells were used within two weeks of purchase; before each assay cells were collected by centrifugation at 800×g and 4° C. for 3 minutes and the buffer was replaced with equal volume fresh cold GVB$^0$·MgEGTA.

Compound 1 and a second test compound were prepared individually in seven-point two-fold dilution series at 100× final assay concentration in DMSO, with an eighth sample for each test compound containing DMSO alone. Each of the 64 possible combinations of compounds at varying concentrations was tested in duplicate or triplicate wells. 1.2 μL each of Compound 1 and the second test Compound in the appropriate dilutions were added to wells of polypropylene V-bottom microtiter plates. 50 μL GVB$^0$·MgEGTA was added to each well, followed by 50 μL 20% NHS in GVB$^0$·MgEGTA. The plates were sealed, mixed on a microtiter plate shaker, and incubated at 37° C. for 15 minutes. 20 μL Er was then added to each well and the plates were sealed, mixed, and incubated at 37° C. for 30 minutes with an added shaking at 15 minutes. The following controls were each included in quadruplicate: 2.4 μL DMSO+120 L GVB$^0$·MgEGTA (representing background signal); 2.4 μL DMSO+100 μL GVB$^0$·MgEGTA+20 μL Er (no serum, representing 0% CAP-mediated lysis); 2.4 μL DMSO+50 μL GVB$^0$·MgEGTA+50 μL 20% NHS+20 μL Er (no compound, representing 100% CAP-mediated lysis); and 2.4 μL DMSO+100 μL H$_2$O+20 μL Er (osmotic lysis, representing maximal lysis).

Following incubation, Er cells were removed by centrifugation at 800×g and 4° C. for 3 minutes, 100 μL supernatant per well was transferred to flat-bottom clear microtiter plates, and A$_{405}$ of the supernatant was measured in a Molecular Devices Spectramax Plus plate reader.

Example 10. CAP-Mediated Wieslab Assay

The complement system alternative pathway Wieslab kit (COMPL AP330) was purchased from Euro Diagnostica (Malmo, Sweden). The Wieslab assay for CAP-mediated TCC production was conducted as described by the manufacturer. Compound 1 was prepared individually in a seven-point two-fold dilution series at 100× final assay concentration in DMSO. Anti-C5 was prepared in a seven-point two-fold dilution series at 22× final assay concentration in the Diluent AP reagent provided with the Wieslab kit. Each of the 64 possible combinations of inhibitors at varying concentrations was tested in duplicate wells. 1.25 μL Compound 1 at the appropriate dilutions was added to microtiter wells. 125 μL NHS diluted ⅟₁₈× in Diluent AP was added to each well, and then 6 μL anti-C5 at the appropriate dilutions was added and mixed. 100 μL was transferred to wells of the CAP Wieslab plate. Positive and negative control wells were included in quadruplicate with no inhibitor and no serum respectively. Plates were incubated for 60 minutes at 37° C. Wells were emptied, washed 3× with washing solution, and incubated with 100 µL alkaline phosphatase-labelled detection antibody for 30 minutes at room temperature. Wells were emptied, washed 3× with washing solution, and incubated with 100 µL alkaline phosphatase substrate for 30 minutes at room temperature. $A_{405}$ in each well was measured in a Molecular Devices Spectramax Plus plate reader.

Example 11. C3 Fragment Deposition Inhibition on Rabbit Erythrocytes by Compound 1

Rabbit erythrocytes, C5-depleted normal human serum (C5-Dpl NHS), gelatin veronal buffer (GVB) without $Ca^{++}$ and $Mg^{++}$ ($GVB^0$), 100 mM $MgCl_2$+100 mM EGTA (MgEGTA) were obtained from Complement Technology Inc. (Tyler, TX). $GVB^0$·MgEGTA was prepared by mixing $GVB^0$ and 100 mM MgEGTA in a 9:1 ratio. FITC-conjugated anti-C3c antibody (cat #ab4212) and Alexa Fluor® 647-conjugated anti human CD59 antibody (cat #: ab187769) were purchased from Abcam (Cambridge, MA).

To assess C3 fragment deposition on rabbit erythrocytes, reactions were performed in volume of 100 µL containing C5-depleted normal human serum (C5-Dpl NHS) at a final concentration of 20% and rabbit erythrocytes at a final density of $5\times10^7$/mL in $GVB^0$·MgEGTA buffer in the absence or presence of Compound 1 at concentrations ranging from 0.0003 to 10 µM. Reactions were incubated at 37° C. for 15 minutes, the reactions were quenched by addition of EDTA at a final concentration of 20 mM. Cells were stained with a FITC-conjugated anti-C3c antibody at a dilution of 1:200 and C3 fragment deposition on the surface of rabbit erythrocytes was assessed by flow cytometry with BD Accuri C6 cytometer (BD Biosciences, San Jose, CA). Forward and side scatter parameters were used to gate intact erythrocytes. Controls included cells labeled with FITC-conjugated antibody isotype control. $IC_{50}$ values from each experiment were determined by curve-fitting of experimental data (the % C3 fragment-positive cells at increasing concentrations of inhibitor) to the four-parameter sigmoidal dose-response equation using non-linear regression analysis (Prism Software, GraphPad, La Jolla, CA).

Figure 6A:
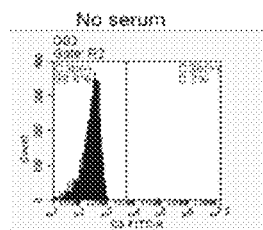
FIGS. 6A-6L are flow cytometry analyses of C3 fragment deposition on rabbit erythrocytes in the presence of serum and increasing concentrations of Compound 1. Cell surface C3 fragments were detected with anti-human C3c antibody as described in Example 11. The x-axis is the number of cells that stained positive with anti-C3c antibody and the y-axis is intensity measured in counts.
Figure 6B:
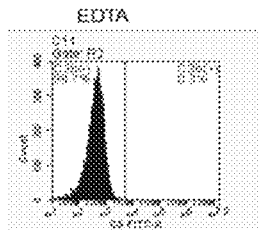
Figure 6C:
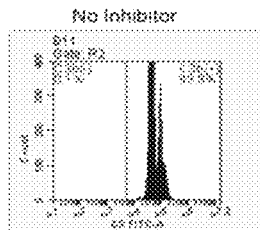
Figure 6D:
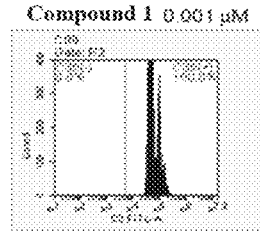
Figure 6E:
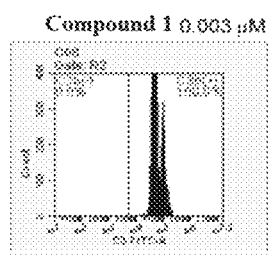
Figure 6F:
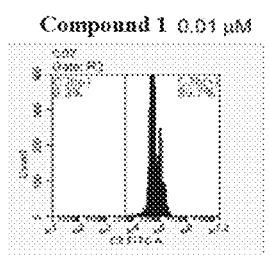
Figure 6G:
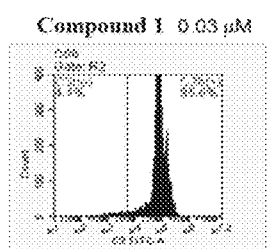
Figure 6H:
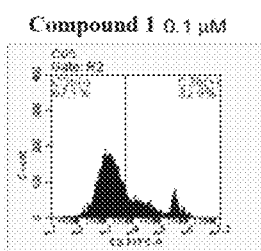
Figure 6I:
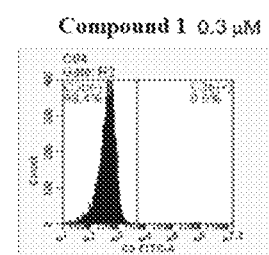
Figure 6J:
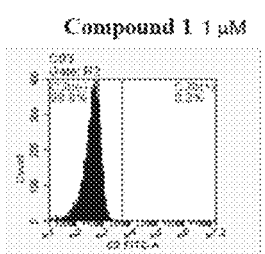
Figure 6K:
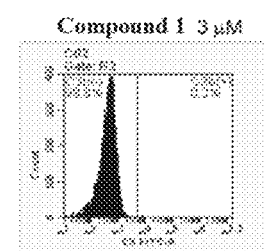
Figure 6L:
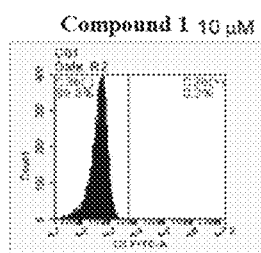
Figure 6M:
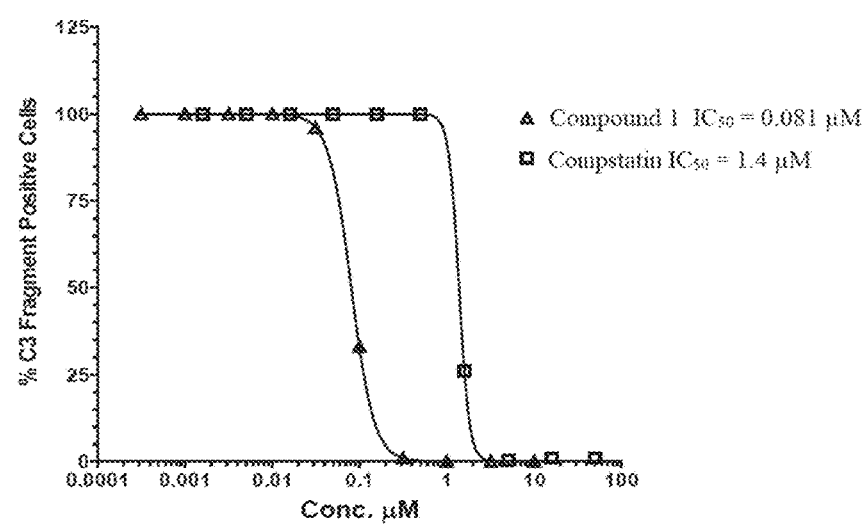
FIG. 6M is a dose-response curve showing the percentage of C3 fragment positive cells in the presence of increasing concentrations of Compound 1 and Compstatin as discussed in Example 11. The x-axis is the concentration of compound measured in M and the y-axis is C3 fragment positive cells measured as a percent.

C3 fragment deposition on rabbit erythrocytes after incubation with 20% C5-depleted normal human serum in the presence or absence of Compound 1 or compstatin was assessed using flow cytometry and anti-C3c antibody that recognizes C3 fragments of C3b and iC3b. Representative dot plots of the effect of Compound 1 on C3 fragment deposition are shown in FIGS. 6A-6L and the dose-response curves for Compound 1 and compstatin are shown FIG. 6M. As expected, ~0% of the cells stained positive with anti-C3c antibody in the absence of serum whereas ~100% of the cells stained positive with anti-C3c antibody in the presence of serum, indicating C3 fragment deposition. Furthermore, the C3 fragment deposition by the serum was abolished when EDTA was added, indicating the nature of complement-mediated process. When Compound 1 or compstatin were included in the reaction, the percentage of cells stained positive with anti-C3c antibody decreased with increasing concentrations of either inhibitors. The $IC_{50}$ value (0.096±0.021 µM) for Compound 1 was derived from two independent experiments while the $IC_{50}$ value (1.4 µM) of compstatin was derived from one experiment (Table 13).

TABLE 13

Inhibition of C3 Fragment deposition on rabbit erythrocytes

| Compound | $IC_{50}$ (µM) |
|---|---|
| Compound 1 | 0.096 ± 0.021 (N = 2) |
| Compstatin | 1.4 (N = 1) |

Example 12. C3 Fragment Deposition Inhibition on Artificial PNH Cells by Compound 1

Normal human type O red blood cells were purchased from BioreclamationIVT (Westbury, NY). 2-amino-ethyl-isothiouronium bromide (AET) was purchased from Sigma Aldrich. C5-depleted normal human serum (C5-Dpl NHS), gelatin veronal buffer (GVB) without $Ca^{++}$ and $Mg^{++}$ ($GVB^0$), 100 mM $MgCl_2$+100 mM EGTA (MgEGTA) were obtained from Complement Technology Inc. (Tyler, TX). $GVB^0$·MgEGTA was prepared by mixing $GVB^0$ and 100 mM MgEGTA in a 9:1 ratio. FITC-conjugated anti-C3c antibody (cat #ab4212) and Alexa Fluor® 647-conjugated anti human CD59 antibody (cat #: ab187769) were purchased from Abcam (Cambridge, MA).

Artificial PNH cells were prepared from fresh normal human erythrocytes (Type O) by reaction with an 8% solution (wt/vol) of AET at 37° C. for 9 minutes as described by Sirchia et al (Sirchia, G., S. Ferrone, and F. Mercuriali, The Action of Two Sulfhydryl Compounds on Normal Human Red Cells. Relationship to Red Cells of Paroxysmal Nocturnal Hemoglobinuria. Blood, 1965. 25: p. 502-10). After AET treatment, artificial PNH erythrocytes were centrifuged, supernatant was aspirated and cells were thoroughly washed with phosphate buffered saline (PBS) 3 times followed by washing with $GVB^0$ buffer (pH 8.0) for additional 3 times. After wash, cells were re-suspended in $GVB^0$·MgEGTA buffer (pH 6.4) to a hematocrit at $1\times10^9$/mL and kept at 4° C. for no more than 2 days. $GVB^0$·MgEGTA buffer (pH 6.4) was made by adjusting pH of $GVB^0$·MgEGTA buffer to 6.4 with HCl.

To assess C3 fragment deposition on artificial PNH erythrocytes, reactions were performed in a volume of 100 µL containing acidified C5-Dpl NHS at a final concentration of 32% and the artificial PNH erythrocytes at a final density of $5\times10^7$/mL in $GVB^0$·MgEGTA buffer in the absence or presence of Compound 1 at concentrations ranging from 0.0003 to 10 µM. Note, serum acidification occurred post mixing the serum with the compound and prior to adding the artificial PNH erythrocytes. Reactions were incubated at 37° C. for 30 minutes, the reactions were quenched by addition of EDTA at a final concentration of 20 mM. Cells were stained with a FITC-conjugated anti-C3c antibody and Alexa Fluor® 647-conjugated anti human CD59 antibody at a dilution of 1:200. C3 fragment deposition on the surface of the erythrocytes was assessed by flow cytometry with BD Accuri C6 cytometer (BD Biosciences, San Jose, CA). Forward and side scatter parameters were used to gate intact erythrocytes. Controls included cells stained with FITC- and Alexa Fluor® 647-conjugated isotype controls. $IC_{50}$ values from each experiment were determined by curve-fitting of experimental data (the % C3 fragment-positive cells at increasing concentrations of inhibitor) to the four-parameter sigmoidal dose-response equation using non-linear regression analysis (Prism Software, GraphPad, La Jolla, CA).

C3 fragment deposition on artificial PNH cells after incubation with 32% C5-depleted normal human serum under the treatment of Compound 1 or compstatin was accessed through flow cytometry.

Figure 7M:
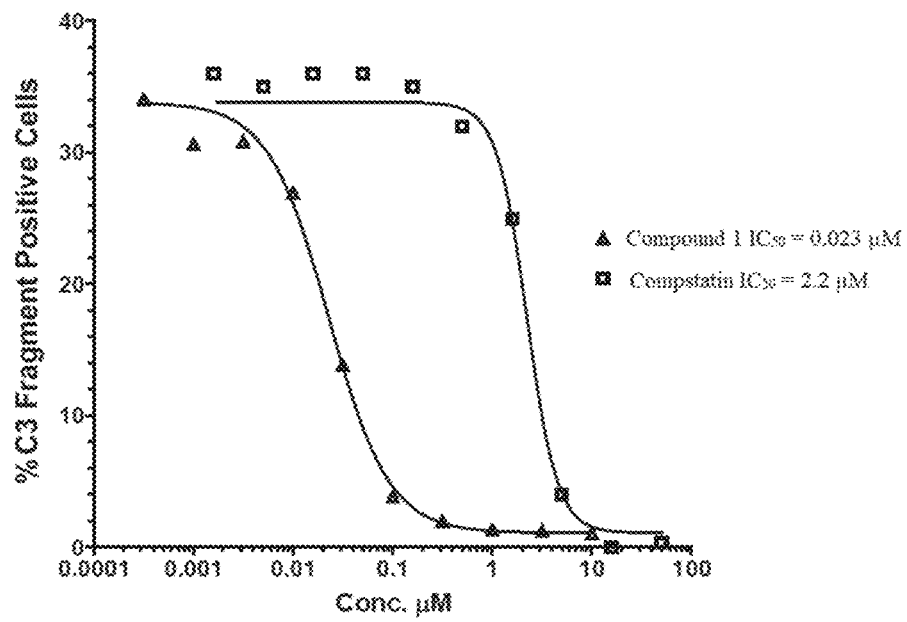
FIG. 7M is a dose-response curve showing the percentage of C3 fragment positive cells in the presence of increasing concentrations of Compound 1 and Compstatin as discussed in Example 12. The x-axis is the concentration of compound measured in M and the y-axis is C3 fragment positive cells measured as a percent.
Figure 8:
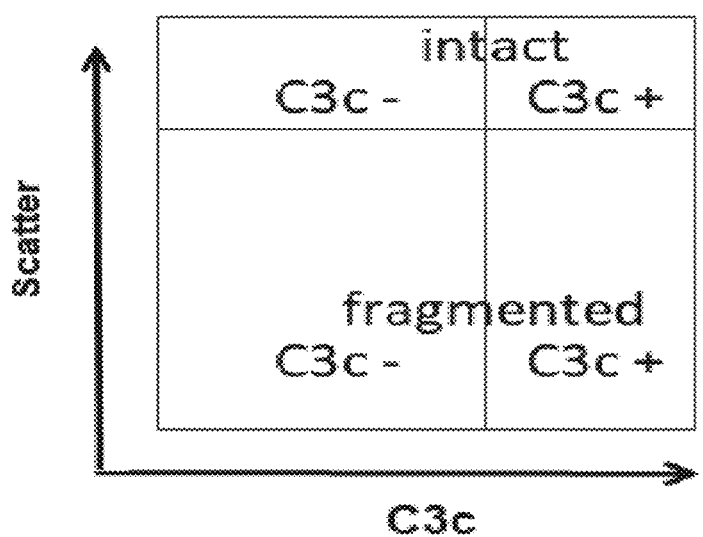
FIG. 8 is a representative key for flow cytometry analyses of C3 fragment deposition on intact and fragmented PNH erythrocytes. The upper left quadrant is negative for C3 fragment deposition on intact PNH erythrocytes. The lower left quadrant is negative for C3 fragment deposition on fragmented PNH erythrocytes. The upper right quadrant is positive for C3 fragment deposition on intact PNH erythrocytes. The lower right quadrant is positive for C3 fragment deposition on fragmented PNH erythrocytes. The x-axis is increasing amounts of C3 convertase and the y-axis is the scatter intensity.
Figure 9:
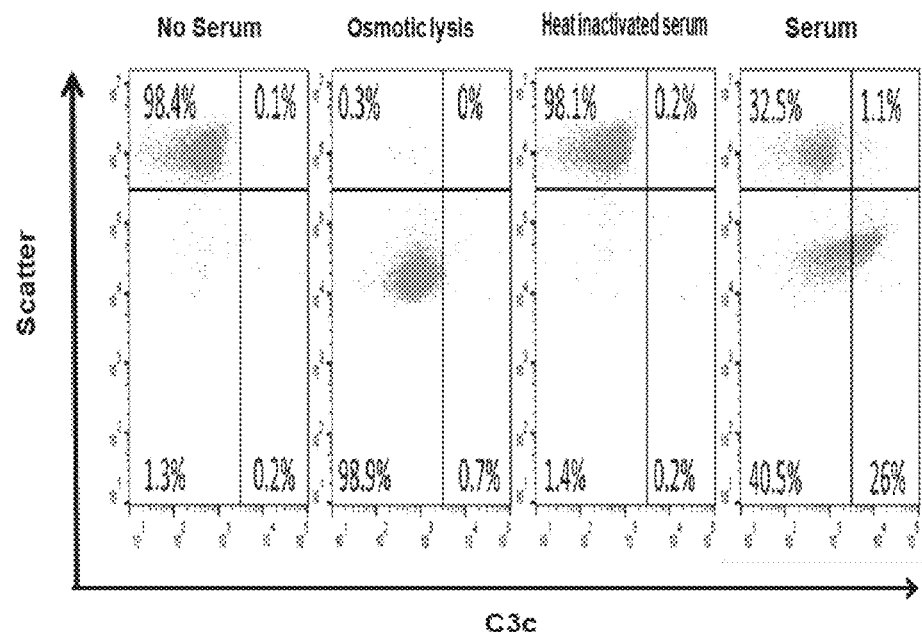
FIG. 9 is an evaluation of C3 fragment deposition on PNH erythrocytes under various conditions including no serum, osmotic lysis, heat inactivated serum, and serum. The dot plots show the distribution of erythrocytes after being labeled with anti-CD47 (positive) and anti-human CD59 (negative) and anti-human C3c (C3 fragment deposition) antibodies. The x-axis is increasing amounts of C3 convertase and the y-axis is the scatter intensity.
Figure 10:
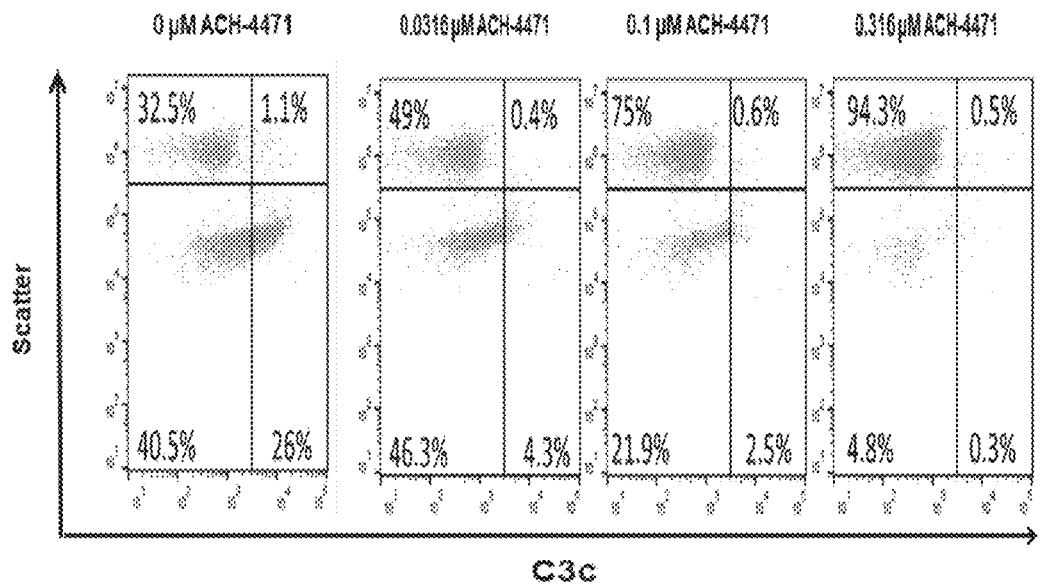
FIG. 10 is an evaluation of C3 fragment deposition on PNH erythrocytes with increasing concentrations of Compound 1 alone. The dot plots show the distribution of erythrocytes after being labeled with anti-CD47 (positive) and anti-human CD59 (negative) and anti-human C3c (C3 fragment deposition) antibodies. The x-axis is increasing amounts of C3 convertase and the y-axis is the scatter intensity.
Figure 11:
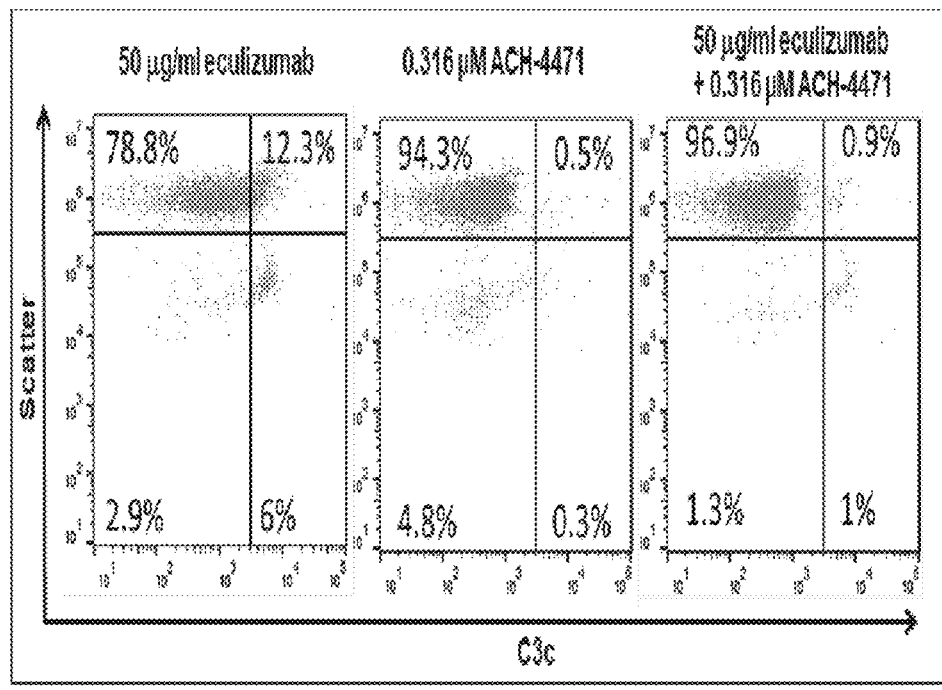
FIG. 11 is an evaluation of C3 fragment deposition on PNH erythrocytes with eculizumab alone, Compound 1 alone, and the combination of eculizumab and Compound 1. The dot plots show the distribution of erythrocytes after being labeled with anti-CD47 (positive) and anti-human CD59 (negative) and anti-human C3c (C3 fragment deposition) antibodies. The x-axis is increasing amounts of C3 convertase and the y-axis is the scatter intensity.
Figure 12:
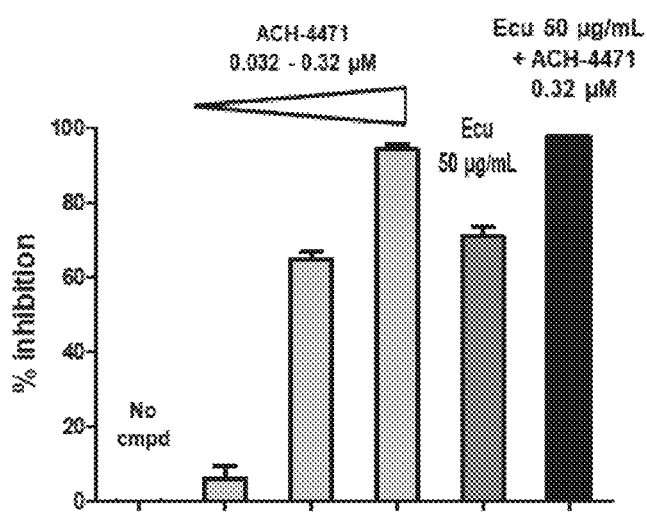
FIG. 12 is a bar-graph showing the inhibition of PNH erythrocyte hemolysis under physiological conditions with increasing levels of Compound 1, eculizumab alone, and the combination of eculizumab and Compound 1. The x-axis is the compound dose and the y-axis is the percent inhibition of hemolysis.

Representative dot plots for the inhibitory effect of Compound 1 and compstatin on C3 fragment deposition are shown in FIGS. 7A-7L, and the dose-response curves for the two inhibitors are shown FIG. 7M. As predicted, after AET treatment, all erythrocytes (artificial PNH cells) were CD59 negative, whereas non-treated erythrocytes were CD59 positive (data not shown).

As expected, ~0% of the cells stained positive with anti-C3c antibody in the absence of serum, whereas ~27% of the cells stained positive with anti-C3c antibody in the presence of serum, indicating C3 fragment deposition. Furthermore, the C3 fragment deposition by the serum was abolished when EDTA was added, indicating the nature of complement-mediated process. When Compound 1 or compstatin was included in the reaction, the percentage of cells stained positive with anti-C3c antibody decreased with increasing concentrations of compound, showing the inhibition of C3 fragment deposition. The $IC_{50}$ values for Compound 1 and compstatin are 0.027±0.0047 μM and 2.2±0.031 μM, respectively. The $IC_{50}$ values were derived from two independent experiments (Table 14).

TABLE 14

Inhibition of C3 Fragment deposition on artificial PNH cells

| Compound | $IC_{50}$ (μM) |
| --- | --- |
| Compound 1 | 0.027 ± 0.0047 (N = 2) |
| Compstatin | 2.2 ± 0.031 (N = 2) |

Example 13. Inhibition of C3 Fragment Deposition on PNH Cells Under Physiological Conditions Serum-mediated C3 fragment deposition on erythrocytes from PNH subject A was assessed with Compound 1 alone and in combination with eculizumab. Physiological conditions were defined as 5 min pre-incubation of serum with inhibitor, 72% ABO blood group-compatible serum, 5×10^7/mL erythrocytes from PNH subject A, GVB++ buffer, 37° C. for 1 hour, EDTA termination. Hemolysis was assessed from $A_{405}$ of supernatants following centrifugation. C3 fragment deposition on intact and fragmented cells was assessed by flow cytometry using FITC-conjugated anti-C3c (Abcam Ab4212, 1:200), PE-conjugated anti-CD47 (R&D Systems FAB4670P, 1:50), and APC-conjugated anti-CD59 (Abcam Ab187769, 1:200 dilution) following dilution of reaction mixtures in FC buffer (PBS+15 mM EDTA, 1% BSA). After incubation at room temperature for 30 min, samples were diluted to final 1:20 in FC buffer and examined by flow cytometry (BD Accuri C6) with a Fsc-H>20,000 threshold. Intact and fragmented PNH erythrocytes were identified by anti-CD47 (positive) and anti-CD59 (negative) staining; Intact and fragmented cells were distinguished from each other by size (FSC-A); C3 fragment deposition was assessed by anti-C3c staining.

Example 14. A Phase 2 Open-Label Study of Compound 1 in Subjects with Paroxysmal Nocturnal Hemoglobinuria (PNH) Who have an Inadequate Response to Eculizumab Monotherapy Eculizumab Recommended Dosage Regimen for PNH For patients 18 years of age and older, eculizumab therapy consists of:

600 mg weekly for the first 4 weeks, followed by;
900 mg for the fifth dose 1 week later, then
900 mg every 2 weeks thereafter.

For patients less than 18 years of age, eculizumab is administered based upon body weight.

| Patient Body Weight | Induction | Maintenance |
| --- | --- | --- |
| 40 kg and over | 900 mg weekly × 4 doses | 1200 mg at week 5; then 1200 mg every 2 weeks |
| 30 kg to less than 40 kg | 600 mg weekly × 2 doses | 900 mg at week 3; then 900 mg every 2 weeks |
| 20 kg to less than 30 kg | 600 mg weekly × 2 doses | 600 mg at week 3; then 600 mg every 2 weeks |
| 10 kg to less than 20 kg | 600 mg weekly × 1 dose | 300 mg at week 3; then 300 mg every 2 weeks |
| 5 kg to less than 10 kg | 300 mg weekly × 1 dose | 300 mg at week 2; then 300 mg every 3 weeks |

Eculizumab is administered by intravenous infusion over 35 minutes in adults and 1 to 4 hours in pediatric patients via gravity feed, a syringe-type pump, or an infusion pump.

Dosage Regimen for Compound 1 in Clinical Studies

The starting dose of compound 1 is based upon group assignment. The Group 1 dose is 100 mg three times daily (TID). The Group 2 dose is 150 mg TID. The Group 3 dose is 200 mg TID. The Group 4 dose will receive the optimal dose determined from Groups 1-3.

Compound 1 is administered orally three times daily (TID) over a period of 24 weeks while patients continue to receive eculizumab at their usual dose and schedule described above. Compound 1 is dosed in the morning, a second dose approximately 8 hours later, and a third dose approximately 8 hours after the second dose. All doses are taken approximately 15-30 minutes after completion of a meal or snack.

This study will include up to 12 subjects who will receive 24 weeks of daily oral treatment with Compound 1 plus intravenous (IV) eculizumab administered at the subject's usual dose and schedule. This will be followed by a long-term extension phase.

There will be a minimum of 4 weeks of treatment required at each dose level before dosing of the subsequent group of subjects at the next highest dose level. The first three groups will include 2 subjects per group to determine an optimal Compound 1 dose for the remaining 6 subjects in the fourth group.

Upon completion of 24 weeks of treatment, subjects will then enter a long-term extension phase of this study with the same Compound 1 dose plus eculizumab as they were receiving at the end of 24-week treatment phase.

Subjects will return to the clinic for safety, PK, and other assessments at Week1, Week 2, Week 4, Week 8, and Week 12, and then every 4 weeks until Week 24.

The study population will include adult PNH subjects with RBC-transfusion-dependent anemia (defined as having received at least one RBC transfusion within 12 weeks prior to screening) and who are receiving a stable dose of eculizumab (have been receiving eculizumab at approved or higher doses for at least 24 weeks prior to entry without change in dose or schedule for at least 12 weeks).

2 subjects in the first dose level of 100 mg TID have been completed and data collected through 4 weeks. Data collected include lactate dehydrogenase (LDH) levels, hemoglobin levels, reticulocytes, PNH red blood cells (Type III) percentage, C3 Fragment Deposition percentage, and bilirubin levels and their changes from baseline.

Figure 13A:
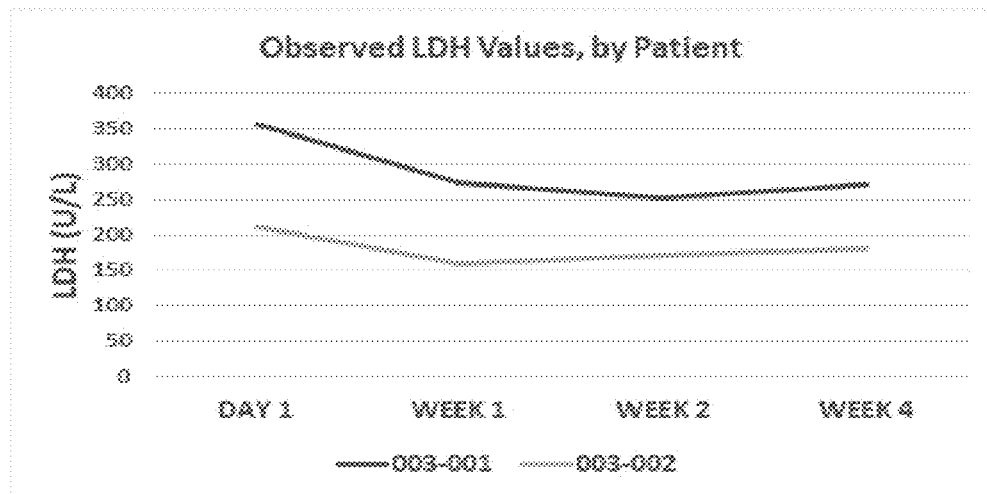
FIG. 13A is a line graph showing observed lactate dehydrogenase levels found in blood collected from two PNH subjects treated with 100 mg. of Compound 1 in combination with intravenous eculizumab over multiple time points. The x-axis includes the specific timepoints Day 1 (baseline), Week 1, Week 2, and Week 4. The y-axis is the concentration of lactate dehydrogenase in blood measured in U/L.
Figure 13B:
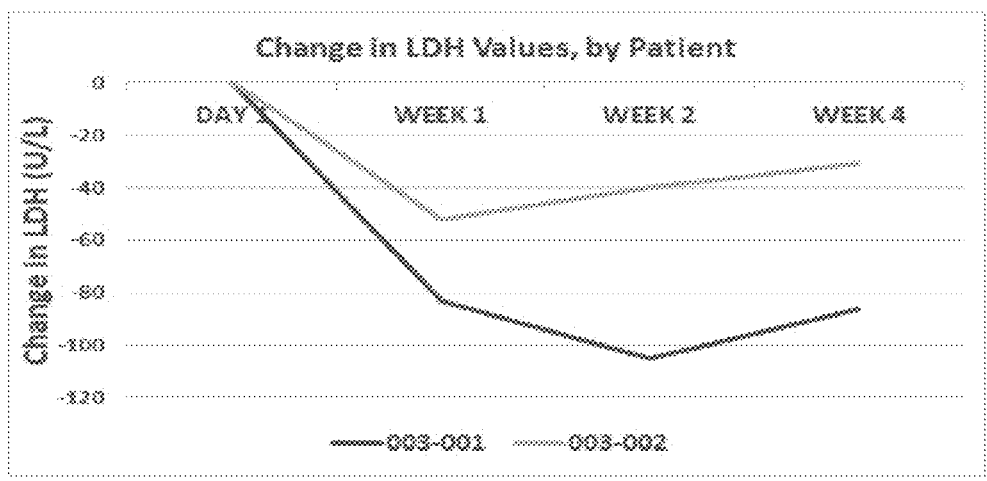
FIG. 13B is a line graph showing the change from baseline of lactate dehydrogenase levels found in blood collected from two PNH subjects treated with 100 mg. of Compound 1 in combination with intravenous eculizumab over multiple time points. The x-axis includes the specific timepoints Day 1 (baseline), Week 1, Week 2, and Week 4. The y-axis is the change in concentration of lactate dehydrogenase from baseline in blood measured in U/L.

Lactate dehydrogenase is a pharmacodynamic marker that is measured from blood drawn on Day 1, Week 1, Week 2, and Week 4 (FIGS. 13A & 13B and Table 15). High levels of LDH in the blood can be an indication of hemolysis.

TABLE 15

Lactate Dehydrogenase Levels and Change from Baseline

| LDH (U/L) | Visit | 003-001 | 003-002 |
|---|---|---|---|
| Observed | DAY 1 | 357 | 210 |
| Observed | WEEK 1 | 274 | 158 |
| Observed | WEEK 2 | 252 | 170 |
| Observed | WEEK 4 | 271 | 179 |
| CFB | DAY 1 | 0 | 0 |
| CFB | WEEK 1 | −83 | −52 |
| CFB | WEEK 2 | −105 | −40 |
| CFB | WEEK 4 | −86 | −31 |

Figure 14A:
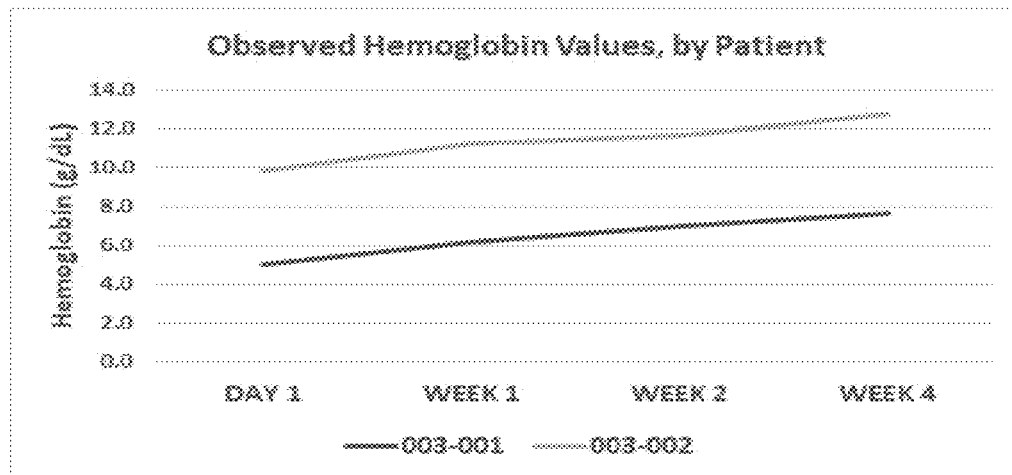
FIG. 14A is a line graph showing observed hemoglobin levels found in blood collected from two PNH subjects treated with 100 mg. of Compound 1 in combination with intravenous eculizumab over multiple time points. The x-axis includes the specific timepoints Day 1 (baseline), Week 1, Week 2, and Week 4. The y-axis is the concentration of hemoglobin in blood measured in g/dL.
Figure 14B:
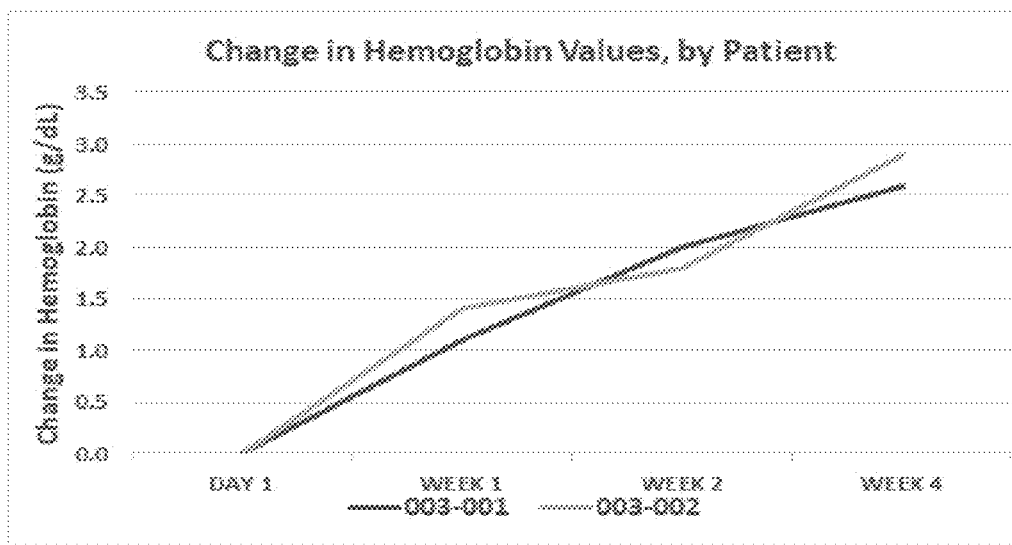
FIG. 14B is a line graph showing the change from baseline of hemoglobin levels found in blood collected from two PNH subjects treated with 100 mg of Compound 1 in combination with intravenous eculizumab over multiple time points. The x-axis includes the specific timepoints Day 1 (baseline), Week 1, Week 2, and Week 4. The y-axis is the change in concentration of hemoglobin from baseline in blood measured in g/dL.

Free hemoglobin is a pharmacodynamic marker that is measured from blood drawn on Day 1, Week 1, Week 2, and Week 4 (FIGS. 14A & 14B and Table 16). Low levels of hemoglobin is a sign of hemolytic anemia.

TABLE 16

Hemoglobin Levels and Change from Baseline

| HEMOGLOBIN (g/dL) | Visit | 003-001 | 003-002 |
|---|---|---|---|
| Observed | DAY 1 | 5.0 | 9.8 |
| Observed | WEEK 1 | 6.1 | 11.2 |
| Observed | WEEK 2 | 7.0 | 11.6 |
| Observed | WEEK 4 | 7.6 | 12.7 |
| CFB | DAY 1 | 0.0 | 0.0 |
| CFB | WEEK 1 | 1.1 | 1.4 |
| CFB | WEEK 2 | 2.0 | 1.8 |
| CFB | WEEK 4 | 2.6 | 2.9 |

Figure 15A:
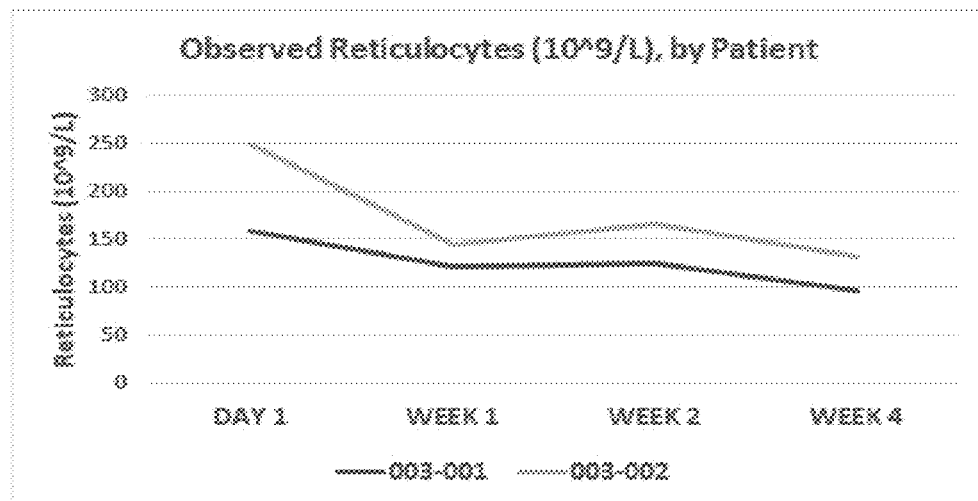
FIG. 15A is a line graph showing the observed reticulocyte levels found in blood collected from two PNH subjects treated with 100 mg of Compound 1 in combination with intravenous eculizumab over multiple time points. The x-axis includes the specific timepoints Day 1 (baseline), Week 1, Week 2, and Week 4. The y-axis is the concentration of reticulocytes in blood measured in $10^9$/L.
Figure 15B:
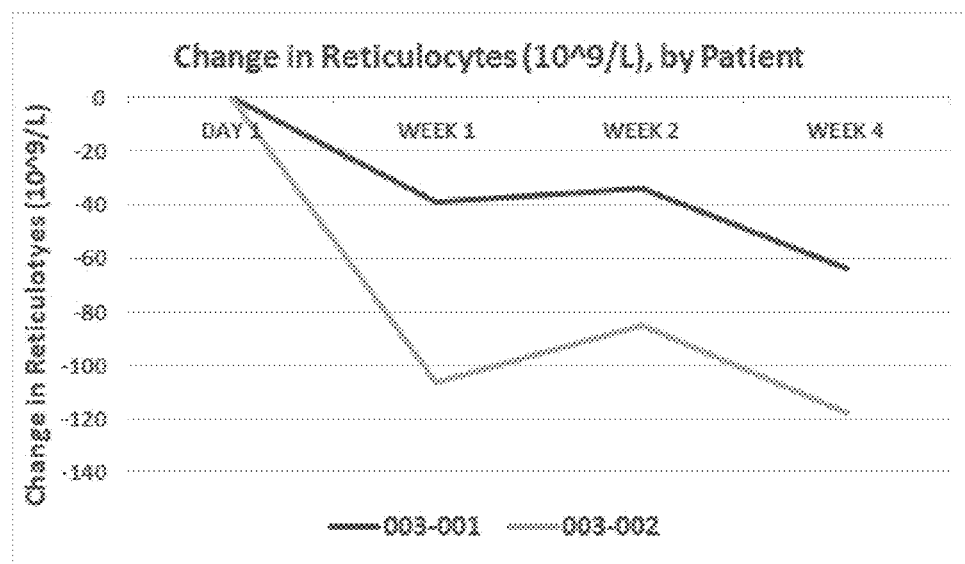
FIG. 15B is a line graph showing the change from baseline of reticulocyte levels found in blood collected from two PNH subjects treated with 100 mg of Compound 1 in combination with intravenous eculizumab over multiple time points. The x-axis includes the specific timepoints Day 1 (baseline), Week 1, Week 2, and Week 4. The y-axis is the change in number of reticulocytes from baseline in blood measured in $10^9$/L.

A reticulocyte count is a pharmacodynamic marker that is measured from blood drawn on Day 1, Week 1, Week 2, and Week 4 (FIGS. 15A & 15B and Table 17). A reticulocyte count measures the number of immature red blood cells in a blood sample. People who have PNH may have elevated reticulocyte counts because their bone marrow is producing a lot of new red blood cells.

TABLE 17

Reticulocyte counts and Change from Baseline

| RETICULOCYTES (10^9/L) | Visit | 003-001 | 003-002 |
|---|---|---|---|
| Observed | DAY 1 | 159 | 250 |
| Observed | WEEK 1 | 120 | 144 |
| Observed | WEEK 2 | 125 | 165 |
| Observed | WEEK 4 | 95 | 132 |
| CFB | DAY 1 | 0 | 0 |
| CFB | WEEK 1 | −39 | −106 |
| CFB | WEEK 2 | −34 | −85 |
| CFB | WEEK 4 | −64 | −118 |

Figure 16A:
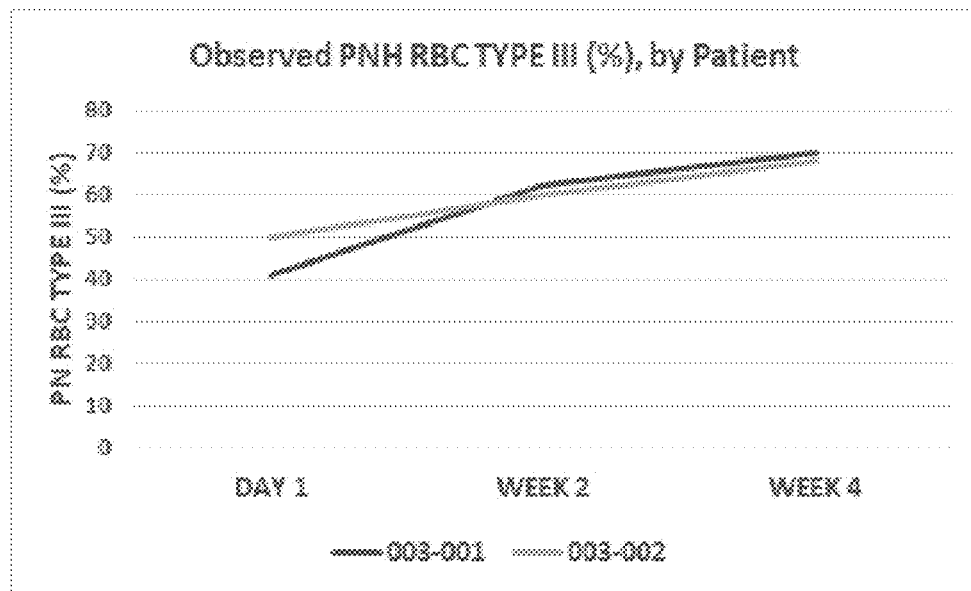
FIG. 16A is a line graph showing the observed PNH erythrocyte Type III percentage found in blood collected from two PNH subjects treated with 100 mg of Compound 1 in combination with intravenous eculizumab over multiple time points. The x-axis includes the specific timepoints Day 1 (baseline), Week 2, and Week 4. The y-axis is the percentage of PNH erythrocyte Type III in blood.
Figure 16B:
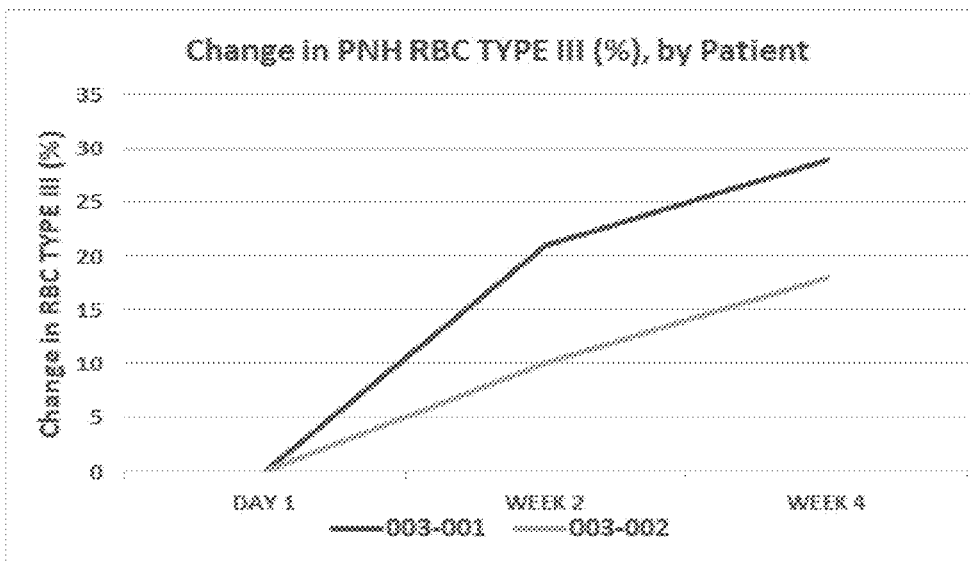
FIG. 16B is a line graph showing the change from baseline of percentage PNH erythrocytes Type III found in blood collected from two PNH subjects treated with 100 mg of Compound 1 in combination with intravenous eculizumab over multiple time points. The x-axis includes the specific timepoints Day 1 (baseline), Week 2, and Week 4. The y-axis is the change in percentage of PNH erythrocytes Type III from baseline in blood.

Measuring the percentage of PNH Type III red blood cells is a pharmacodynamic marker that is measured by flow cytometry, which provides information on cell size, shape, and percentage of a type of cell. This assay determines whether CD55 and CD59 are missing from the surface of red blood cells. These proteins help protect normal cells from hemolysis. PNH Type III cells are extremely sensitive to the complement system and hemolysis. PNH Type III cell percentage is measured from plasma drawn on Day 1, Week 2, and Week 4 (FIGS. 16A & 16B and Table 18).

TABLE 18

PNH Red Blood Cell (Type III) Percentage and Change from Baseline

| PNH RBC (TYPE III) (%) | Visit | 003-001 | 003-002 |
|---|---|---|---|
| Observed | DAY 1 | 41 | 50 |
| Observed | WEEK 2 | 62 | 60 |
| Observed | WEEK 4 | 70 | 68 |
| CFB | DAY 1 | 0 | 0 |
| CFB | WEEK 2 | 21 | 10 |
| CFB | WEEK 4 | 29 | 18 |

Figure 17A:
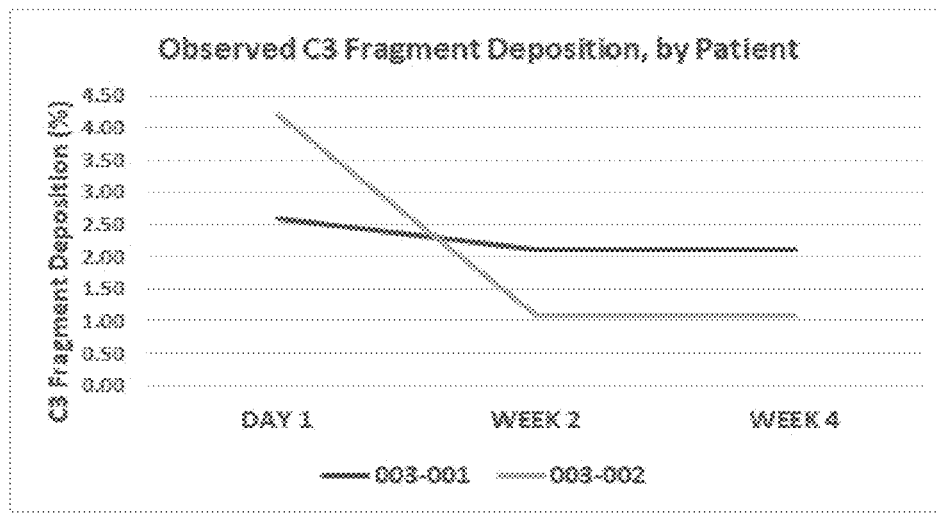
FIG. 17A is a line graph showing the observed C3 fragment deposition percentage found in blood collected from two PNH subjects treated with 100 mg of Compound 1 in combination with intravenous eculizumab over multiple time points. The x-axis includes the specific timepoints Day 1 (baseline), Week 2, and Week 4. The y-axis is the percentage of C3 fragment deposition in blood.
Figure 17B:
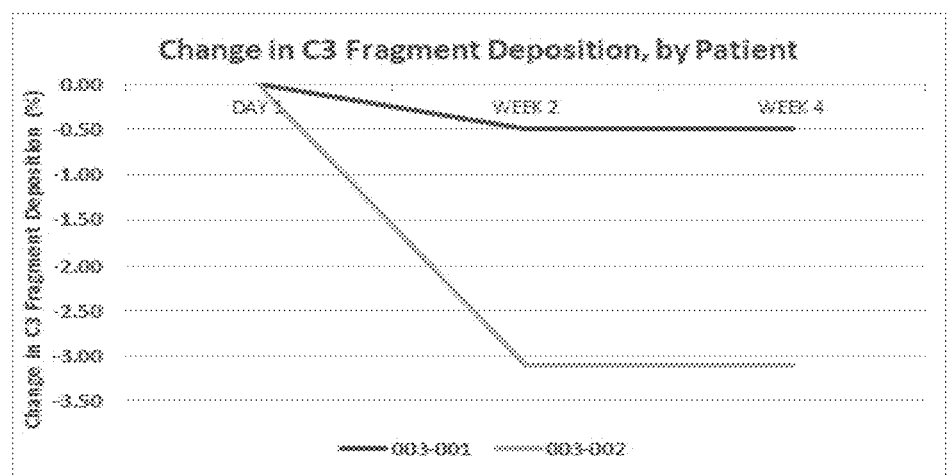
FIG. 17B is a line graph showing the change from baseline of the percentage of C3 fragment deposition found in blood collected from two PNH subjects treated with 100 mg of Compound 1 in combination with intravenous eculizumab over multiple time points. The x-axis includes the specific timepoints Day 1 (baseline), Week 2, and Week 4. The y-axis is the change in percentage of C3 fragment deposition from baseline in blood.

Measurement of C3 fragment deposition percentage is a pharmacodynamic marker that is measured by flow cytometry of subject plasma samples collected on Day 1, Week 2, and Week 4 (FIGS. 17A & 17B and Table 19). Uncontrolled C3 activation due to the absence of CD55 on red blood cells may result in opsonization of red blood cells, leading to clinically meaningful extravascular hemolysis.

TABLE 19

C3 Fragment Deposition Percentage and Change from Baseline

| C3 FRAGMENT DEPOSITION (%) | Visit | 003-001 | 003-002 |
|---|---|---|---|
| Observed | DAY 1 | 2.60 | 4.20 |
| Observed | WEEK 2 | 2.10 | 1.10 |
| Observed | WEEK 4 | 2.10 | 1.10 |
| CFB | DAY 1 | 0.00 | 0.00 |
| CFB | WEEK 2 | −0.50 | −3.10 |
| CFB | WEEK 4 | −0.50 | −3.10 |

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

The invention claimed is:

1. A method for treating paroxysmal nocturnal hemoglobinuria (PNH) in a human in need thereof comprising administering to the subject a therapeutically effective amount of an anti-C5 monoclonal antibody in combination with a therapeutically effective amount of orally administered Compound 1:

1

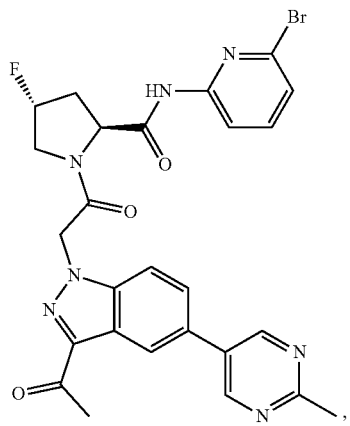

or a pharmaceutically acceptable salt thereof;
wherein the human at the time of the first administration of Compound 1 is experiencing extravascular hemolysis.

2. The method of claim 1, wherein the human has anemia at the time of the first administration of Compound 1.

3. The method of claim 1, wherein the human has a hemoglobin level of less than about 10 g/dL at the time of the first administration of Compound 1.

4. The method of claim 1, wherein the human has been receiving the C5 inhibitor for at least three months prior to the first administration of Compound 1, wherein the C5 inhibitor is an anti-C5 monoclonal antibody.

5. A method for treating paroxysmal nocturnal hemoglobinuria (PNH) in a human in need thereof comprising:
   a. orally administering to the human a therapeutically effective amount of Compound 1, which has the structure:

1

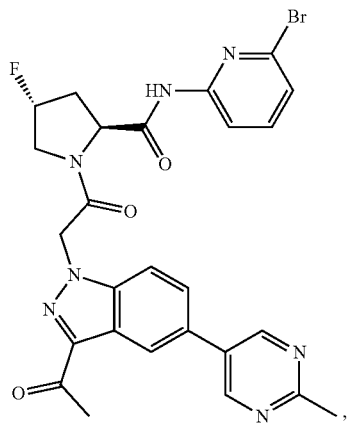

or a pharmaceutically acceptable salt thereof;
   b. administering to the human a therapeutically effective amount of a complement 5 (C5) inhibitor, wherein the C5 inhibitor is an anti-C5 monoclonal antibody;
   wherein the human at the time of the first administration of Compound 1 has previously been receiving a therapeutic regimen comprising administration of the C5 inhibitor; and,
   wherein the human at the time of the first administration of Compound 1 is experiencing extravascular hemolysis.

6. The method of claim 5, wherein the human has a hemoglobin level of less than about 10 g/dL at the time of the first administration of Compound 1.

7. The method of claim 5, wherein the human has a LDH level of less than 250 U/L at the time of the first administration of Compound 1.

8. The method of claim 5, wherein the human has received one or more blood transfusions within the twelve months prior to the first administration of Compound 1.

9. The method of claim 5, wherein the human has been receiving a C5 inhibitor for at least three months prior to the first administration of Compound 1, wherein the C5 inhibitor is an anti-C5 monoclonal antibody.

10. A method for treating paroxysmal nocturnal hemoglobinuria (PNH) in a human in need thereof comprising:
    a. orally administering to the human a therapeutically effective amount of Compound 1, which has the structure:

1

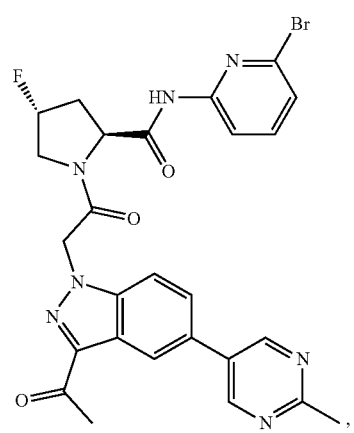

or a pharmaceutically acceptable salt thereof;
    b. administering to the human a therapeutically effective amount of a complement 5 (C5) inhibitor, wherein the C5 inhibitor is an anti-C5 monoclonal antibody;
    wherein the human at the time of the first administration of Compound 1 has previously been receiving a therapeutic regimen comprising administration of the C5 inhibitor; and,
    wherein the human at the time of the first administration of Compound 1 is experiencing residual intravascular hemolysis.

11. The method of claim 10, wherein the human has a hemoglobin level of less than about 10 g/dL at the time of the first administration of Compound 1.

12. The method of claim 10, wherein the human has a LDH level of greater than 250 U/L at the time of the first administration of Compound 1.

13. The method of claim 10, wherein the human has received one or more blood transfusions within the twelve months prior to the first administration of Compound 1.

14. The method of claim 10, wherein the human has been receiving a C5 inhibitor for at least three months prior to the first administration of Compound 1, wherein the C5 inhibitor is an anti-C5 monoclonal antibody.

15. A method for treating paroxysmal nocturnal hemoglobinuria (PNH) in a human in need thereof comprising
    a. orally administering to the human a therapeutically effective amount of Compound 1, which has the structure:

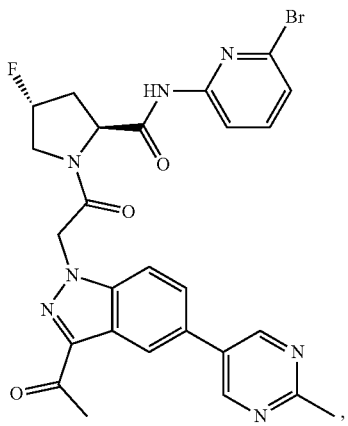

or a pharmaceutically acceptable salt thereof;

b. administering to the human a therapeutically effective amount of a complement 5 (C5) inhibitor, wherein the C5 inhibitor is an anti-C5 monoclonal antibody;

wherein the human at the time of the first administration of Compound 1 has previously been receiving a therapeutic regimen comprising administration of the C5 inhibitor; and, wherein the human at the time of the first administration of Compound 1 has a hemoglobin level of less than about 10 g/dL.

16. The method of claim 15, wherein the human has a hemoglobin level of less than about 8 g/dL at the time of the first administration of Compound 1.

17. The method of claim 15, wherein the human has a LDH level of greater than about 250 U/L at the time of first administration of Compound 1.

18. The method of claim 15, wherein the human has a LDH level of less than about 250 U/L at the time of first administration of Compound 1.

19. The method of claim 15, wherein the human has received one or more blood transfusions within the twelve months prior to the first administration of Compound 1.

20. The method of claim 15, wherein the human has been receiving a C5 inhibitor for at least three months prior to the first administration of Compound 1, wherein the C5 inhibitor is an anti-C5 monoclonal antibody.

21. The method of claim 1, wherein the anti-C5 monoclonal antibody is eculizumab or ALXN1210.

22. The method of claim 6, wherein the anti-C5 monoclonal antibody is eculizumab or ALXN1210.

23. The method of claim 10, wherein the anti-C5 monoclonal antibody is eculizumab or ALXN1210.

24. The method of claim 15, wherein the anti-C5 monoclonal antibody is eculizumab or ALXN1210.

* * * * *

UNITED STATES PATENT AND TRADEMARK OFFICE
CERTIFICATE OF CORRECTION

PATENT NO. : 12,076,319 B2
APPLICATION NO. : 16/700910
DATED : September 3, 2024
INVENTOR(S) : Mingjun Huang et al.

Page 1 of 1

It is certified that error appears in the above-identified patent and that said Letters Patent is hereby corrected as shown below:

In the Claims

Column 94, Line 22, replace "claim 6" with --claim 5--.

Signed and Sealed this
First Day of April, 2025

Coke Morgan Stewart
*Acting Director of the United States Patent and Trademark Office*